US012630796B2

(12) United States Patent

He

(10) Patent No.: US 12,630,796 B2
(45) Date of Patent: May 19, 2026

(54) SYSTEM, DEVICE, AND METHOD FOR SINGLE-CELL ENCAPSULATION AND CULTURE

(71) Applicant: UNIVERSITY OF MARYLAND, COLLEGE PARK, College Park, MD (US)

(72) Inventor: Xiaoming He, Bethesda, MD (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 740 days.

(21) Appl. No.: 17/920,440

(22) PCT Filed: Apr. 21, 2021

(86) PCT No.: PCT/US2021/028503
§ 371 (c)(1),
(2) Date: Oct. 21, 2022

(87) PCT Pub. No.: WO2021/216789
PCT Pub. Date: Oct. 28, 2021

(65) Prior Publication Data
US 2023/0174912 A1 Jun. 8, 2023

Related U.S. Application Data

(60) Provisional application No. 63/013,173, filed on Apr. 21, 2020.

(51) Int. Cl.
*C12M 1/12* (2006.01)
*C12N 5/00* (2006.01)

(52) U.S. Cl.
CPC ........... *C12M 25/16* (2013.01); *C12N 5/0012* (2013.01); *C12N 2533/74* (2013.01); *C12N 2533/78* (2013.01); *C12N 2537/10* (2013.01)

(58) Field of Classification Search
CPC .............................. C12N 11/10; C12N 5/0012
See application file for complete search history.

(56) References Cited

U.S. PATENT DOCUMENTS

| | | | |
|---|---|---|---|
| 7,625,758 B2 | 12/2009 | Berkelman | |
| 7,863,048 B2 | 1/2011 | Berkelman | |
| 2014/0127290 A1* | 5/2014 | He ....................... | A61K 9/5089 435/178 |

FOREIGN PATENT DOCUMENTS

| | | |
|---|---|---|
| WO | 2013/104686 A1 | 7/2013 |
| WO | 2019/010587 A1 | 1/2019 |

OTHER PUBLICATIONS

Libre Text "4.4: Studying Cells-Cell Size" from Boundless General Biology, accessed online on Jul. 29, 25 (Year: 2025).*
Oliveira et al. "Stem cells in human breast cancer" Histology and Histopathology• Mar. 2010, 16 pages (Year: 2010).*
Li et al. "Unraveling the roles of CD44/CD24 and ALDH1 as cancer stem cell markers in tumorigenesis and metastasis" Scientific Reports | 7: 13856, 2017, 15 pages (Year: 2017).*
International Search Report and Written Opinion issued in corresponding International Application No. PCT/US2021/028503 dated Aug. 16, 2021, pp. 1-12.
Han, S. et al., "Knock out CD44 in reprogrammed liver cancer cell C3A increases CSCs stemness and promotes differentiation" Oncotarget (Dec. 2015) pp. 44452-44465, vol. 6, No. 42.
Wang, H. et al., "Bioinspired One Cell Culture Isolates Highly Tumorigenic and Metastatic Cancer Stem Cells Capable of Multilineage Differentiation" Advanced Science (Apr. 2020) pp. 1-12, vol. 7, No. 11(2000259).
Zhao, S. et al., "Bioengineering of injectable encapsulated aggregates of pluripotent stem cells for therapy of myocardial infarction" Nature Commun. (Oct. 2016) pp. 1-2, vol. 7:13306.
Agarwal, P. et al., "One-step microfluidic generation of pre-hatching embryo-like core-shell microcapsules for miniaturized 3D culture of pluripotent stem cells" Lab Chip (Dec. 2013) pp. 4525-4533, vol. 13.
Zhang, W. et al., "A novel core-shell microcapsule for encapsulation and 3D culture of embryonic stem cells" Journal of Materials Chemistry B (Feb. 2013) pp. 1002-1009, vol. 1.
Xu, J. et al., "Bioinspired 3D culture in nanoliter hyaluronic acid-rich core-shell hydrogel microcapsules isolates highly pluripotent human iPSCs" Small (Jul. 2021) pp. 1-13, vol. 17: 2102219.
Agarwal, P. et al., "A Biomimetic Core-Shell Platform for Miniaturized 3D Cell and Tissue Engineering" Particle & Particles Systems Characterization (Aug. 2015) pp. 809-816, vol. 32.

* cited by examiner

*Primary Examiner* — Thane Underdahl
(74) *Attorney, Agent, or Firm* — Carter, DeLuca & Farrell LLP; George Likourezos

(57) ABSTRACT

The disclosure relates generally to a system, device, and method for cell culturing. In certain embodiments, the system, device, and method may be used to encapsulate single cells in embryo-like, core-shell microcapsules. In some embodiments, microfluidic devices may be utilized to fabricate core-shell hydrogel microcapsules, which may be used to encapsulate individual cells. In some embodiments, the disclosed system and method are utilized to encapsulate cancer stem cells. The disclosed system, device, and method can be used to isolate and culture CSCs, to facilitate the understanding of cancer biology and etiology, and to advance the development of effective CSC-targeted cancer therapies.

31 Claims, 66 Drawing Sheets
Specification includes a Sequence Listing.

FIG. 27B

| Canonical Pathway | 1csc in vitro vs. in vivo |
|---|---|
| Oxidative Phosphorylation | 26.87 |
| Mitochondrial Dysfunction | 26.80 |
| Protein Ubiquitination Pathway | 21.14 |
| EIF2 Signaling | 15.36 |
| Regulation of eIF4 and p70S6K Signaling | 7.96 |
| Nucleotide Excision Repair Pathway | 7.74 |
| tRNA Charging | 7.68 |
| Fatty Acid β-oxidation I | 6.72 |
| Superpathway of Cholesterol Biosynthesis | 5.93 |
| Mitotic Roles of Polo-Like Kinase | 5.74 |
| Assembly of RNA Polymerase II Complex | 5.62 |
| phagosome maturation | 5.43 |
| Hypoxia Signaling in the Cardiovascular System | 4.65 |
| Unfolded protein response | 4.52 |
| Cell Cycle Control of Chromosomal Replication | 4.36 |
| Endoplasmic Reticulum Stress Pathway | 4.35 |
| NRF2-mediated Oxidative Stress Response | 4.33 |
| Superpathway of Methionine Degradation | 4.18 |
| Superpathway of Geranylgeranyldiphosphate Biosynthesis I (via Mevalonate) | 4.16 |
| Mismatch Repair in Eukaryotes | 4.16 |
| Purine Nucleotides De Novo Biosynthesis II | 4.10 |
| Cell Cycle: G2/M DNA Damage Checkpoint Regulation | 4.04 |
| TCA Cycle II (Eukaryotic) | 3.84 |
| 2-oxobutanoate Degradation I | 3.81 |
| Ketolysis | 3.80 |
| mTOR Signaling | 3.71 |
| Mevalonate Pathway I | 3.69 |
| Glutaryl-CoA Degradation | 3.69 |
| Ketogenesis | 3.47 |
| Stearate Biosynthesis I (Animals) | 3.44 |
| Role of CHK Proteins in Cell Cycle Checkpoint Control | 3.25 |
| Ethanol Degradation II | 2.28 |
| Serotonin Degradation | 0.27 |
| Pyrimidine Deoxyribonucleotides De Novo Biosynthesis I | 3.14 |
| Actin Nucleation by ARP-WASP Complex | 3.13 |
| Estrogen Receptor Signaling | 3.11 |
| UDP-N-acetyl-D-glucosamine Biosynthesis II | 3.10 |
| Isoleucine Degradation I | 3.05 |
| Methylmalonyl Pathway | 3.05 |
| Hereditary Breast Cancer Signaling | 2.97 |
| Telomere Extension by Telomerase | 2.79 |
| Polyamine Regulation in Colon Cancer | 2.69 |
| Purine Nucleotides Degradation II (Aerobic) | 2.62 |
| RAN Signaling | 2.56 |
| Guanosine Nucleotides Degradation III | 2.52 |
| Retinol Biosynthesis | 0.56 |
| Tryptophan Degradation III (Eukaryotic) | 2.43 |
| Rapoport-Luebering Glycolytic Shunt | 2.41 |
| ATM Signaling | 2.41 |
| Tumoricidal Function of Hepatic Natural Killer Cells | 2.36 |
| Urate Biosynthesis/Inosine 5'-phosphate Degradation | 2.29 |

FIG. 28

SEQUENCE LISTING

<160> NUMBER OF SEQ ID NOS: 6

<210> SEQ ID NO 1
<211> LENGTH: 317

```
<212> TYPE: PRT
<213> ORGANISM: Homo sapiens

<400> SEQUENCE: 1

Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
            35                  40                  45

Met Val Trp Ser Arg Gly Gln Arg Arg Lys Met Ala Gln Glu Asn Pro
        50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
            115                 120                 125

Gly Gly Leu Leu Ala Pro Gly Gly Asn Ser Met Ala Ser Gly Val Gly
        130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
            195                 200                 205

Ser Met Thr Ser Ser Gln Thr Tyr Met Asn Gly Ser Pro Thr Tyr Ser
        210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
            275                 280                 285

Pro Ser Arg Leu His Met Ser Gln His Tyr Gln Ser Gly Pro Val Pro
        290                 295                 300

Gly Thr Ala Ile Asn Gly Thr Leu Pro Leu Ser His Met
305                 310                 315

<210> SEQ ID NO 2
<211> LENGTH: 360
<212> TYPE: PRT
<213> ORGANISM: Homo sapiens

<400> SEQUENCE: 2

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30
```

```
Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
                100                 105                 110

Glu Pro Cys Thr Val Thr Pro Gly Ala Val Lys Leu Glu Lys Glu Lys
            115                 120                 125

Leu Glu Gln Asn Pro Glu Glu Ser Gln Asp Ile Lys Ala Leu Gln Lys
        130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
                180                 185                 190

Ser Phe Lys Asn Met Cys Lys Leu Arg Pro Leu Leu Gln Lys Trp Val
            195                 200                 205

Glu Glu Ala Asp Asn Asn Glu Asn Leu Gln Glu Ile Cys Lys Ala Glu
        210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
                260                 265                 270

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
        290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
                340                 345                 350

Leu Gly Ser Pro Met His Ser Asn
        355                 360
```

<210> SEQ ID NO 3
<211> LENGTH: 305
<212> TYPE: PRT
<213> ORGANISM: Homo sapiens

<400> SEQUENCE: 3

```
Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45
```

```
Glu Thr Val Ser Pro Leu Pro Ser Ser Met Asp Leu Leu Ile Gln Asp
    50              55              60

Ser Pro Asp Ser Ser Thr Ser Pro Lys Gly Lys Gln Pro Thr Ser Ala
65              70              75              80

Glu Lys Ser Val Ala Lys Lys Glu Asp Lys Val Pro Val Lys Lys Gln
                85              90              95

Lys Thr Arg Thr Val Phe Ser Ser Thr Gln Leu Cys Val Leu Asn Asp
            100             105             110

Arg Phe Gln Arg Gln Lys Tyr Leu Ser Leu Gln Gln Met Gln Glu Leu
        115             120             125

Ser Asn Ile Leu Asn Leu Ser Tyr Lys Gln Val Lys Thr Trp Phe Gln
    130             135             140

Asn Gln Arg Met Lys Ser Lys Arg Trp Gln Lys Asn Asn Trp Pro Lys
145             150             155             160

Asn Ser Asn Gly Val Thr Gln Lys Ala Ser Ala Pro Thr Tyr Pro Ser
            165             170             175

Leu Tyr Ser Ser Tyr His Gln Gly Cys Leu Val Asn Pro Thr Gly Asn
            180             185             190

Leu Pro Met Trp Ser Asn Gln Thr Trp Asn Asn Ser Thr Trp Ser Asn
        195             200             205

Gln Thr Gln Asn Ile Gln Ser Trp Ser Asn His Ser Trp Asn Thr Gln
    210             215             220

Thr Trp Cys Thr Gln Ser Trp Asn Asn Gln Ala Trp Asn Ser Pro Phe
225             230             235             240

Tyr Asn Cys Gly Glu Glu Ser Leu Gln Ser Cys Met Gln Phe Gln Pro
            245             250             255

Asn Ser Pro Ala Ser Asp Leu Glu Ala Ala Leu Glu Ala Ala Gly Glu
            260             265             270

Gly Leu Asn Val Ile Gln Gln Thr Thr Arg Tyr Phe Ser Thr Pro Gln
        275             280             285

Thr Met Asp Leu Phe Leu Asn Tyr Ser Met Asn Met Gln Pro Glu Asp
    290             295             300

Val
305

<210> SEQ ID NO 4
<211> LENGTH: 742
<212> TYPE: PRT
<213> ORGANISM: Homo sapiens

<400> SEQUENCE: 4

Met Asp Lys Phe Trp Trp His Ala Ala Trp Gly Leu Cys Leu Val Pro
1               5               10              15

Leu Ser Leu Ala Gln Ile Asp Leu Asn Ile Thr Cys Arg Phe Ala Gly
            20              25              30

Val Phe His Val Glu Lys Asn Gly Arg Tyr Ser Ile Ser Arg Thr Glu
        35              40              45

Ala Ala Asp Leu Cys Lys Ala Phe Asn Ser Thr Leu Pro Thr Met Ala
    50              55              60

Gln Met Glu Lys Ala Leu Ser Ile Gly Phe Glu Thr Cys Arg Tyr Gly
65              70              75              80

Phe Ile Glu Gly His Val Val Ile Pro Arg Ile His Pro Asn Ser Ile
                85              90              95

Cys Ala Ala Asn Asn Thr Gly Val Tyr Ile Leu Thr Ser Asn Thr Ser
```

-continued

```
            100               105               110

Gln Tyr Asp Thr Tyr Cys Phe Asn Ala Ser Ala Pro Pro Glu Glu Asp
            115               120               125

Cys Thr Ser Val Thr Asp Leu Pro Asn Ala Phe Asp Gly Pro Ile Thr
        130               135               140

Ile Thr Ile Val Asn Arg Asp Gly Thr Arg Tyr Val Gln Lys Gly Glu
145               150               155               160

Tyr Arg Thr Asn Pro Glu Asp Ile Tyr Pro Ser Asn Pro Thr Asp Asp
                165               170               175

Asp Val Ser Ser Gly Ser Ser Ser Glu Arg Ser Ser Thr Ser Gly Gly
            180               185               190

Tyr Ile Phe Tyr Thr Phe Ser Thr Val His Pro Ile Pro Asp Glu Asp
            195               200               205

Ser Pro Trp Ile Thr Asp Ser Thr Asp Arg Ile Pro Ala Thr Thr Leu
        210               215               220

Met Ser Thr Ser Ala Thr Ala Thr Glu Thr Ala Thr Lys Arg Gln Glu
225               230               235               240

Thr Trp Asp Trp Phe Ser Trp Leu Phe Leu Pro Ser Glu Ser Lys Asn
                245               250               255

His Leu His Thr Thr Thr Gln Met Ala Gly Thr Ser Ser Asn Thr Ile
            260               265               270

Ser Ala Gly Trp Glu Pro Asn Glu Glu Asn Glu Asp Glu Arg Asp Arg
            275               280               285

His Leu Ser Phe Ser Gly Ser Gly Ile Asp Asp Asp Glu Asp Phe Ile
            290               295               300

Ser Ser Thr Ile Ser Thr Thr Pro Arg Ala Phe Asp His Thr Lys Gln
305               310               315               320

Asn Gln Asp Trp Thr Gln Trp Asn Pro Ser His Ser Asn Pro Glu Val
                325               330               335

Leu Leu Gln Thr Thr Thr Arg Met Thr Asp Val Asp Arg Asn Gly Thr
            340               345               350

Thr Ala Tyr Glu Gly Asn Trp Asn Pro Glu Ala His Pro Pro Leu Ile
            355               360               365

His His Glu His His Glu Glu Glu Glu Thr Pro His Ser Thr Ser Thr
        370               375               380

Ile Gln Ala Thr Pro Ser Ser Thr Thr Glu Glu Thr Ala Thr Gln Lys
385               390               395               400

Glu Gln Trp Phe Gly Asn Arg Trp His Glu Gly Tyr Arg Gln Thr Pro
                405               410               415

Lys Glu Asp Ser His Ser Thr Thr Gly Thr Ala Ala Ala Ser Ala His
                420               425               430

Thr Ser His Pro Met Gln Gly Arg Thr Thr Pro Ser Pro Glu Asp Ser
            435               440               445

Ser Trp Thr Asp Phe Phe Asn Pro Ile Ser His Pro Met Gly Arg Gly
        450               455               460

His Gln Ala Gly Arg Arg Met Asp Met Asp Ser Ser His Ser Ile Thr
465               470               475               480

Leu Gln Pro Thr Ala Asn Pro Asn Thr Gly Leu Val Glu Asp Leu Asp
                485               490               495

Arg Thr Gly Pro Leu Ser Met Thr Thr Gln Gln Ser Asn Ser Gln Ser
            500               505               510

Phe Ser Thr Ser His Glu Gly Leu Glu Glu Asp Lys Asp His Pro Thr
            515               520               525
```

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
                580                 585                 590

Asp Ser Asn Ser Asn Val Asn Arg Ser Leu Ser Gly Asp Gln Asp Thr
                595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
                660                 665                 670

Arg Arg Arg Cys Gly Gln Lys Lys Lys Leu Val Ile Asn Ser Gly Asn
    675                 680                 685

Gly Ala Val Glu Asp Arg Lys Pro Ser Gly Leu Asn Gly Glu Ala Ser
    690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740

<210> SEQ ID NO 5
<211> LENGTH: 479
<212> TYPE: PRT
<213> ORGANISM: Homo sapiens

<400> SEQUENCE: 5

Met Arg Gln Pro Pro Gly Glu Ser Asp Met Ala Val Ser Asp Ala Leu
1                 5                 10                 15

Leu Pro Ser Phe Ser Thr Phe Ala Ser Gly Pro Ala Gly Arg Glu Lys
                20                 25                 30

Thr Leu Arg Gln Ala Gly Ala Pro Asn Asn Arg Trp Arg Glu Glu Leu
        35                 40                 45

Ser His Met Lys Arg Leu Pro Pro Val Leu Pro Gly Arg Pro Tyr Asp
    50                 55                 60

Leu Ala Ala Ala Thr Val Ala Thr Asp Leu Glu Ser Gly Gly Ala Gly
65                 70                 75                 80

Ala Ala Cys Gly Gly Ser Asn Leu Ala Pro Leu Pro Arg Arg Glu Thr
                85                 90                 95

Glu Glu Phe Asn Asp Leu Leu Asp Leu Asp Phe Ile Leu Ser Asn Ser
                100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro

```
145             150             155             160

Gly Val Ala Pro Gly Gly Thr Gly Gly Gly Leu Leu Tyr Gly Arg Glu
            165             170             175

Ser Ala Pro Pro Pro Thr Ala Pro Phe Asn Leu Ala Asp Ile Asn Asp
            180             185             190

Val Ser Pro Ser Gly Gly Phe Val Ala Glu Leu Leu Arg Pro Glu Leu
            195             200             205

Asp Pro Val Tyr Ile Pro Pro Gln Gln Pro Gln Pro Pro Gly Gly Gly
    210             215             220

Leu Met Gly Lys Phe Val Leu Lys Ala Ser Leu Ser Ala Pro Gly Ser
225             230             235             240

Glu Tyr Gly Ser Pro Ser Val Ile Ser Val Ser Lys Gly Ser Pro Asp
            245             250             255

Gly Ser His Pro Val Val Val Ala Pro Tyr Asn Gly Gly Pro Pro Arg
            260             265             270

Thr Cys Pro Lys Ile Lys Gln Glu Ala Val Ser Ser Cys Thr His Leu
            275             280             285

Gly Ala Gly Pro Pro Leu Ser Asn Gly His Arg Pro Ala Ala His Asp
    290             295             300

Phe Pro Leu Gly Arg Gln Leu Pro Ser Arg Thr Thr Pro Thr Leu Gly
305             310             315             320

Leu Glu Glu Val Leu Ser Ser Arg Asp Cys His Pro Ala Leu Pro Leu
            325             330             335

Pro Pro Gly Phe His Pro His Pro Gly Pro Asn Tyr Pro Ser Phe Leu
            340             345             350

Pro Asp Gln Met Gln Pro Gln Val Pro Pro Leu His Tyr Gln Glu Leu
            355             360             365

Met Pro Pro Gly Ser Cys Met Pro Glu Glu Pro Lys Pro Lys Arg Gly
    370             375             380

Arg Arg Ser Trp Pro Arg Lys Arg Thr Ala Thr His Thr Cys Asp Tyr
385             390             395             400

Ala Gly Cys Gly Lys Thr Tyr Thr Lys Ser Ser His Leu Lys Ala His
            405             410             415

Leu Arg Thr His Thr Gly Glu Lys Pro Tyr His Cys Asp Trp Asp Gly
            420             425             430

Cys Gly Trp Lys Phe Ala Arg Ser Asp Glu Leu Thr Arg His Tyr Arg
            435             440             445

Lys His Thr Gly His Arg Pro Phe Gln Cys Gln Lys Cys Asp Arg Ala
    450             455             460

Phe Ser Arg Ser Asp His Leu Ala Leu His Met Lys Arg His Phe
465             470             475
```

```
<210> SEQ ID NO 6
<211> LENGTH: 865
<212> TYPE: PRT
<213> ORGANISM: Homo sapiens

<400> SEQUENCE: 6

Met Ala Leu Val Leu Gly Ser Leu Leu Leu Leu Gly Leu Cys Gly Asn
1               5               10              15

Ser Phe Ser Gly Gly Gln Pro Ser Ser Thr Asp Ala Pro Lys Ala Trp
            20              25              30

Asn Tyr Glu Leu Pro Ala Thr Asn Tyr Glu Thr Gln Asp Ser His Lys
        35              40              45
```

-continued

```
Ala Gly Pro Ile Gly Ile Leu Phe Glu Leu Val His Ile Phe Leu Tyr
    50              55                  60

Val Val Gln Pro Arg Asp Phe Pro Glu Asp Thr Leu Arg Lys Phe Leu
65              70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
                100                 105                 110

Cys Val Leu Gly Leu Leu Phe Ile Ile Leu Met Pro Leu Val Gly Tyr
            115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
            195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
            245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
    275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
            325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
            355                 360                 365

Asp Arg Val Gln Arg Gln Thr Thr Thr Val Val Ala Gly Ile Lys Arg
    370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
            405                 410                 415

Glu Ser Tyr Ile His Arg Asn Leu Pro Thr Leu Glu Glu Tyr Asp Ser
            420                 425                 430

Tyr Trp Trp Leu Gly Gly Leu Val Ile Cys Ser Leu Leu Thr Leu Ile
            435                 440                 445

Val Ile Phe Tyr Tyr Leu Gly Leu Leu Cys Gly Val Cys Gly Tyr Asp
    450                 455                 460

Arg His Ala Thr Pro Thr Thr Arg Gly Cys Val Ser Asn Thr Gly Gly
```

-continued

```
465                470                475                480

Val Phe Leu Met Val Gly Val Gly Leu Ser Phe Leu Phe Cys Trp Ile
                485                490                495

Leu Met Ile Ile Val Val Leu Thr Phe Val Phe Gly Ala Asn Val Glu
                500                505                510

Lys Leu Ile Cys Glu Pro Tyr Thr Ser Lys Glu Leu Phe Arg Val Leu
                515                520                525

Asp Thr Pro Tyr Leu Leu Asn Glu Asp Trp Glu Tyr Tyr Leu Ser Gly
    530                535                540

Lys Leu Phe Asn Lys Ser Lys Met Lys Leu Thr Phe Glu Gln Val Tyr
545                550                555                560

Ser Asp Cys Lys Lys Asn Arg Gly Thr Tyr Gly Thr Leu His Leu Gln
                565                570                575

Asn Ser Phe Asn Ile Ser Glu His Leu Asn Ile Asn Glu His Thr Gly
                580                585                590

Ser Ile Ser Ser Glu Leu Glu Ser Leu Lys Val Asn Leu Asn Ile Phe
                595                600                605

Leu Leu Gly Ala Ala Gly Arg Lys Asn Leu Gln Asp Phe Ala Ala Cys
    610                615                620

Gly Ile Asp Arg Met Asn Tyr Asp Ser Tyr Leu Ala Gln Thr Gly Lys
625                630                635                640

Ser Pro Ala Gly Val Asn Leu Leu Ser Phe Ala Tyr Asp Leu Glu Ala
                645                650                655

Lys Ala Asn Ser Leu Pro Pro Gly Asn Leu Arg Asn Ser Leu Lys Arg
                660                665                670

Asp Ala Gln Thr Ile Lys Thr Ile His Gln Gln Arg Val Leu Pro Ile
                675                680                685

Glu Gln Ser Leu Ser Thr Leu Tyr Gln Ser Val Lys Ile Leu Gln Arg
    690                695                700

Thr Gly Asn Gly Leu Leu Glu Arg Val Thr Arg Ile Leu Ala Ser Leu
705                710                715                720

Asp Phe Ala Gln Asn Phe Ile Thr Asn Asn Thr Ser Ser Val Ile Ile
                725                730                735

Glu Glu Thr Lys Lys Tyr Gly Arg Thr Ile Ile Gly Tyr Phe Glu His
                740                745                750

Tyr Leu Gln Trp Ile Glu Phe Ser Ile Ser Glu Lys Val Ala Ser Cys
    755                760                765

Lys Pro Val Ala Thr Ala Leu Asp Thr Ala Val Asp Val Phe Leu Cys
770                775                780

Ser Tyr Ile Ile Asp Pro Leu Asn Leu Phe Trp Phe Gly Ile Gly Lys
785                790                795                800

Ala Thr Val Phe Leu Leu Pro Ala Leu Ile Phe Ala Val Lys Leu Ala
                805                810                815

Lys Tyr Tyr Arg Arg Met Asp Ser Glu Asp Val Tyr Asp Asp Val Glu
                820                825                830

Thr Ile Pro Met Lys Asn Met Glu Asn Gly Asn Asn Gly Tyr His Lys
    835                840                845

Asp His Val Tyr Gly Ile His Asn Pro Val Met Thr Ser Pro Ser Gln
    850                855                860

His
865
```

SYSTEM, DEVICE, AND METHOD FOR SINGLE-CELL ENCAPSULATION AND CULTURE

GOVERNMENT SUPPORT

This invention was made with government support under grant No. R01CA206366 NIH awarded by The National Institutes of Health. The government has certain rights in the invention.

CROSS-REFERENCE TO RELATED APPLICATIONS

This application is a national phase of International Application No. PCT/US2021/028503, filed Apr. 21, 2021, which claims priority to U.S. Provisional Application No. 63/013,173 filed on Apr. 21, 2020, which are incorporated by reference herein in their entirety.

SEQUENCE LISTING

The instant application contains a Sequence Listing which has been submitted electronically in ASCII format and is hereby incorporated by reference in its entirety. Said ASCII copy is named 1475-93 PCT US_SEQ.txt and is 26,858 bytes in size.

TECHNOLOGY FIELD

The disclosure relates generally to a system, device, and method for cell culturing. In certain embodiments, the system, device, and method may be used to encapsulate single cells in embryo-like, core-shell microcapsules. In some embodiments, microfluidic devices may be utilized to fabricate core-shell hydrogel microcapsules, which may be used to encapsulate individual cells. In some embodiments, the disclosed system and method are utilized to encapsulate cancer stem cells. The disclosed system, device, and method can be used to isolate and culture CSCs, to facilitate the understanding of cancer biology and etiology, and to advance the development of effective CSC-targeted cancer therapies.

BACKGROUND

There is mounting evidence that suggests a small subset of cancer cells possess the exclusive capability of forming tumors, and these cells are often called cancer stem cells (CSCs) or tumor initiating cells.[1] CSCs have been posited to be responsible for the failure of the widely used chemo and radiotherapies of cancer due to their drug resistance and high capability of tumorigenesis and metastasis, and cancer treatments could be made more effective by targeting and killing the CSCs.[2] Unfortunately, the CSCs are elusive, and their biology are poorly understood up to date. Therefore, establishing a reliable approach to isolate and culture CSCs is invaluable for not only improving our understanding of the CSCs but also developing effective therapeutic strategies for cancer therapy via targeting the CSCs.

"CSCs" have been isolated based on surface markers, such as CD44, CD133, CD24,epithelial cell adhesion molecule (EpCAM), aldehyde dehydrogenase 1 (ALDH1), and ATP-binding cassette B5 (ABCB5).[3] This isolation method often causes confusion. This is because two or more surface makers have been used to identify CSCs from the same type of cancer in different studies, but co-expression of the different surface markers among the selected CSCs is limited.[4] For example, either ALDHI+ or CD44+CD24−/low has been used to select CSCs of breast cancer, but a surprisingly small percentage (0.1-1.2%) of the CSCs express both markers simultaneously.[5] For pancreatic cancer, either CD44+CD24+ESA (epithelial-specific antigen)+ or CD133 has been used to select its CSCs, while only 10-40% of the CD44+/CD24+/ESA+0 cells in primary tumors are shown to be positive for CD133 expression.[6] Similarly, the EpCAM+ CD44+ colorectal CSCs exhibit little overlap with the CD133+ population.[7] In essence, it appears that none of these markers are consistently expressed on the solid tumor CSCs and the specific CSC marker(s) for a given type of cancer is still unknown.

Another widely used method for obtaining "CSCs" is to enrich them with suspension culture in defined CSC medium without serum.[8] Although hanging drops,[9] gyratory rotation and spinner flask,[10] and NASA rotary cell culture systems[11] have been developed to enrich CSCs via suspension culture, ultralow attachment plates (ULAPs) are the most commonly used to enrich CSCs in suspension for various types of cancers.[12] The hypothesis is that only CSCs could survive and form cell aggregates/spheroids, while non-CSCs should die of anoikis during the suspension culture. This method failed to capture CSCs in culture in any sufficient purity. CSCs remain elusive today and it is challenging and confusing to isolate and/or culture them with the contemporary approaches based on surface marker(s) and/or simple suspension culture.

SUMMARY OF EMBODIMENTS

The disclosure provides a composition comprising a one single cell encapsulated within a microparticle, wherein the microparticle comprises a core material enveloped by an outer shell, the core material comprising from about 0.1% to about 10% hyaluronic acid and a hydrogel, and the outer shell comprising a spherical or substantially spherical polyanioic matrix. In some embodiments, the cell is from a primary tumor. In some embodiments, the cell is from a biopsy sample from a primary tumor of breast, colon or brain tissue. In some embodiments, the cell is in culture from about 7 to about 28 days. In some embodiments, the cell is in culture from about 7 to about 10 days. In some embodiments, the cell is in culture from about 21 to about 28 days.

The disclosure further provides a method of culturing a cancer stem cell comprising exposing one single cancer stem cell encapsulated in a microparticle for about 7 days or more in a solid support at about 37 degrees Celsius and about 5% oxygen, wherein the microparticle comprises a core material enveloped by an outer shell, the core material comprising from about 0.1 to about 10% hyaluronic acid and hydrogel, and the outer shell comprising a spherical or substantially spherical polyanioic matrix. In some embodiments, the cell is cultured for about 10 days. In some embodiments, the cell is cultured for about 21 days. In some embodiments, the cell is cultured for about 28 days. In some embodiments, the cell is encapsulated for a time period sufficient to form a spheroid of clonal cells. In some embodiments, the cell is from a primary tumor. In some embodiments, the cell is from a biopsy sample from a primary tumor of breast, colon or brain tissue.

The disclosure also provides a method of isolating a cell comprising exposing a sample of cells to at least one core material, at least one shell material and a hydrophobic agent for a time period sufficient for a cell from the sample to become encapsulated within a microparticle comprising the at least one core material and the at least one shell material, wherein the microparticle comprises the at least one core material enveloped by an outer shell, the core material comprising from about 0.1 to about 10% hyaluronic acid and a hydrogel, and the outer shell comprising a spherical or substantially spherical polyanioic matrix. In some embodiments, the cell is from a primary tumor. In some embodiments, the cell is from a biopsy sample from a primary tumor of breast, colon or brain tissue.

The disclosure additionally provides a method of isolating a single cancer stem cell comprising: (i) exposing a sample of cells to a solid support comprising a probe to CD44 for a time period sufficient to capture a cell that is CD44; (ii) eluting the cell from the probe; and (iii) exposing the cell to a core material and an outer shell for a time period to encapsulate the cell with the core material and the outer shell, wherein the microparticle comprises the core material enveloped by the outer shell, the core material comprising from about 0.1 to about 10% hyaluronic acid and a hydrogel, and the outer shell comprising a spherical or substantially spherical polyanioic matrix. In some embodiments, step (i) further comprises exposing the sample of cells to one or combination of probes of: NANOG, SOX2, OCT4, and KLF4. In some embodiments, the sample is from a primary tumor. In some embodiments, wherein the sample is from a primary breast, brain or colon tumor.

In some embodiments, the hydrogel comprised in any of the disclosed compositions or used in any of the disclosed methods comprises from about 0.1% alginate to about 5.5% alginate. In some embodiments, the outer shell comprised in any of the disclosed compositions or used in any of the disclosed methods is from about 5 to about 500 nanometers in thickness. In some embodiments, the outer shell comprises at least two layers of polyanionic matrix, each layer of polyanionic matrix comprising from about 1% to about 5% of polyanionic material. In some embodiments, the outer shell comprises at least two layers of polyanionic matrix, each layer of polyanionic matrix comprising from about 1% to about 5.5% of polyanionic material positioned around a first layer of polycationic material. In some embodiments, the outer shell comprises at least three layers of hydrogel, a first layer of hydrogel comprising a polyanionic material, a second layer comprising a polycationic material, and a third layer comprising a polyanionic material. In some embodiments, the outer shell comprises at least three layers of hydrogel, the first layer of hydrogel comprises from about 0.1% to about 5.5% alginate, the second layer of hydrogel comprises from about 0.5% to about 5.5% chondroitin or poly- lysine, and the third layer of hydrogel comprises from about 0.1% to 5.5% alginate. In some embodiments, the outer shell is free of a polycationic material. In some embodiments, the outer shell comprises a diameter thickness from about 5 nanometers to about 1 millimeters millimeter. In some embodiments, the outer shell comprises a diameter of thickness from about 10 nanometers to about 500 nanometers. In some embodiments, the outer shell comprises a diameter of thickness from about 10 to about 200 nanometers.

In some embodiments, the core material comprised in any of the disclosed compositions or used in any of the disclosed methods is spherical or substantially spherical in shape and comprises a diameter of from about 5 microns to about 1 millimeter. In some embodiments, the core material comprises a diameter of from about 5 nanometers to about 500 nanometers. In some embodiments, the core material comprises a diameter of from about 10 nanometers to about 200 nanometers in diameter.

In some embodiments, the cell in any of the disclosed compositions or methods is CD44+. In some embodiments, the cell is CD44+ and CD133+. In some embodiments, the cell is CD44+/CD133+/CD24− or expresses CD24 to a limited degree. In some embodiments, the cell is a cancer stem cell. In some embodiments, the cell expresses one or a combination of: NANOG, OCT4, SOX2, KLF4. In some embodiments, the cell expresses CD44, NANOG, OCT4, SOX2 and KLF4. In some embodiments, the cell expresses CD44, NANOG, OCT4,SOX2, KLF4 and CD133. In some embodiments, the cell exhibits mRNA expression for one or a combination of CD44, BMI1, ALDH1A1, ALDH7A1, CXCR4, CXCL3, HGF, DPPA2,HDAC1, HDAC2 and BMPER as measured by RNA sequencing (RNA-seq).

Also provided in the disclosure is a system comprising a solid support comprising at least one composition disclosed herein positioned within a cell culture vessel. In some embodiments, the solid support is a plastic material and comprises from about 1 to about 96 wells, wherein each well comprises contiguous sidewalls that define a volume of from about 1 to about 50 ml. In some embodiments, at least one well comprised in the solid support comprises a cell culture medium. In some embodiments, the cell culture medium is a Dulbecco's Modified Eagle's Medium and Ham's F-12 Nutrient Mixture (DMEM/F12) or Dulbecco's Modified Eagle's Medium and Ham's F-12K (Kaighn's) 12 Nutrient Mixture (DMEM-F12-K). In some embodiments, the cell culture medium comprises the components listed in Table 1.

The disclosure also relates to a device or cassette comprising: (i) an exterior surface; and (ii) an interior surface comprising a microfluidic path defined by at least one inlet and at least one outlet, the at least one inlet positioned at one end of the interior surface accessible by a point exterior to the device and in fluid communication with the least one outlet on the opposite end of the device, the microfluidic path comprising from about 0.1 to about 3.0 inches in length, wherein the microfluidic path comprises a cell isolation segment and a microparticle formation segment, wherein the cell isolation segment comprises a length of microfluic path comprises cellular ligands and the microparticle formation segment comprises a reservoir within which core material and outershell mix with at least one sample.

In some embodiments, the disclosure provides a method of differentiating a cell in culture comprising exposing any of the disclosed composition to one or more differentiation factors. In other embodiments, the disclosure relates to a method of imaging any of the disclosed composition comprising exposing the composition to a fluorescent microscope.

The disclosure further provides a method of producing a colony of cells from one single cancer stem cell comprising exposing any of the disclosed composition to a cell culture medium. In some embodiments, the cell culture medium is a Dulbecco's Modified Eagle's Medium and Ham's F-12 Nutrient Mixture (DMEM/F12) or Dulbecco's Modified Eagle's Medium and Ham's F-12K (Kaighn's) 12 Nutrient Mixture (DMEM-F12-K). In some embodiments, the cell culture medium comprises the components listed in Table 1. In some embodiments, the cell is in culture from about 7 to about 28 days.

BRIEF DESCRIPTION OF THE DRAWINGS

FIG. 1A: A schematic illustration of the one single cell microencapsulation using a nonplanar microfluidic system. Alginate (A) and hyaluronan (HA or H) are used to form the AH core scaffold while the shell is formed with alginate hydrogel. The one single cell is located in the core of the core-shell microcapsule. FIG. 1B: To keep the HA (H) inside the core-shell microcapsules, the outer surface of the alginate (A) shell are coated with chitosan (C) first and then alginate (A) through electrostatic interactions to form an ACA coating on the surface, resulting in the ACA@AH core-shell microcapsules. FIG. 1C: A schematic illustration of the one single cell microencapsulation for isolating and culturing CSCs in defined CSC medium: only the CSCs could survive and proliferate in the 3D AH core scaffold of the miniaturized core-shell microcapsules, while the non-stem cancer cell should die of anoikis. FIG. 1D: Histogram showing the distribution of empty microcapsules and micro-capsules with 1-4 cells after microfluidic encapsulation. We have not seen microcapsules with more than 4 cells under the condition used in this study. FIG. 1E: Typical micro-graphs showing the morphology and growth of one (1) single MDA-MB-231 triple negative human breast cancer cell in the ACA-coated (by default) core-shell microcapsule with HA (H) in the core (ACA@AH-1, or 1csc), multiple MDA-MB-231 cells (10-15 cells per microcapsule) in the ACA-coated core-shell microcapsules with HA in the core (Mcells), conventional suspension culture in ultralow attach-ment plate (Ucells), and 2D culture of MDA-MB-231 cells (2Dcells). FIG. 1F: Approximately 4.4% of the MDA-MB-231 cells could form colonies (note: a cell colony refers specifically to a cell aggregate grown from one cell in this study) under the 1csc (ACA@AH-1) culture. Almost no one single MDA-MB-231 cell could survive in either the core-shell microcapsules without ACA coating but with HA in the core (A@AH-1) or the ACA-coated core-shell microcap-sules without HA in the core (ACA@A-1). However, cell aggregates could be seen in most of the ACA@AH micro-capsules encapsulated with multiple (M) MDA-MB-231 cells (Mcells) after 7 days of culture. MDA-MB-231 cells under the Ucells culture could form loose aggregates in 7 days while the cells under the 2Dcells culture could attach on the 2D substrate and proliferate to ~80-90% confluency in 3 days. FIG. 1G: Serial passaging assay showing more than 50% of the cells in the 1csc colonies could form new generations of colonies under the 1csc culture. The first-passage 1csc (1csc-P1) culture is the same as the 1csc group in FIG. 1E-1F, while 1csc-P2 and 1csc-P3 represent the second-and third-passage 1csc culture using single cells dissociated from the 1csc-P1 and 1csc-P2 colonies, respec-tively.

FIG. 2A: Differential gene expression heat map from RNA-sequencing (RNA-Seq) of cells obtained from the 2Dcells, Ucells, Mcells, and 1csc cultures, showing the gene expression in the 1csc group is largely different from the other three groups. FIG. 2B: Venn diagram for the differential gene expression heat maps of 2Dcells, Ucells, Mcells, and 1csc groups. FIG. 2C: Gene ontology (GO) enrichment analysis of significantly altered genes in cells obtained from the 1csc versus 2Dcells, Ucells, and Mcells cultures. The whole-genome data are represen-tative of three independent experiments. FIG. 2D: Heat map of gene expression in cells of the 2Dcells, Ucells, Mcells, and 1csc groups regarding stemness (including four down-regulated differentiation marker genes), DNA repair, anti-apoptosis, drug resistance, and cell proliferation. FIG. 2E: Confocal images of OCT4, KLF4, SOX2, NANOG, ALDHA1, and AP (alkaline phosphatase) protein expression in cells of the 2Dcells, Ucells, Mcells, and 1csc groups.

DAPI stains the cell nuclei. FIG. 2F: Representative flow cytometry peaks and quantitative analyses of the expression of OCT4, KLF4, SOX2, NANOG, and ALDHA1 proteins in cells of the 2Dcells, Ucells, Mcells, and 1csc groups. The p values for the 1csc group versus the 2Dcells, Ucells, and Mcells groups are <0.0001 for OCT4, <0.0001 for KLF4, 0.0009 for SOX2, <0.0001 for NANOG, and <0.0001 for ALDHA1. Error bars denote mean +s.d., and statistical significance was assessed by one-way ANOVA with post hoc Tukey test. *** $p < 0.001$.

FIG. 3A: A schematic illustra-tion of the protocol for endothelial differentiation and vas-cular tube formation. FIG. 3B: Immunofluorescence staining of human CD31 (hCD31) and ACTIN and DAPI staining of nuclei in cells of the 2Dcells, Ucells, Mcells, and 1csc groups cultured in endothelial growth medium (EGM) supplemented with 50 ng ml-1 of vascular endothelial growth factor (VEGF), together with cells from the 1csc group cultured in CSC medium. DIC: Differential interfer-ence contrast. FIG. 3C: A schematic illustration of the protocol for cardiac differentiation. FIG. 3D-3E: Confocal images showing the expression level of two cardiac specific markers, cardiac troponin I (cTnI, FIG. 3D) and a-ACTININ (FIG. 3E), in cells of the 2Dcells, Ucells, Mcells, and 1csc groups after cardiac differentiation. FIG. 3F: A schematic illustration of the protocol for osteogenic differentiation. FIG. 3G: Typical pictures and microscopic images of the cells stained with Alizarin Red S to visualize calcium deposition after osteogenic differentiation. FIG. 3H: Quan-titative analysis of the absorbance of Alizarin Red S at 500 nm in the cells after osteogenic differentiation of cells from the 2Dcells, Ucells, Mcells, and 1csc groups. The p value for the 1csc group versus 2Dcells, Ucells, and Mcells groups is <0.0001. Statistical significance was assessed by one-way ANOVA with post hoc Tukey test. *** $p < 0.001$. FIG. 3I: A schematic illustration of the protocol for neural differentia-tion together with confocal images showing the expression level of the neuron specific marker MUSASHI-1 (MUS) and the formation of the neurites in the differentiated cells from the four groups. DAPI is for staining the cell nuclei and TUBULIN (TUB) is stained to show the cytoskeleton in cells. Error bars denote mean±s.d.

FIG. 4A: A schematic illustration of the three-generation (G1-G3) in vivo tumorigenesis assay. The G1 tumors were grown from cells obtained by 2Dcells, Ucells, Mcells, and 1csc cultures of the MDA-MB-231 cells; the G2 tumors were grown from cells obtained by 1 csc culture of the four types of G1 tumor cells; and the G3 tumors were grown from cells obtained by 1csc culture of the G2 tumor cells in the four groups. FIG. 4O**: Weight of the 1-1-2D, 1-1-U, and 1-1-M tumors. TF: tumor formation in mice on day 55.

FIG. 5A: A schematic illustration of the protocol of the metastasis assay. Cells from the 2Dcells, Ucells, Mcells, and 1csc cultures are used for injection into mice via their tail vein and the corresponding metastasis study groups are called 2Dmeta, Umeta, Mmeta, and 1meta, respectively. FIG. 5b-5C: Representative photographs of the Bouin solution-fixed lungs (FIG. 5B) and the weight of the lungs (before fixation, FIG. 5C) from the 2Dmeta, Umeta, Mmeta, and 1meta groups. The p value for the 1meta group versus the 2Dmeta, Umeta, and Mmeta groups is 0.0005. Statistical significance was assessed by one-way ANOVA with post hoc Tukey test. * p<0.001. FIG. 5D: Typical images of hematoxylin and eosin (H&E) stained lung tissue from the 2Dmeta, Umeta, Mmeta, and 1meta groups, showing metastasis (arrow) in the lungs of the 1meta group. FIG. 5E: Quantitative analysis of metastatic tumors observed in the H&E images. The p values for the 1meta group versus the 2Dmeta, Umeta, and Mmeta groups is <0.0001 and statistical significance was assessed by one-way ANOVA with post hoc Tukey test. * p <0.001. FIG. 5F: Representative fluorescence images of lung tissues from the 2Dmeta, Umeta, Mmeta, and 1meta groups after immunostaining for human CD44 and Ki67. The human CD44 and Ki67 could be seen only in the 1meta group. Error bars denote mean±s.d.

FIG. 6A-6B: Viability of the cells obtained by 2Dcell, Ucell, Mcell, and 1csc cultures of MDA-MB-231 cells after treating them with doxorubicin hydrochloride (DOX, FIG. 6A) and camptothecin-11 (CPT-11, FIG. 6B). For DOX, the p value for the 1csc group versus the 2Dcells, Ucells, and Mcells groups is <0.0001 for both 10 and 5 µg ml$^{-1}$. For CPT-11, the p value for the 1csc group versus the 2Dcells, Ucells, and Mcells groups is <0.0001 for 50 µg ml$^{-1}$ and it is 0.0034 for 10 µg ml$^{-1}$. Error bars denote mean±s.d., and statistical significance was assessed by one-way ANOVA with post hoc Tukey test.  p<0.01, and * p<0.001. FIG. 6C: Gene Set Enrichment Analysis (GSEA) of the signaling pathways enriched in 1csc colony cells compared with cells from the 2Dcells, Ucells, and Mcells cultures. FIG. 6D: Overall survival via Kaplan-Meier Estimate of patients with enriched core genes in oxidative phosphorylation, mitochondrial dysfunction, EIF2 signaling, MYC targets, DNA repair, and fatty acid metabolism pathways (red line). The blue line shows the survival of patients without enrichment in the respective pathways. Statistical significance was assessed by Kaplan-Meier survival analysis. Error bars denote mean±s.d.

FIG. 8A: FITC-labeled HA is used for the formation of microcapsules, showing that the HA is mainly distributed in the core immediately after microencapsulation. However, most of the HA gradually diffuses out of the microcapsules in 2 days. FIG. 8B: FITC-labeled alginate was used for the last coating step after the chitosan-coating step to make the ACA coating, showing successful formation of the ACA coating on the surface of the microcapsules. To focus on imaging the ACA coating, the core-shell structure of the microcapsules is not as evident in these images. FIG. 8C: Fluorescence images showing the ACA coating can help to retain HA inside the core of the microcapsules for at least for 5 days.

In FIG. 9B, circles of the same color refer to the same cell in different images.

FIG. 10A: Confocal images and quantitative data show more than 90% of the cells are alive after microencapsulation. To focus on the cells, the core-shell structure of the microcapsules is not evident in these images. FIG. 10B: More than 90% of the cells could attach and proliferate after they were released out of the microcapsules using an isotonic solution of sodium citrate and pipetting. FIG. 10C: Proliferation of the encapsulated one single cell based on the area occupied by the cell/colony in the microcapsules determined by using the ImageJ software. FIG. 10D: Differential interference contrast (DIC) images show that the cell colonies are stable even after removing the microcapsule and pipetting for more than 10 times.

FIG. 12A: Percentage of colony formation of PC-3 human prostate cancer cells, MCF-7 human breast cancer cells (HER2$^+$), and OVCAR-8 human ovarian cancer cells formed after the 1csc culture. FIG. 12B: Representative micrographs showing the colony formation from one single cell in the microcapsule core and the growth of the colonies in three weeks for the three different types of cancer cells.

FIG. 18A: Bright field micrographs showing the proliferation of the one single cell isolated from G1 tumors of the 2Dcells, Ucells, Mcells, and 1csc groups under the 1csc culture. Approximately 4% of the tumor cells could form colonies, which is similar to the parent MDA-MB-231 cell line, suggesting that the percentage of CSCs in the in vivo tumors is similar to that in the 2D cultured parent cells. FIG. 18B: Bright field micrographs showing the proliferation of one single cell isolated from G2 tumors of the 2D-1, U-1, M-1, and 1-1 groups under the 1csc culture. Similarly, the percentage of colony formation is ~4% for all the four groups, which is consistent with the results obtained with the G1 tumors. Error bars denote mean±s.d.

FIG. 19A-19B: Tumor image (FIG. 19A) and weight (FIG. 19B) showing that the 1-1, M-1, U-1 and 2D-1 G2 tumors are significantly larger than the 1-U, 1-M, and 1-2D tumors on day 55. This suggests the 1csc colony cells are more tumorigenic than the cells obtained with the 2Dcells, Ucells, and Mcells cultures regardless of the types of G1 tumors. FIG. 19C-19D: Tumor image (FIG. 19C) and weight (FIG. 19D) of G3 tumors showing the cells isolated from the G2 in vivo tumors with the 1csc culture could form larger tumors than the cells isolated from G2 in vivo tumors with the 2Dcells, Ucells, and Mcells cultures. Error bars denote mean +s.d., and n =8 for each group except for M-1 group (n=7), 1-1-1 (n=6), M-1-1 (n=6), U-1-1 (n=6), 2D-1-1 (n=7), and 1-1-2D (n=7) due to animal death. Statistical analyses were performed by one-way ANOVA with post hoc Tukey test. The 1-1, M-1, U-1, or 2D-1 group is compared with the 1-M, 1-U, and 1-2D groups altogether. The 1-1-1, M-1-1, U-1-1, or 2D-1-1 group is compared with the 1-1-M, 1-1-U, and 1-1-2D groups altogether. The symbol & indicates death of animal (note: the survival of animal is not statistically significant between the various groups).

FIG. 27A-27B depict ingenuity pathway analysis (IPA) of the differentially regulated signaling pathways between the 1csc colony cells and cells from 2Dcells, Ucells, and Mcells groups. FIG. 27A: Top 7 differentially expressed stemness-related pathways. The red dashed line indicates the cutoff of the p value (p<0.05) for statistical significance. FIG. 27B: A list of the canonical pathways that are differentially regulated in the 1csc colony cells in comparison to cells from 2Dcells, Ucells, and Mcells groups, showing that the energy metabolism is one of the most significantly altered pathways.

FIG. 28 depicts a list of the canonical pathways, obtained from the IPA analysis, that are differentially expressed in the in vitro 1csc colony cells before injection into mice versus cells in the G1 tumors grown form the in vitro 1csc colony cells by injecting them into the fat pads of mice for 55 days.

DETAILED DESCRIPTION OF EMBODIMENTS

Figure 1A:
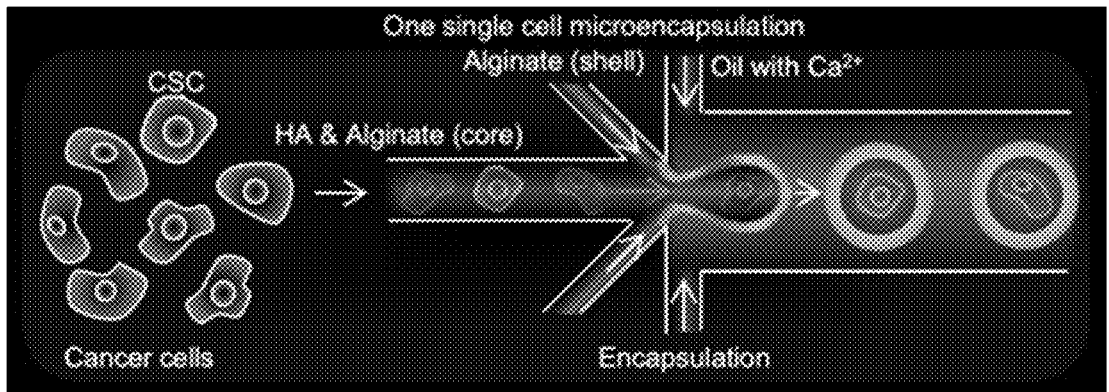
FIG. 1A-1G depict the bioinspired one single cell microencapsulation for isolation and culture of cancer stem cells (CSCs).

Before the present compositions and methods are described, it is to be understood that this invention is not limited to the particular processes, compositions, or methodologies described, as these may vary. It is also to be understood that the terminology used in the description is for the purposes of describing the particular versions or embodiments only, and is not intended to limit the scope of the present disclosure. Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the methods, devices, and materials in some embodiments are now described. All publications mentioned herein are incorporated by reference in their entiretis. Nothing herein is to be construed as an admission that the present disclosure is not entitled to antedate such disclosure by virtue of prior invention.

Definitions

Various terms relating to the methods and other aspects of the present disclosure are used throughout the specification and claims. Such terms are to be given their ordinary meaning in the art unless otherwise indicated. Other specifically defined terms are to be construed in a manner consistent with the definition provided herein.

As used in the specification and the appended claims, the singular forms "a," "an" and "the" can include plural referents unless the context clearly dictates otherwise. Thus, for example, reference to "a compound" includes mixtures of compounds; reference to "a pharmaceutical carrier" includes mixtures of two or more such carriers, and the like.

The term "about" is used herein to mean within the typical ranges of tolerances in the art. For example, "about" can be understood as about 2 standard deviations from the mean. According to certain embodiments, when referring to a measurable value such as an amount and the like, "about" is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value as such variations are appropriate to perform the disclosed methods. When "about" is present before a series of numbers or a range, it is understood that "about" can modify each of the numbers in the series or range.

The term "alginate" is used herein as a collective term and refers to linear polysaccharides formed from β-D-mannuronate and β-L-guluronate in any M/G ratio, as well as salts and derivatives thereof.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "animal" includes, but is not limited to, humans and non-human vertebrates such as wild animals, rodents, such as rats, ferrets, and domesticated animals, and farm animals, such as dogs, cats, horses, pigs, cows, sheep, and goats. In some embodiments, the animal is a mammal. In some embodiments, the animal is a human. In some embodiments, the animal is a non-human mammal.

The term "at least" prior to a number or series of numbers (e.g., "at least two") is understood to include the number adjacent to the term "at least," and all subsequent numbers or integers that could logically be included, as clear from context. When "at least" is present before a series of numbers or a range, it is understood that "at least" can modify each of the numbers in the series or range. Ranges provided herein are understood to include all individual integer values and all subranges within the ranges.

The term "cell" refers to any living cell. The cell may be xenogeneic, autologous, or allogeneic. The cell can be a primary cell obtained directly from a plant or animal, such as a mammal. The cell may also be a cell derived from the culture and expansion of a cell obtained from a plant or animal. For example, the cell may be a stem cell. Immortalized cells are also included within this definition. In some embodiments, the cell has been genetically engineered to express a recombinant protein and/or nucleic acid. In some embodiments, the cell is a stem cell. In some embodiments, the cell is a cancer stem cell.

As used herin, the terms "cancer stem cell" are meant to refers to a stem cell expressing CD44 or a functional fragment thereof. In some embodiments, the cancer stem cell expressed CD44 or a functional fragment thereof, and one or another amino acids of Table Y.

In some embodiments, the cancer stem cell is a cell that expresses SEQ ID NO:1, SEQ ID NO: 2, SEQ ID NO:3, SEQ ID NO:4, SEQ ID NO:5, SEQ ID NO: 6 or a functional fragment thereof that comprises at least about 70%, 75%, 80%, 85%, 90%, 91%, 92%, 93%, 94%, 95%, 96%, 97%, 98%, or 99% identity to any of SEQ ID NO:1, SEQ ID NO:2, SEQ ID NO:3, SEQ ID NO: 4, SEQ ID NO:5, SEQ ID NO: 6 disclosed in Table Y. In some embodiments, the cancer stem cell comprises one or a plurality of molecules of SEQ ID NO:4 or an amino acid that comprises at least about 70%, 75%, 80%, 85%, 90%, 91%, 92%, 93%, 94%, 95%, 96%, 97%, 98%, or 99% sequence identity to SEQ ID NO:4. In some embodiments, the cancer stem cell comprises one or a plurality of molecules of SEQ ID NO: 1 or an amino acid that comprises at least about 70%, 75%, 80%, 85%, 90%, 91%, 92%, 93%, 94%, 95%, 96%, 97%, 98%, or 99% sequence identity to SEQ ID NO: 1. In some embodiments, the cancer stem cell comprises one or a plurality of molecules of SEQ ID NO:2 or an amino acid that comprises at least about 70%, 75%, 80%, 85%, 90%, 91%, 92%, 93%, 94%, 95%, 96%, 97%, 98%, or 99% sequence identity to SEQ ID NO:2. In some embodiments, the cancer stem cell comprises one or a plurality of molecules of SEQ ID NO:3 or an amino acid that comprises at least about 70%, 75%, 80%, 85%, 90%, 91%, 92%, 93%, 94%, 95%, 96%, 97%, 98%, or 99% sequence identity to SEQ ID NO:3. In some embodiments, the cancer stem cell comprises one or a plurality of molecules of SEQ ID NO:5 or an amino acid that comprises at least about 70%, 75%, 80%, 85%, 90%, 91%, 92%, 93%, 94%, 95%, 96%, 97%, 98%, or 99% sequence identity to SEQ ID NO:5. In some embodiments, the cancer stem cell comprises one or a plurality of molecules of SEQ ID NO:6 or an amino acid that comprises at least about 70%, 75%, 80%, 85%, 90%, 91%, 92%, 93%, 94%, 95%, 96%, 97%, 98%, or 99% sequence identity to SEQ ID NO:6.

TABLE Y

| Amino Acid Name | Accession Number | Amino Acid Sequence | | |
|---|---|---|---|---|
| SRY-box transcription factor 2 (SOX2) | P48431 | mynmmetelk | ppgpqqtsgg | gggnstaaaa ggnqknspdr |
| | | vkrpmnafmv | wsrgqrrkma | qenpkmhnse |
| | | iskrlgaewk | llsetekrpf | ideakrlral hmkehpdyky |
| | | rprrktktlm | kkdkytlpgg | llapggnsma sgvgvgaglg |
| | | agvnqrmdsy | ahmngwsngs | ysmmqddqlgy |
| | | pqhpglnahg | aaqmqpmhry | dvsalqynsm tssqtymngs |
| | | ptysmsysqq | gtpgmalgsm | gsvvkseass sppvvtsssh |
| | | srapcqagdl | rdmismylpg | aevpepaaps rlhmsqhyqs |
| | | gpvpgtaing | tlplshm | |
| | | SEQ ID NO: 1 | | |
| Octamer-binding protein 4 (OCT4) | Q01860.1 | maghlasdfa | fspppggggd | gpggpepgwv |
| | | dprtwlsfqg | ppggpgigpg | vgpgsevwgi |
| | | ppcpppyefc | ggmaycgpqv | gvglvpqggl |
| | | etsqpegeag | vgvesnsdga | spepctvtpg avklekekle |
| | | qnpeesqdik | alqkeleqfa | kllkqkritl gytqadvglt |
| | | lgvlfgkvfs | qtticrfeal | qlsfknmckl rpllqkwvee |
| | | adnnenlqei | ckaetlvqar | krkrtsienr vrgnlenlfl |
| | | qcpkptlqqi | shiaqqigle | kdvvrvwfcn rrqkgkrsss |
| | | dyaqredfea | agspfsggpv | sfplapgphf gtpgygsphf |
| | | talyssvpfp | egeafppvsv | ttlgspmhsn |
| | | SEQ ID NO: 2 | | |
| NANOG | NP_079141 | msvdpacpqs | lpcfeasdck | esspmpvicg |
| | | peenypslqm | ssaemphtet | vsplpssmdl liqdspdsst |
| | | spkgkqptsa | eksvakkedk | vpvkkqktrt vfsstqlcvl |
| | | ndrfqrqkyl | slqqmqelsn | ilnlsykqvk twfqnqrmks |
| | | krwqknnwpk | nsngvtqkas | aptypslyss yhqgclvnpt |
| | | gnlpmwsnqt | wnnstwsnqt | qniqswsnhs |
| | | wntqtwctqs | wnnqawnspf | yncgeeslqs |
| | | cmqfqpnspa | sdleaaleaa | geglnviqqt tryfstpqtm |
| | | dlflnysmnm | qpedv | |
| | | SEQ ID NO: 3 | | |
| CD44 | NP_000601 | mdkfwwhaaw | glclvplsla | qidlnitcrf agvfhvekng |
| | | rysisrteaa | dlckafnstl | ptmaqmekal sigfetcryg |
| | | fieghvvipr | ihpnsicaan | ntgvyiltsn tsqydtycfn |

TABLE Y-continued

| Amino Acid Name | Accession Number | Amino Acid Sequence |
|---|---|---|
| | | asappeedct svtdlpnafd gpititivnr dgtryvqkge<br>yrtnpediyp snptdddvss gsssserssts ggyifytfst<br>vhpipdedsp witdstdrip attlmstsat atetatkrqe<br>twdwfswlfl psesknhlht ttqmagtssn tisagwepne<br>enederdrhl sfsgsgiddd edfisstist tprafdhtkq<br>nqdwtqwnps hsnpevllqt ttrmtdvdrn gttayegnwn<br>peahpplihh ehheeeetph ststiqatps stteetatqk<br>eqwfgnrwhe gyrqtpkeds hsttgtaaas ahtshpmqgr<br>ttpspedssw tdffnpishp mgrghqagrr mdmdsshsit<br>lqptanpntg lvedldrtgp lsmttqqsns qsfstshegl<br>eedkdhptts tltssnrndv tggrrdpnhs egsttllegy<br>tshyphtkes rtfipvtsak tgsfgvtavt vgdsnsnvnr<br>slsgdqdtfh psggshtthg sesdghshgs qegganttsg<br>pirtpqipew liilasllal alilavciav nsrrregqkk<br>klvinsgnga vedrkpsgln geasksqemv hlvnkesset<br>pdqfmtadet rnlqnvdmki gv<br>SEQ ID NO: 4 |
| Krueppel-like factor 4 (KLF4) | NP_004226 | mrqppgesdm avsdallpsf stfasgpagr ektlrqagap<br>nnrwreelsh mkrlppvlpg rpydlaaatv atdlesggag<br>aacggsnlap lprreteefn dlldldfils nslthppesv<br>aatvsssasa ssssspssssg pasapstcsf typiragndp<br>gvapggtggg llygresapp ptapfnladi ndvspsggfv<br>aellrpeldp vyippqqpqp pgglmgkfv lkaslsapgs<br>eygspsvisv skgspdgshp vvvapynggp prtcpkikqe<br>avsscthlga gpplsnghrp aahdfplgrq lpsrttptlg<br>leevlssrdc hpalplppgf hphpgpnyps flpdqmqpqv<br>pplhyqelmp pgscmpeepk pkrgrrswpr krtathtcdy<br>agcgktytks shlkahlrth tgekpyhcdw dgcgwkfars<br>deltrhyrkh tghrpfqcqk cdrafsrsdh lalhmkrhf<br>SEQ ID NO: 5 |
| CD133 | NP_006008 | malvlgslll lglcgnsfsg gqpsstdapk awnyelpatn<br>yetqdshkag pigilfelvh iflyvvqprd fpedtlrkfl<br>qkayeskidy dkpetvilgl kivyyeagii lccvlgllfi<br>ilmplvgyff cmcrccnkcg gemhqrqken gpflrkcfai<br>sllviciiis igifygfvan hqvrtrikrs rkladsnfkd<br>lrtllnetpe qikyilaqyn ttkdkaftdl nsinsvlggg<br>ildrlrpnii pvldeiksma taiketkeal enmnstlksl<br>hqqstqlsss ltsvktslrs slndplclvh pssetcnsir<br>lslsqlnsnp elrqlppvda eldnvnnvlr tdldglvqqg<br>yqslndipdr vqrqtttvva gikrvlnsig sdidnvtqrl<br>piqdilsafs vyvnntesyi hrnlptleey dsywwlgglv<br>icslltlivi fyylgllcgv cgydrhatpt trgcvsntgg<br>vflmvgvgls flfcwilmii vvltfvfgan veklicepyt<br>skelfrvldt pyllnedwey ylsgklfnks kmkltfeqvy<br>sdckknrgty gtlhlqnsfn isehlnineh tgsisseles<br>lkvnlnifll gaagrkniqd faacgidrmn ydsylaqtgk<br>spagvnllsf aydleakans lppgnlrnsl krdaqtikti<br>hqqrvlpieq slstlyqsvk ilqrtgngll ervtrilasl<br>dfaqnfitnn tssviieetk kygrtiigyf ehylqwiefs<br>isekvasckp vataldtavd vflcsyiidp lnlfwfgigk<br>atvfllpali favklakyyr rmdsedvydd vetipmknme<br>ngnngyhkdh vygihnpvmt spsqh<br>SEQ ID NO: 6 |

As used in the specification and in the claims, the term "comprising" can include the aspects "consisting of" and "consisting essentially of." Comprising can also mean "including but not limited to."

The term "exposing" as used herein refers to bringing a disclosed compound and a cell, target receptor, or other biological entity together in contact such that the compound can affect the activity of the cell (e.g., receptor, cell, etc.), either directly (i.e., by interacting with the target or cell itself) or indirectly (i.e., by interacting with another molecule, such as co-factor, factor, or protein on which the activity of the cell is dependent). In some embodiments, the activity of cell is differentiation. In some embodiments, the compound is one or more differentiation factors.

The term "hydrogel" refers to a substance formed when an organic polymer (natural or synthetic) is cross-linked via covalent, ionic, or hydrogen bonds to create a three-dimensional open-lattice structure which entraps water molecules to form a gel. Biocompatible hydrogel refers to a polymer that forms a gel which is not toxic to living cells, and allows sufficient diffusion of oxygen and nutrients to the entrapped cells to maintain viability. The term "hydrogel matrix" as used herein is defined as any three-dimensional hydrogel construct, system, device, or similar structure. In some embodiments, the hydrogel or hydrogel matrix comprises one or more proteins and/or glycoproteins. In some embodiments, the hydrogel or hydrogel matrix comprises one or more of the following proteins: collagen, gelatin, elastin, titin, laminin, fibronectin, fibrin, keratin, silk fibroin, and any derivatives or combinations thereof. In some embodiments, the hydrogel or hydrogel matrix comprises Matrigel® or vitronectin. In some embodiments, the hydrogel or hydrogel matrix can be solidified into various shapes. In some embodiments, the hydrogel or hydrogel matrix comprises poly (ethylene glycol) dimethacrylate (PEG). In some embodiments, the hydrogel or hydrogel matrix comprises Puramatrix. In some embodiments, the hydrogel or hydrogel matrix comprises glycidyl methacrylate-dextran (MeDex). In some embodiments, two or more hydrogels or hydrogel matrixes are used simultaneously in a cell culture vessel. In some embodiments, two or more hydrogels or hydrogel matrixes are used simultaneously in the same cell culture vessel but the hydrogels are separated by a wall that create independently addressable microenvironments in the tissue culture vessel such as wells. In a multiplexed tissue culture vessel, it is possible for some embodiments to include any number of aforementioned wells or independently address-able location within the cell culture vessel such that a hydrogel matrix in one well or location is different or the same as the hydrogel matrix in another well or location of the cell culture vessel.

As used herein, the term "inhibition," "inhibit," "inhibit-ing," and the like in reference to a protein-inhibitor (e.g., antagonist) interaction means negatively affecting (e.g., decreasing) the activity or function of the protein relative to the activity or function of the protein in the absence of the inhibitor. In some embodiments, inhibition refers to reduc-tion of a disease or symptoms of disease. In some embodi-ments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

As used herein, the term "mammal" means any animal in the class Mammalia such as rodent (i.e., mouse, rat, or guinea pig), monkey, cat, dog, cow, horse, pig, or human. In some embodiments, the mammal is a human. In some embodiments, the mammal refers to any non- human mam-mal. The present disclosure relates to any of the methods or compositions of matter wherein the sample is taken from a mammal or non-human mammal.

The term "Matrigel®" means a solubilized basement membrane preparation extracted from the Engelbreth-Holm-Swarm (EHS) mouse sarcoma comprising ECM proteins including laminin, collagen IV, heparin sulfate proteogly-cans, entactin/nidogen, and other growth factors. In some embodiments, Cultrex® BME (Trevigen, Inc.) or Geltrex® (Thermo-Fisher Inc.) may be substituted for Matrigel®.

As used herein, the term "microcapsule" refers to a particle or capsule having a mean diameter of from about 50 μm to about 1000 μm, formed of a cross-linked hydrogel shell surrounding a core. In some embodiments, the core comprises a biocompatible matrix. In Some embodiments the microcapsule may have any shape suitable for cell encapsulation such as a spheroid, sphere or substantially spherical shape. The microcapsule may contain one or more cells dispersed in the biocompatible matrix, cross-linked hydrogel, or combination thereof, thereby "encapsulating" the cells. In some embodiments, the microcapsule contains one cell. In some embodiments, the microcapsule contains one cancer stem cell. In some embodiments, the microcap-sule comprises a colony of cells configured in a spheroid and derived from one, single cell. In some embodiments, the microcapsule contains one colony that is a spheroid grown from one, single cancer stem cell.

The term "microfluidic device" refers to a device that comprises one or more microfluidic channels, one or more microfluidic valves, one or more microfluidic chambers, or combinations thereof. In some embodiments, the microflu-idic device comprises one or more microfluidic channels that are configured to carry, store, transport, combine, and/or react component solutions in fluid volumes of less than about 200, 100, 10 and/or 1 milliliters. In some embodi-ments, the microfluidic device is useful to form microcap-sulated cells. In some embodiments, the microfluidic device is configured to carry, store, transport, combine, and/or react component solutions in fluid volumes of about 5 mL or less. In some embodiments, the microfluidic device is configured to carry, store, transport, combine, and/or react component solutions in fluid volumes of about 2.5 mL or less. In some embodiments, the microfluidic device is configured to carry, store, transport, combine, and/or react component solutions in fluid volumes of about 1.0 mL or less) to form micro-capsules or microencapsulated cells.

"Microfluidic channel" as used herein refers to a feature within a microfluidic device that forms a path, such as a conduit, through which one or more fluids can flow. In some embodiments, microfluidic channels have at least one cross-sectional dimension that is in the range from about 0.1 microns to about 750 microns. In some embodiments, microfluidic channels have at least one cross-sectional dimension from about 1 micron to about 750 microns. In some embodiments, microfluidic channels have at least one cross-sectional dimension from about 1 micron to about 500 microns. In some embodiments, microfluidic channels have at least one cross-sectional dimension that is from about 10 microns to about 500 microns. In some embodiments, microfluidic channels have at least one cross-sectional dimension from about 50 microns to about 450 microns. "Optional" or "optionally" means that the subsequently described event, circumstance, or material may or may not occur or be present, and that the description includes instances where the event, circumstance, or material occurs or is present and instances where it does not occur or is not present.

The word "or" as used herein means any one member of a particular list and also includes any combination of mem-bers of that list.

Any probes may be used in concert with any of the devices, kits, or methods disclosed herein. As used herein, the term "probe" refers to any molecule that may bind or associate, indirectly or directly, covalently or non-cova-lently, to any of amino acid sequences that are expressed on the cells disclosed, particularly the cells within the micro-encapsulation. In some embodiments, the probe is a fluoro-genic probe, antibody or absorbance-based probes. If an absorbance-based probe, the chromophore pNA (para-nitro-analine) may be used as a probe for detection and/or quantification of a protease disclosed herein.

As used herein, the terms "fluorogenic probe" refers to any molecule (dye, peptide, or fluorescent marker) that emits a known and/or detectable wavelength of light upon expo-sure to a known wavelength of light. In some embodiments, peptides expressed on the surface of the disclosed cells are covalently or non-covalently attached to a fluorogenic probe. In some embodiments, the attachment of the fluoro-genic probe to the substrate creates a chimeric molecule capable of a fluorescent emission or emissions upon expo-sure of the labeled peptides expressed on the surface of the disclosed cells the known wavelength of light, such that exposure to the peptide is quantifiable in the presence of a fluorimeter. In some embodiments, the fluorogenic probe is fully quenched upon exposure to the known wavelength of light before the fluorogenic probe emits a known wavelength of light the intensity of which is quantifiable by absorbance readings or intensity levels in the presence of a fluorimeter and after association of the probe and peptides expressed on the surface of the disclosed cells. In some embodiments, the fluorogenic probe is a coumarin-based dye or rhodamine-based dye with fluorescent emission spectra measurable or quantifiable in the presence of or exposure to a predetermined wavelength of light. In some embodiments, the fluorogenic probe comprises rhodamine. In some embodiments, the fluorogenic probe comprises rhodamine-100. Coumarin-based fluorogenic probes are known in the art, for example in a U.S. Pat. No. 7,625,758 and 7,863,048, which are herein incorporated by reference in their entireties. In some embodiments, the fluorogenic probes are a component to, covalently bound to, non-covalently bound to, intercalated with one or a plurality of substrates to any of the cells or amini acid sequences expressed by the cells disclosed herein. In some embodiments, the fluorogenic probes are chosen from ACC or AMC. In some embodiments, the fluorogenic probe is a fluorescein molecule. In some embodiments, the fluorogenic probe is capable of emitting a resonance wave detectable and/or quantifiable by a fluorimeter after exposure to one or a plurality of cells or amino acid sequences expressed by the cells disclosed herein.

The term "preventing" or "prevention" or "prevent" as used herein refers to prophylactic or preventative measures that prevent or slow the development of a targeted pathologic condition or disorder. Those in need of treatment include those already diagnosed with the disorder; those prone to have the disorder; and those in whom the disorder is to be prevented.

As used herein, a "spheroid" or "cell spheroid" means any grouping of cells in a three- dimensional shape that generally corresponds to an oval or circle rotated about one of its principal axes, major or minor, and includes three-dimensional egg shapes, oblate and prolate spheroids, spheres, and substantially equivalent shapes.

The term "subject" as used herein refers to any animal (e.g., a mammal), including, but not limited to, humans, non-human primates, canines, felines, rodents, and the like. Preferably, the subject is a human subject. The terms "subject," "individual," and "patient" are used interchangeably herein. The terms "subject," "individual," and "patient" thus encompass individuals having cancer (e.g., breast cancer), including those who have undergone or are candidates for resection (surgery) to remove cancerous tissue.

The term "two-dimensional culture" as used herein is defined as cultures of cells on flat hydrogels, including Matrigel® and vitronectin, disposed in culture vessels.

Generally speaking, the term "tissue" refers to any aggregation of similarly specialized cells which are united in the performance of a particular function.

The term "bioreactor" refers to an enclosure or partial enclosure in which cells are cultured, optionally in suspension. In some embodiments, the bioreactor refers to an enclosure or partial enclosure in which cells are cultured where said cells may be in liquid suspension, or alternatively may be growing in contact with, on, or within another non-liquid substrate including but not limited to a solid growth support material. In some embodiments, the solid growth support material, or solid substrate, comprises at least one or a combination of: silica, plastic, metal, hydrocarbon, or gel. The disclosure relates to a system comprising a bioreactor comprising one or a plurality of culture vessels into which neuronal cells may be cultured in the presence or cellular growth media.

The term "culture vessel" as used herein can be any vessel suitable for growing, culturing, cultivating, proliferating, propagating, or otherwise similarly manipulating cells. A culture vessel may also be referred to herein as a "culture insert". In some embodiments, the culture vessel is made out of biocompatible plastic and/or glass. In some embodiments, the plastic is a thin layer of plastic comprising one or a plurality of pores that allow diffusion of protein, nucleic acid, nutrients (such as heavy metals and hormones) antibiotics, and other cell culture medium components through the pores. In some embodiments, the pores are not more than about 0.1, 0.5 1.0, 2, 3, 4, 5, 6, 7, 8, 9, 10, 15, 20, 25, 30, 40, 50 microns wide. In some embodiments, the culture vessel in a hydrogel matrix and free of a base or any other structure. In some embodiments, the culture vessel is designed to contain a hydrogel or hydrogel matrix and various culture mediums. In some embodiments, the culture vessel consists of or consists essentially of a hydrogel or hydrogel matrix. In some embodiments, the only plastic component of the culture vessel is the components of the culture vessel that make up the side walls and/or bottom of the culture vessel that separate the volume of a well or zone of cellular growth from a point exterior to the culture vessel. In some embodiments, the culture vessel comprises a hydrogel and one or a plurality of isolated glial cells. In some embodiments, the culture vessel comprises a hydrogel and one or a plurality of isolated glial cells, to which one or a plurality of neuronal cells are seeded. In some embodiments, the methods relate to a method of manufacturing a system. culture plate or device for culturing cells, the method comprising obtaining a stem cell, such as a induce pluripotent stem cell, exposing the cell to one or plurality of cellular growth factors, differentiating the stem cells into a differentiated cell disclosed in the Examples, and seeding the cell into a solid substrate comprising a first and/or second cavity or well. In some embodiments, the first and/or second cavity is a U bottom well, a curved-bottom well or flat-bottom well. In some embodiments, the method comprises seeding about 10, 15, 20, 25, 30, 35, 40, 45, 50, 55, 60, 65, 70, 75, 80, 90, 100, 125, 150, 175, 200, 225 or 250 thousand cells. In some embodiments, the step of seeding the cells comprises seeding one or a plurality of cells in a series of cavities or wells separated within a solid substrate and each cavity or well comprising cell culture medium. In some embodiments, the step of seeding the cavities or wells comprises seeding the cells in a pattern positioned within the solid substrate such that each well comprises a spheroid of cells and each spheroid is grown in a suspension or hanging drop format. In some embodiments, the method of manufacturing a system, culture plate or device for culturing cells comprises allowing the cells to culture undisturbed for sufficient time for the cells to spontaneously form one or a plurality of spheroids.

The term "functional fragment" can be any portion of a polypeptide or nucleic acid sequence from which the respective full-length polypeptide or nucleic acid relates that is of a sufficient length and has a sufficient structure to confer a biological affect that is at least similar or substantially similar to the full-length polypeptide or nucleic acid upon which the fragment is based. In some embodiments, a functional fragment is a portion of a full-length or wild-type nucleic acid sequence that encodes any one of the nucleic acid sequences disclosed herein, and said portion encodes a polypeptide of a certain length and/or structure that is less than full-length but encodes a domain that still biologically functional as compared to the full-length or wild-type protein. In some embodiments, the functional fragment may have a reduced biological activity, about equivalent biological activity, or an enhanced biological activity as compared to the wild-type or full-length polypeptide sequence upon which the fragment is based. In some embodiments, the functional fragment is derived from the sequence of an organism, such as a human. In such embodiments, the functional fragment may retain 99%, 98%, 97%, 96%, 95%, 94%, 93%, 92%, 91%, or 90% sequence identity to the wild-type human sequence upon which the sequence is derived. In some embodiments, the functional fragment may retain 87%, 85%, 80%, 75%, 70%, 65%, or 60% sequence identity to the wild-type sequence upon which the sequence is derived (such as SEQ ID NO: 1, 2, 3, 4, 5, or 6).

The term "three-dimensional" or "3D" as used herein means, for example, a thickness of culture of cells such that there are at least three layers of cells growing adjacent to one another. In some embodiments, the term three-dimensional means that, in context of the disclosed systems, the neurites and/or axons are from about 10 to about 1000 microns in thickness or height. In some embodiments, the term three-dimensional means that, in context of the disclosed systems, the neurites and/or axons are from about 10 to about 100 microns in thickness or height.

The term "plastic" refers to biocompatible polymers comprising hydrocarbons. In some embodiments, the plastic is selected from the group consisting of: Polystyrene (PS), Poly acrylo nitrile (PAN), Poly carbonate (PC), polyvinylpyrrolidone, polybutadiene (PVP), Polyvinyl butyral (PVB), Poly vinyl chloride (PVC), Poly vinyl methyl ether (PVME), poly lactic-co-glycolic acid (PLGA), poly (l-lactic acid), polyester, polycaprolactone (PCL), poly ethylene oxide (PEO), polyaniline (PANI), polyflourenes, polypyrroles (PPY), poly ethylene dioxythiophene (PEDOT), and a mixture of two or any two or more of the foregoing polymers. In some embodiments, the plastic is a mixture of three, four, five, six, seven, eight or more polymers.

The term "seeding" as used herein refers to, for example, transferring an amount of cells into a new culture vessel. The amount may be defined and may use volume or number of cells as the basis of the defined amount. The cells may be part of a suspension.

The terms "sequence identity" as used herein refers to, in the context of two or more nucleic acids or polypeptide sequences, the specified percentage of residues that are the same over a specified region. The term is synonymous with "sequence homology" or sequences being "homologous to" another sequence. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

The term "solid substrate" as used herein refers to any substance that is a solid support that is free of or substantially free of cellular toxins. In some embodiments, the solid substrate comprise one or a combination of silica, plastic, and metal. In some embodiments, the solid substrate comprises pores of a size and shape sufficient to allow diffusion or non-active transport of proteins, nutrients, and gas through the solid substrate in the presence of a cell culture medium. In some embodiments, the pore size is no more than about 10, 9, 8, 7, 6, 5, 4, 3, 2 or 1 micron in diameter. One of ordinary skill could determine how big of a pore size is necessary based upon the contents of the cell culture medium and exposure of cells growing on the solid substrate in a particular microenvironment. For instance, one of ordinary skill in the art can observe whether any cultured cells in the system or device are viable under conditions with a solid substrate comprises pores of various diameters. In some embodiments, the solid substrate comprises a base with a predetermined shape that defines the shape of the exterior and interior surface. In some embodiments, the base comprises one or a combination of silica, plastic, ceramic, or metal and wherein the base is in a shape of a cylinder or in a shape substantially similar to a cylinder.

A spheroid of the present invention can have any suitable width, length, thickness, and/or diameter. In some embodiments, a spheroid may have a width, length, thickness, and/or diameter in a range from about 10 μm to about 50,000 μm, or any range therein, such as, but not limited to, from about 10 μm to about 900 μm, about 100 μm to about 700 μm, about 300 μm to about 600μm, about 400 μm to about 500 μm, about 500 μm to about 1,000 μm, about 600 μm to about 1,000μm, about 700 μm to about 1,000 μm, about 800 μm to about 1,000 μm, about 900 μm to about 1,000 μm, about 750 μm to about 1,500 μm, about 1,000 μm to about 5,000 μm, about 1,000 μmto about 10,000 μm, about 2,000 to about 50,000 μm, about 25,000 μm to about 40,000 μm, or about 3,000 μm to about 15,000 μm. In some embodiments, a spheroid may have a width, length, thickness, and/or diameter of about 50 μm, 100 μm, 200 μm, 300 μm, 400 μm, 500 μm, 600 μm, 700 μm, 800 μm, 900 μm, 1,000 μm, 5,000 μm, 10,000 82 m, 20,000 μm, 30,000 μm, 40,000 μm, or 50,000 μm. In some embodiments, a plurality of spheroids are generated, and each of the spheroids of the plurality may have a width, length, thickness, and/or diameter that varies by less than about 20%, such as, for example, less than about 15%, 10%, or 5%. In some embodiments, each of the spheroids of the plurality may have a different width, length, thickness, and/or diameter within any of the ranges set forth above.

The cells in a spheroid may have a particular orientation. In some embodiments, the spheroid may comprise an interior core and an exterior surface. In some embodiments, the spheroid may be hollow (i.e., may not comprise cells in the interior). In some embodiments, the interior core cells and the exterior surface cells are different types of cell. In some embodiments, the interior core comprises a magnetic nanoparticle.

The spheroids may vary in their stiffness, e.g., as measured by elastic modulus (Pascals; Pa). In certain embodiments, the elastic moduli of the spheroids are in a range from about 100 Pa to about 10,000 Pa, e.g., from about 100 Pa to about 12,000 Pa or from about 100 Pa to about 4800 Pa. In some embodiments, the elastic moduli of the spheroids may be about 1200 Pa. As another example, the spheroid modulus may vary from about at least 10 Pa, at least about 100 Pa., at least about 150 Pa, at least about 200 Pa, or at least about 450 Pa. In some embodiments, the composition or device of the disclosure comprises one or a plurality of wells and each well comprises one or a plurality of different spheroids, a first, second, third, fourth or fifth or more population of spheroids. In one embodiment, the first spheroid comprises an elastic modulus from about 100 Pa to about 300 Pa, and the second spheroid comprises an elastic modulus from about 400 Pa to about 800 Pa. In another example, the first spheroid is characterized by an elastic modulus from about 50 to about 200 Pa, and a second spheroid is characterized by an elastic modulus from about 250 Pa to about 500 Pa.

In some embodiments, spheroids may be made up of one, two, three or more different cell types, including one or a plurality of cancer cell types and/or one or a plurality of stem cell types. In some embodiments, the interior core cells may be made up of one, two, three, or more different cell types. In some embodiments, the exterior surface cells may be made up of one, two, three, or more different cell types. In some embodiments, the disclosure relates to a spheroid comprising a cancer stem cell and its progeny. In some embodiments, the spheroid is one cell type or a cluster of cells clonally derived from one single cancer stem cell.

Compositions

The disclosure relates to compositions comprising a one single cell encapsulated within a microparticle. Such single-cell encapsulated microparticles are also referred to as microencapsulated cells. The disclosed microparticle contains a core surrounded by an outer shell (core-shell microparticles) produced in a single step via a mild process that ensures high immediate cell viability. The core contains a one single cell suspended or encapsulated in a matrix. For example, the matrix can be a viscous aqueous liquid or a hydrogel. In some embodiments, the matrix forming the core is a viscous aqueous liquid or solution. In some embodiments, the matrix forming the core is a hydrogel. In some embodiments, the core is spherical or substantially spherical in shape. In some embodiments, the matrix forming the core contains proteins suitable for promoting a cell activity, such as survival, attachment, growth, pluripotency, or differentiation. For example, the protein can be collagen, fibrin, gelatin, elastin, or elastin-like polypeptides (ELPs), or a derivative thereof.

In some embodiments, the outer shell comprises a spherical or substantially spherical polyanioic matrix. In some embodiments, the outer shell surrounding the core is a hydrogel. In some embodiments, the outer shell comprises at least two layers of polyanionic matrix, each layer of polyanionic matrix comprising from about 0.5% to about 10% of polyanionic material. In some embodiments, the outer shell comprises at least two layers of polyanionic matrix, each layer of polyanionic matrix comprising from about 1% to about 5% of polyanionic material. In some embodiments, the outer shell comprises at least two layers of polyanionic matrix, each layer of polyanionic matrix comprising from about 1% to about 5.5% of polyanionic material positioned around a first layer of polycationic material. In some embodiments, the outer shell comprises at least three layers of hydrogel, a first layer of hydrogel comprising a polyanionic material, a second layer comprising a polycationic material, and a third layer comprising a polyanionic material. In some embodiments, the outer shell comprises at least two layers of hydrogel, at least one layer of hydrogel comprises alginate. In some embodiments, the outer shell comprises at least three layers of hydrogel, at least one layer of hydrogel comprises alginate. In some embodiments, the outer shell is free of a polycationic material.

Examples of materials which can be used to form a suitable hydrogel (e.g., in the core, outer shell, or combinations thereof) include polysaccharides such as alginate, polyphosphazines, poly (acrylic acids), poly (methacrylic acids), poly (alkylene oxides), poly (vinyl acetate), poly (acrylamides) such as poly (N-isopropylacrylamide), poly-vinylpyrrolidone (PVP), and copolymers and blends of each. See, for example, U.S. Pat. Nos. 5,709,854, 6,129,761 and 6,858,229, each incorporated by reference herein. In some embodiments, block copolymers can be used. For example, poloxamers containing a hydrophobic poly (alkylene oxide) segment (i.e., polypropylene oxide) and hydrophilic poly (alkylene oxide) segment (i.e., polyethylene oxide) can be used. Polymers of this type are available are known in the art, and commercially available under the trade name PLURONICS from BASF. In some embodiments, the material is selected such that it forms a thermally responsive hydrogel.

In general, the polymers used to form the core and outer shell are at least partially soluble in aqueous solutions, such as water, buffered salt solutions, or aqueous alcohol solutions. In some embodiments, the polymers have polar groups, charged groups, acidic groups or salts thereof, basic groups or salts thereof, or combinations thereof. Examples of polymers with acidic groups poly (phosphazencs), poly (acrylic acids), poly (methacrylic acids), poly (vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups include carboxylic acid groups and sulfonic acid groups.

Examples of polymers with basic groups include poly (vinyl amines), poly (vinyl pyridine), poly (vinyl imidazole), and some imino substituted polyphosphazenes. Nitrogen-containing groups in these polymers can be converted to ammonium or quaternary salts. Ammonium or quaternary salts can also be formed from the backbone nitrogens or pendant imino groups. Examples of basic groups include amino and imino groups.

In some embodiments, the hydrogel-forming polymer is a water-soluble gelling agent. In some embodiments, the water-soluble gelling agent is a polysaccharide gum, such as a polyanionic polysaccharide. In some embodiments, cells or cell aggregates are encapsulated using an anionic polymer such as alginate to form a microcapsule shell, core, or combinations thereof.

In some embodiments, the matrix comprises a viscous aqueous solution. In some embodiments, the matrix can have a viscosity that is at least about two times, four times, six times, eight times, ten times, or twenty times the viscosity of water at about 25° C. In some embodiments, the matrix can have a viscosity that is at least about two times, four times, six times, eight times, ten times, or twenty times the viscosity of ethylene glycol at about 25° C.

In some embodiments, cells or cell aggregates are encapsulated using an anionic polymer such as alginate to form a hydrogel matrix (e.g., core). The hydrogel matrix can optionally be crosslinked, if desired. The matrix (e.g., the core) can also be formed from viscous solutions, such as, for example solutions of cellulose and its derivatives (e.g., carboxymethyl cellulose).

Mammalian and non-mammalian polysaccharides have been explored for cell encapsulation. These materials can be used, alone or in part, to form the core, the outer shell, or both the core and the outer shell. Exemplary polysaccharides include alginate, chitosan, hyaluronan (hyaluronic acid or HA), and chondroitin sulfate. Alginate and chitosan form crosslinked hydrogels under certain solution conditions, while HA and chondroitin sulfate are preferably modified to contain crosslinkable groups to form a hydrogel.

In some embodiments, the core, the outer shell, or both the core and the outer shell comprise alginate or derivative thereof. Alginates are a family of unbranched anionic polysaccharides derived primarily from brown algae which occur extracellularly and intracellularly at approximately 20% to 40% of the dry weight. The 1,4-linked α-1-guluronate (G) and β-D-mannuronate (M) are arranged in homopolymeric (GGG blocks and MMM blocks) or heteropolymeric block structures (MGM blocks). Cell walls of brown algae also contain 5% to 20% of fucoidan, a branched polysaccharide sulphate ester with 1-fucose four-sulfate blocks as the major component. Commercial alginates are often extracted from algae washed ashore, and their properties depend on the harvesting and extraction processes. Although the properties of the hydrogel can be controlled to some degree through changes in the alginate precursor (molecular weight, composition, and macromer concentration), alginate does not degrade, but rather dissolves when the divalent cations are replaced by monovalent ions. In addition, alginate does not promote cell interactions.

Alginate can form a gel in the presence of divalent cations via ionic crosslinking. Crosslinking can be performed by addition of a divalent metal cation (e.g., a calcium ion or a barium ion), or by cross-linking with a polycationic polymer (e.g., an amino acid polymer such as polylysine). See e.g., U.S. Pat. Nos. 4,806,355, 4,689,293 and 4,673,566 to Goosen et al.; U.S. Pat. Nos. 4,409,331, 4,407,957, 4,391, 909 and 4,352,883 to Lim et al.; U.S. Pat. Nos. 4,749,620 and 4,744,933 to Rha et al.; and U.S. Pat. No. 5,427,935 to Wang et al., each incorporated by reference herein. Amino acid polymers that may be used to crosslink hydrogel forming polymers such as alginate include the cationic poly (amino acids) such as polylysine, polyarginine, polyornithine, and copolymers and blends thereof.

In some embodiments, the core, the outer shell, or both the core and the outer shell comprise alginate or derivative thereof in combination with a protein (e.g., collagen or derivatives thereof or fibrin or derivatives thereof). In some embodiments, the hydrogel-forming polymer used to form the outer shell is alginate or derivative thereof.

In some embodiments, the core, the outer shell, or both the core and the outer shell comprise chitosan or derivative thereof. Chitosan is made by partially deacetylating chitin, a natural non-mammalian polysaccharide, which exhibits a close resemblance to mammalian polysaccharides, making it attractive for cell encapsulation. Chitosan degrades predominantly by lysozyme through hydrolysis of the acetylated residues. Higher degrees of deacetylation lead to slower degradation times, but better cell adhesion due to increased hydrophobicity. Under dilute acid conditions (pH<6), chitosan is positively charged and water soluble, while at physiological pH, chitosan is neutral and hydrophobic, leading to the formation of a solid physically crosslinked hydrogel. The addition of polyol salts enables encapsulation of cells at neutral pH, where gelation becomes temperature dependent.

Chitosan has many amine and hydroxyl groups that can be modified. For example, chitosan has been modified by grafting methacrylic acid to create a crosslinkable macromer while also grafting lactic acid to enhance its water solubility at physiological pH. This crosslinked chitosan hydrogel degrades in the presence of lysozyme and chondrocytes. Photopolymerizable chitosan macromer can be synthesized by modifying chitosan with photoreactive azidobenzoic acid groups. Upon exposure to UV in the absence of any initiator, reactive nitrene groups are formed that react with each other or other amine groups on the chitosan to form an azo crosslink.

In some embodiments, the core, the outer shell, or both the core and the outer shell comprise hyaluronan or derivative thereof, such as hyaluronic acid. Hyaluronan (HA) is a glycosaminoglycan present in many tissues throughout the body that plays an important role in embryonic development, wound healing, and angiogenesis. In addition, HA interacts with cells through cell-surface receptors to influence intracellular signaling pathways. Together, these qualities make HA attractive for tissue engineering scaffolds. HA can be modified with crosslinkable moieties, such as methacrylates and thiols, for cell encapsulation. Crosslinked HA gels remain susceptible to degradation by hyaluronidase, which breaks HA into oligosaccharide fragments of varying molecular weights. Auricular chondrocytes can be encapsulated in photopolymerized HA hydrogels where the gel structure is controlled by the macromer concentration and macromer molecular weight. In addition, photopolymerized HA and dextran hydrogels maintain long-term culture of undifferentiated human embryonic stem cells. HA hydrogels have also been fabricated through Michael-type addition reaction mechanisms where either acrylated HA is reacted with PEG-tetrathiol, or thiol-modified HA is reacted with PEG diacrylate.

Chondroitin sulfate makes up a large percentage of structural proteoglycans found in many tissues, including skin, cartilage, tendons, and heart valves, making it an attractive biopolymer for a range of tissue engineering applications. Photocrosslinked chondroitin sulfate hydrogels can be been prepared by modifying chondroitin sulfate with methacrylate groups. The hydrogel properties were readily controlled by the degree of methacrylate substitution and macromer concentration in solution prior to polymerization. Further, the negatively charged polymer creates increased swelling pressures allowing the gel to imbibe more water without sacrificing its mechanical properties. Copolymer hydro gels of chondroitin sulfate and an inert polymer, such as PEG or PVA, may also be used.

In some embodiments, the core, the shell, or both the core and the shell comprise a synthetic polymer or polymers. Polyethylene glycol (PEG) has been the most widely used synthetic polymer to create macromers for cell encapsulation. A number of studies have used poly(ethylene glycol) di(meth) acrylate to encapsulate a variety of cells. Biodegradable PEG hydrogels can be been prepared from triblock copolymers of poly(α-hydroxy esters)-b-poly(ethylene glycol)-b-poly(α-hydroxy esters) endcapped with (meth) acrylate functional groups to enable crosslinking PLA and poly (8-caprolactone) (PCL) have been the most commonly used poly(α-hydroxy esters) in creating biodegradable PEG macromers for cell encapsulation. The degradation profile and rate are controlled through the length of the degradable block and the chemistry. The ester bonds may also degrade by esterases present in serum, which accelerates degradation. Biodegradable PEG hydrogels can also be fabricated from precursors of PEG-bis-[2-acryloyloxy propanoate]. As an alternative to linear PEG macromers, PEG-based dendrimers of poly (glycerol-succinic acid)-PEG, which contain multiple reactive vinyl groups per PEG molecule, can be used. An attractive feature of these materials is the ability to control the degree of branching, which consequently affects the overall structural properties of the hydrogel and its degradation. Degradation will occur through the ester linkages present in the dendrimer backbone.

In some embodiments, the hydrogel-forming polymer can contain polyphosphoesters or polyphosphates where the phosphoester linkage is susceptible to hydrolytic degradation resulting in the release of phosphate. For example, a phosphoester can be incorporated into the backbone of a crosslinkable PEG macromer, poly(ethylene glycol)-di-[ethylphosphatidyl (ethylene glycol) methacrylate] (PhosPEGdMA), to form a biodegradable hydrogel. The addition of alkaline phosphatase, an ECM component synthesized by bone cells, enhances degradation. The degradation product, phosphoric acid, reacts with calcium ions in the medium to produce insoluble calcium phosphate inducing autocalcification within the hydrogel. Poly(6-aminoethyl propylene phosphate), a polyphosphoester, can be modified with methacrylates to create multivinyl macromers where the degradation rate was controlled by the degree of derivitization of the polyphosphoester polymer.

Polyphosphazenes are polymers with backbones consisting of nitrogen and phosphorous separated by alternating single and double bonds. Each phosphorous atom is covalently bonded to two side chains. The polyphosphazenes suitable for cross-linking have a majority of side chain groups which are acidic and capable of forming salt bridges with di-or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. Bioerodible polyphosphazines have at least two differing types of side chains, acidic side groups capable of forming salt bridges with multivalent cations, and side groups that hydrolyze under in vivo conditions, e.g., imidazole groups, amino acid esters, glycerol and glucosyl. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom.

In some embodiments, the core material of the disclosed composition comprises from about 0.1% to about 10% hyaluronic acid and a hydrogel. In some embodiments, the core material comprises from about 0.5% to about 8% hyaluronic acid and a hydrogel. In some embodiments, the core material comprises from about 1% to about 6% hyaluronic acid and a hydrogel. In some embodiments, the core material comprises from about 1.5% to about 5% hyaluronic acid and a hydrogel. In some embodiments, the core material comprises from about 2% to about 4% hyaluronic acid and a hydrogel. In some embodiments, the core material comprises from about 2.5% to about 5% hyaluronic acid and a hydrogel.

In some embodiments, the hydrogel comprised in the core material of the disclosed composition comprises from about 0.1% alginate to about 10% alginate. In some embodiments, the hydrogel comprised in the core material comprises from about 0.5% alginate to about 8% alginate. In some embodiments, the hydrogel comprised in the core material comprises from about 1% alginate to about 6% alginate. In some embodiments, the hydrogel comprised in the core material comprises from about 1.5% alginate to about 6% alginate. In some embodiments, the hydrogel comprised in the core material comprises from about 2% alginate to about 6% alginate. alginate. In some embodiments, the hydrogel comprised in the core material comprises from about 0.1% alginate to about 5.5% alginate. In some embodiments, the hydrogel comprised in the core material comprises about 0.1%, 0.5%, 1%, 2.5%, 3%, 4.5%, 5%, 5.5%, 6%, 6.5%, 7%, 7.5%, 8%, 8.5%, 9%, 9.5% or about 10% alginate.

In some embodiments, the outer shell of the disclosed composition comprises a spherical or substantially spherical polyanioic matrix. In some embodiments, the outer shell of the disclosed composition comprises 0.1% alginate to about 10% alginate. In some embodiments, the outer shell comprises from about 0.5% alginate to about 8% alginate. In some embodiments, the outer shell comprises from about 1% alginate to about 6% alginate. In some embodiments, the outer shell comprises from about 1.5% alginate to about 6% alginate. In some embodiments, the outer shell comprises from about 2% alginate to about 6% alginate. In some embodiments, the outer shell comprises from about 0.1% alginate to about 5.5% alginate. In some embodiments, the outer shell comprises about 0.1%, 0.5%, 1%, 2.5%, 3%, 4.5%, 5%, 5.5%, 6%, 6.5%, 7%, 7.5%, 8%, 8.5%, 9%, 9.5% or 10% alginate.

In some embodiments, the outer shell of the disclosed composition comprises 0.1% to about 10% chondroitin or poly-lysine. In some embodiments, the outer shell comprises from about 0.5% to about 8% chondroitin or poly-lysine. In some embodiments, the outer shell comprises from about 1% to about 6% chondroitin or poly-lysine. In some embodiments, the outer shell comprises from about 1.5% to about 6% chondroitin or poly-lysine. In some embodiments, the outer shell comprises from about 2% to about 6% chondroitin or poly-lysine. In some embodiments, the outer shell comprises from about 0.5% to about 5.5% chondroitin or poly-lysine. In some embodiments, the outer shell comprises about 0.1%, 0.5%, 1%, 2.5%, 3%, 4.5%, 5%, 5.5%, 6%, 6.5%, 7%, 7.5%, 8%, 8.5%, 9%, 9.5% or 10% chondroitin or poly-lysine.

In some embodiments, the outer shell comprises at least three layers of hydrogel, at least one layer of hydrogel comprises from about 0.1% to about 5.5% alginate. In some embodiments, the outer shell comprises at least three layers of hydrogel, at least one layer of hydrogel comprises from about 0.5% to about 5.5% chondroitin. In some embodiments, the outer shell comprises at least three layers of hydrogel, at least one layer of hydrogel comprises from about 0.5% to about 5.5% poly-lysine. In some embodiments, the outer shell comprises at least two layers of hydrogel, the first layer of hydrogel comprises from about 0.1% to about 5.5% alginate and the second layer of hydrogel comprises from about 0.5% to about 5.5% chondroitin. In some embodiments, the outer shell comprises at least two layers of hydrogel, the first layer of hydrogel comprises from about 0.1% to about 5.5% alginate and the second layer of hydrogel comprises from about 0.5% to about 5.5% poly-lysine. In some embodiments, the outer shell comprises at least three layers of hydrogel, the first layer of hydrogel comprises from about 0.1% to about 5.5% alginate, the second layer of hydrogel comprises from about 0.5% to about 5.5% chondroitin or poly-lysine, and the third layer of hydrogel comprises from about 0.1% to 5.5% alginate.

In some embodiments, the core and the outer shell can be formed so as to have distinct physical properties. For example, the core and the shell of the microcapsules can be fabricated to each have a different modulus of elasticity, density, hydrophobicity/hydrophilicity, polarity, thickness, or combinations thereof.

In some embodiments, the core material of the disclosed composition is spherical or substantially spherical in shape and comprises a diameter of from about 5 microns to about 1 millimeter. In some embodiments, the core material comprises a diameter of from about 5 nanometers to about 500 nanometers. In some embodiments, the core material comprises a diameter of from about 10 nanometers to about 200 nanometers in diameter. In some embodiments, the core material comprises a diameter of from about 20 nanometers to about 100 nanometers. In some embodiments, the core material comprises a diameter of about 5, 10, 15, 20, 25, 30, 35, 40, 45, 50, 55, 60, 75, 80, 85, 90, 95, 100, 150, 200, 250, 300, 350, 400, 450, 500, 600, 700, 800 or about 900 nanometers.

In some embodiments, the outer shell of the disclosed composition comprises a thickness from about 5 nanometers to about 1 millimeter. In some embodiments, the outer shell comprises a thickness from about 10 nanometers to about 500 nanometers. In some embodiments, the outer shell comprises a thickness from about 10 to about 200 nanometers. In some embodiments, the outer shell comprises a thickness of about 5, 10, 15, 20, 25, 30, 35, 40, 45, 50, 55, 60, 75, 80, 85, 90, 95, 100, 150, 200, 250, 300, 350, 400, 450, 500, 600, 700, 800 or 900 nanometers.

The cells or cell aggregates encapsulated in the core of the disclosed microcapsules can be any living cell type, including, but not limited to, endothelial cells, hormone secreting cells, epithelial absorptive cells (gut, exocrine glands and urogenital tract), metabolism and storage cells, barrier function cells (lung, gut, exocrine glands and urogenital tract), epithelial cells lining closed internal body cavities, ciliated cells with propulsive function, extracellular matrix secretion cells, contractile cells, blood and immune system cells, sensory transducer cells, autonomic neuron cells, sense organ and peripheral neuron supporting cells, central nervous system neurons and glial cells, lens cells, pigment cells, germ cells, and nurse cells. Also included are any stem cells and progenitor cells of the cells disclosed herein, as well as their progeny. The cells can be pluripotent stem cells, multipotent stem cells, progenitor cells, primary cells, or gametes. The cells can be a mixture of single cells or cell aggregates, such as antral or pre-antral follicles, or native tissue from other organs. In some embodiments, the cells are cancer stem cells (CSCs), such as CSCs isolated from a tumor. In some embodiments, the disclosed method can be used to enrich the CSCs, which would be advantageous for identifying effective therapies both in research lab and in clinical settings to eliminate cancer from its root, i.e. the CSCs.

In some embodiments, the cell in any of the disclosed compositions is CD44+. In some embodiments, the cell is CD44+ and CD133+. In some embodiments, the cell is CD44+/CD133+/CD24− or expresses CD24 to a limited degree. In some embodiments, the cell is a cancer stem cell.

In some embodiments, the cell expresses one or a combination of: NANOG, OCT4, SOX2, KLF4. In some embodiments, the cell expresses CD44, NANOG, OCT4, SOX2 and KLF4. In some embodiments, the cell expresses CD44, NANOG, OCT4, SOX2, KLF4 and CD133. In some embodiments, the cell exhibits mRNA expression for one or a combination of CD44, BMI1, ALDH1A1, ALDH7A1, CXCR4, CXCL3, HGF, DPPA2, HDAC1, HDAC2 and BMPER as measured by RNA sequencing (RNA-seq). In some embodiments, the cell exhibits mRNA expression for one or a combination of CD44, BMI1, ALDHIA1, ALDH7A1, CXCR4, CXCL3, HGF, DPPA2, HDAC1, HDAC2 and BMPER as measured by reverse transcription polymerase chain reaction (RT-PCR).

The disclosed microcapsules can further contain one or more bioactive agents within the core, shell, or combination thereof. In some embodiments, the bioactive agent is a therapeutic agent. In some embodiments, the bioactive agent can be a biomolecule. In certain embodiments, the bioactive agent can be a differentiation agent, such as a growth factor or chemokine suitable to promote the growth, survival, pluripotency, or differentiation of the cells encapsulated within the microcapsules. In certain embodiments, the bioactive agent is a growth factor such as VEGF (vascular endothelial growth factor), FGF (fibroblast growth factor), TGF (transforming growth factor), or combinations thereof. In some embodiments, the bioactive agent is a therapeutic agent such as an immunosuppressant and/or an anti-inflammatory agent.

In some embodiments, the encapsulated stem cells are treated with one or more differentiation agents to produce an encapsulated pre-differentiated stem cell. Pre-differentiation helps to prevent teratoma formation. For example, the encapsulated stem cells can be treated with one or more of BMP-4 and bFGF to direct the stem cells toward the mesodermal-early cardiac lineage before transplantation. Embryonic stem cells can be treated with EGF and bFGF to induce the differentiation to neural progenitor cells before implantation. Implanted progenitor cells can be differentiated to astrocytes, oligodendrocytes, and mature neurons. This can be used therapeutically for neural disorder treatments or spinal cord injuries. Mesenchymal stem cells can be cultured in specialized medium with TGF-β to induce chondrogenic differentiation for cartilage repair. Mesenchymal stem cells can be induced with growth factor IGF-2 and BMP-9 to induce osteogenic differentiation for bone regeneration. In some embodiments the differentiation factor is chosen from the below Table Z:

TABLE Z

| Examples of Differentiation Factors | | |
| --- | --- | --- |
| Gene/pathway | NCBI Gene ID | Compound/drug |
| Notch | Gene ID: 4851 | Notch ligands - Dll4, Dll1 and Jag1, DAPT/gamma-secretase |
| Sox17 | Gene ID: 64321 | TBD |
| Tgb1 | Gene ID: 21803 | Tgfb1, and inhibitors, SB-431542 . . . See http://www.rndsystems.com/product_results.aspx?m=6456&c=199 |
| BMPs/smads | Gene ID: 652 | BMP proteins and small molecule inhibitors K02288, DMH1, SB431542, inhibitors noggin |
| Runx1 | Gene ID: 861 | TBD |
| Gata2 | Gene ID: 2624 | TBD |
| Scl/Tal1 | Gene ID: 6886 | TBD |
| VEGF non-cell autonmous role/multiple pathways | Gene ID: 7422 | rVEGF, VEGF inhibitors - Sugen, Avastin AGM/stromal cell lines |

TABLE Z-continued

| Examples of Differentiation Factors | | |
| --- | --- | --- |
| PDGF | Gene IDs: 5156 and 5159 | recombinant protein and inhibitors imatinib, sunitinib, sorafenib, pazopanib and nilotinib. |

| Gene/pathway | Gene ID | Compound/drug |
| --- | --- | --- |
| Notch | Gene ID: 4851 | Notch ligands - Dll4, Dll1 and Jag1, DAPT/gamma-secretase |
| Sox17 | Gene ID: 64321 | TBD |
| Tgb1 | Gene ID: 21803 | Tgfb1, and inhibitors, SB-431542 . . . See http://www.rndsystems.com/product_results.aspx?m=6456&c=199 |
| BMPs/smads | Gene ID: 652 | BMP proteins and small molecule inhibitors K02288, DMH1, SB431542, inhibitors noggin |
| chromatin remodelers (chd1) | Gene ID: 1105 | TBD |
| VEGF | Gene ID: 7422 | rVEGF, VEGF inhibitors - Sugen, Avastin |
| PDGF | Gene IDs: 5156 and 5159 | recombinant protein and inhibitors imatinib, sunitinib, sorafenib, pazopanib and nilotinib. |

The encapsulated stem cells, with or without pre-differentiation, are in some embodiments released from the microcapsules prior to implantation, e.g., to mimic the physiologic process of the release of blastocyst from the zona pellucida for further differentiation. In some embodiments, the released stem cell aggregates are encapsulated in a biocompatible, biodegradable micro-matrix. The micro-matrix can be formed from a polyelectrolyte complex comprising one or more polycations and one or more polyanions. The micro-matrix can be formed throughout and/or surrounding the cell aggregates by sequential incubation of the cell aggregate in solutions of one or more polycations and one or more polyanions.

Suitable polyanions and polycations can be selected in view of a number of factors, including the desired in vivo stability of the micro-matrix (e.g., the desired in vivo biodegradation rate). Examples of suitable polycations include, for example, polypeptides, such as polyarginine, polylysine, polyhistidine, and polyornithine, polysaccharides, such as DEAE-dextran, chitosan, as well as synthetic polymers, such as polyallyamine or salts or quaternized derivatives thereof (e.g., polyallylamine hydrochloride), polyethyleneimine (PEI; e.g., linear PEI, branched PEI, or combinations thereof), modified derivatives of the above and mixtures thereof. Examples of suitable polyanions include, for example, polypeptides such as polyglutamic acid, polysaccharides, including alginates (e.g., sodium alginate), celluloses (e.g., cellulose sulfate), hyaluronic acid, and glycosaminoglycans such as chondroitin, proteins, such as heparin, as well as synthetic polymers, such as polystyrene sulfonate, modified derivatives of the above and mixtures thereof. In some embodiments, the polyelectrolyte complex can comprise one or more polyanions and one or more polycations selected from alginate, collagen, fibrin, hyaluronan, heparin, chondroitin, poly-1-lysine, ploy-1-glutamic acid, polyallylamine hydrochloride, polystyrene sulfonate, modified derivatives of the above and mixtures thereof.

For example, released cell aggregates can be encapsulated in a micro-matrix formed by soaking the aggregates in chitosan (e.g., 0.4% w/v) and then in oxidized alginate (e.g., 0.15% w/v) (or non-oxidized if slow degradation is desired) solution, optionally repeated one or more times. In preferred embodiments, the micro-matrix does not substantially increase the size of the stem cell aggregates. These aggregates can also be encapsulated to form single-cell microcapsules using the disclosed methods.

Encapsulating a one single cell into a microparticle can be performed by using a microfluidic devices configured to prepare the core-shell microcapsules disclosed herein. The microfluidic devices can comprise a core inlet channel, a first shell inlet channel, a second shell inlet channel, a first crosslinker inlet channel, and a second crosslinker inlet channel, all of which fluidly converge to form a flow focusing chamber; and an outlet channel flowing from the flow focusing chamber. Exemplary microfluidic devices are disclosed in US 2014/0127290, incorporated by reference herein.

In some embodiments, encapsulating a one single cell into a microparticle can be performed by using a devise or cassette disclosed herein. Such device or cassette comprises: (i) an exterior surface; and (ii) an interior surface comprising a microfluidic path defined by at least one inlet and at least one outlet, the at least one inlet positioned at one end of the interior surface accessible by a point exterior to the device and in fluid communication with the least one outlet on the opposite end of the device, the microfluidic path comprising from about 0.1 to about 3.0 inches in length, wherein the microfluidic path comprises a cell isolation segment and a microparticle formation segment, wherein the cell isolation segment comprises a length of microfluic path comprises cellular ligands and the microparticle formation segment comprises a reservoir within which core material and outer shell mix with at least one sample.

Methods

The disclosure further relates to methods of making and using the disclosed compositions. In some embodiments, the disclosure provides a method of culturing a cancer stem cell comprising exposing one single cancer stem cell encapsulated in a microparticle for about 7 days or more in a solid support at about 37 degrees Celsius and about 5% oxygen, wherein the microparticle comprises a core material enveloped by an outer shell as disclosed elsewhere herein. In some embodiments, the core material comprises from about 0.1 to about 10% hyaluronic acid and hydrogel, and the outer shell comprises a spherical or substantially spherical polyanioic matrix. In some embodiments, the cell is cultured for about 10 days. In some embodiments, the cell is cultured for about 21 days. In some embodiments, the cell is cultured for about 28 days. In some embodiments, the cell is encapsulated for a time period sufficient to form a spheroid of clonal cells. In some embodiments, the cell is from a primary tumor. In some embodiments, the cell is from a biopsy sample from a primary tumor of breast, colon or brain tissue.

In some embodiments, the disclosure provides a method of isolating a cell comprising exposing a sample of cells to at least one core material, at least one shell material and a hydrophobic agent for a time period sufficient for a cell from the sample to become encapsulated within a microparticle comprising the at least one core material and the at least one shell material, wherein the microparticle comprises the at least one core material enveloped by an outer shell as disclosed elsewhere herein. In some embodiments, the core material comprises from about 0.1 to about 10% hyaluronic acid and a hydrogel, and the outer shell comprises a spherical or substantially spherical polyanioic matrix. In some embodiments, the cell is from a primary tumor. In some embodiments, the cell is from a biopsy sample from a primary tumor of breast, colon or brain tissue.

In some embodiments, the disclosure provides a method of isolating a single cancer stem cell comprising: (i) exposing a sample of cells to a solid support comprising a probe to CD44 for a time period sufficient to capture a cell that expresses CD44; (ii) eluting the cell from the probe; and (iii) exposing the cell to a core material and an outer shell for a time period to encapsulate the cell with the core material and the outer shell, wherein the microparticle comprises the core material enveloped by the outer shell as disclosed elsewhere herein. In some embodiments, the core material comprising from about 0.1 to about 10% hyaluronic acid and a hydrogel, and the outer shell comprising a spherical or substantially spherical polyanioic matrix. In some embodiments, step (i) further comprises exposing the sample of cells to one or combination of probes of: NANOG, SOX2, OCT4, and KLF4. In some embodiments, the sample is from a primary tumor. In some embodiments, wherein the sample is from a sample comprising primary breast, brain or colon tumor cells. In some embodiments, the probe is an antibody that binds or associates to SEQ ID NO: 1, 2, 3, 4, 5, or 6. In some embodiments, the methods relate to a method of isolating a cancer stem cell by contacting a probe that binds or associates to SEQ ID NO: 4 or a functional fragment that comprises at least 70%, 80%, 85%, 90%, 91%, 92%, 93%, 94%, 95%, 96%, 97%, 98%, or 99% sequence identity to SEQ ID NO: 4. In some embodiments, the methods relate to a method of isolating a cancer stem cell by contacting a probe that binds or associates to SEQ ID NO: 1 or a functional fragment that comprises at least 70%, 80%, 85%, 90%, 91%, 92%, 93%, 94%, 95%, 96%, 97%, 98%, or 99% sequence identity to SEQ ID NO: 1. In some embodiments, the methods relate to a method of isolating a cancer stem cell by contacting a probe that binds or associates to SEQ ID NO: 2 or a functional fragment that comprises at least 70%, 80%, 85%, 90%, 91%, 92%, 93%, 94%, 95%, 96%, 97%, 98%, or 99% sequence identity to SEQ ID NO: 2. In some embodiments, the methods relate to a method of isolating a cancer stem cell by contacting a probe that binds or associates to SEQ ID NO: 3 or a functional fragment that comprises at least 70%, 80%, 85%, 90%, 91%, 92%, 93%, 94%, 95%, 96%, 97%, 98%, or 99% sequence identity to SEQ ID NO: 3. In some embodiments, the methods relate to a method of isolating a cancer stem cell by contacting a probe that binds or associates to SEQ ID NO: 5 or a functional fragment that comprises at least 70%, 80%, 85%, 90%, 91%, 92%, 93%, 94%, 95%, 96%, 97%, 98%, or 99% sequence identity to SEQ ID NO: 5. In some embodiments, the methods relate to a method of isolating a cancer stem cell by contacting a probe that binds or associates to SEQ ID NO: 6 or a functional fragment that comprises at least 70%, 80%, 85%, 90%, 91%, 92%, 93%, 94%, 95%, 96%, 97%, 98%, or 99% sequence identity to SEQ ID NO: 6. In some embodiments, the methods relate to a method of isolating a cancer stem cell by contacting a plurality of probes that bind or associate to SEQ ID NO: 4 or a functional fragment that comprises at least 70%, 80%, 85%, 90%, 91%, 92%, 93%, 94%, 95%, 96%, 97%, 98%, or 99% sequence identity to SEQ ID NO: 4, or a combination of the following: SEQ ID NO: 1, 2, 3, 5, and/or 6; eluting the cell from the probes; exposing the cell to one or a plurality of microcapsules for a period of time sufficient to encapsulate the cell; and then culturing the cell. The disclosure relates to a system comprising a microencapsulated cell disclosed above with cell culture medium.

In some embodiments, the disclosure provides a method of differentiating a cell in culture comprising exposing any of the disclosed compositions to one or more differentiation factors. In other embodiments, the disclosure relates to a method of imaging any of the disclosed composition comprising exposing the composition to microscopy. One skilled in the art will readily appreciate the wide range of methods and techniques used for detecting the presence and/or quantity of proteins in a complex sample. Techniques for detecting proteins include, but are not limited to, microscopy, immunostaining, immunoprecipitation, immunoelectrophoresis, Western blot, BCA assays, spectrophotometry, enzymatic assays, microchip assays, and mass spectrometry. In some embodiments, purification of proteins are necessary before detection of quantification techniques are employed. Techniques for purifying proteins include, but are not limited to, chromatography methods, including ion exchange, size-exclusion, and affinity chromatography, gel electrophoresis, and Bradford protein assays. In some embodiments, methods of measuring the presence, absence, or quantity probes bound or associated to the cells disclosed herein, or functional fragments thereof comprise antibodies or antibody fragments specific to the amino acid sequences, or functional fragments thereof, expressed on the surface of the cells disclosed herein.

The disclosure further provides a method of producing a colony or spheroid of cells from one single cancer stem cell comprising: exposing any of the disclosed composition to a cell culture medium. In some embodiments, the cell culture medium is a Dulbecco's Modified Eagle's Medium and Ham's F-12 Nutrient Mixture (DMEM/F12) or Dulbecco's Modified Eagle's Medium and Ham's F-12K (Kaighn's) 12 Nutrient Mixture (DMEM-F12-K). In some embodiments, the cell culture medium comprises any one or combination of each of the components listed in Table 1. In some embodiments, the cell or microencapsulated cell is in culture from about 7 to about 28 days. In some embodiments, the microencapsulated cell is cultured for a series of consecutive days in the DMEM/F12 or DMEM-F12-K for a time period sufficient to create a spheroid of cells derived clonally from the originally isolated cell. In some embodiments, the spheroid comprises from about 8 to about 5,000 cells. In some embodiments, the spheroid comprises from about 8 to about 15,000 cells. In some embodiments, the spheroid comprises from about 100 to about 1,000 cells.

The disclosure further relates to a method of seeding a culture with a microencapsulated cell by: exposing the spheroid of cells disclosed herein with an aqueous saline solution (such as sodium citrate) for a time period sufficient to dissolve the outer shell of the microparticle, and then seeding the cells into a solid support, or culture vessel, or bioreactor. In some embodiments, after seeding the spheroid of cells, the method further comprises emerging the cells in tissue culture medium.

Any suitable physiological response of the spheroid of cells may be determined, evaluated, measured, and/or identified in a method of the present disclosure. In some embodiments, 1, 2, 3, 4, or more physiological response(s) of the spheroid may be determined, evaluated, measured, and/or identified in a method of the present disclosure. In some embodiments, the physiological response of the spheroid may be a change in morphology for the spheroid. The method may comprise determining a change in morphology for the spheroid, which may include estimating at least one morphology parameter prior to contacting the spheroid with an agent, such as a chemical and/or biological compound, estimating the at least one morphology parameter after contacting the spheroid with the agent, and calculating the difference between the at least one morphology parameter prior to and after contacting the spheroid with the agent to provide the change in morphology for the spheroid. In some embodiments, the physiological response of the spheroid may be the spheroid shrinking or swelling in response to contact with an agent. Morphology of the spheroid may be determined using any methods known to those of skill in the art, such as, but not limited to, quantifying eccentricity and/or cross sectional area.

In some embodiments, the physiological response of the spheroid may be a change in volume for the spheroid. The method may comprise determining a change in volume for the spheroid, which may include estimating a first volume prior to contacting the spheroid with an agent, estimating a second volume after contacting the spheroid with the agent, and calculating the difference between the first volume and the second volume to provide the change in volume for the spheroid. In some embodiments, the physiological response of the spheroid may be the spheroid shrinking or swelling in response to contact with an agent.

To facilitate the detection of a protease disclosed herein, such as a fungal Sap protein, within a sample, a detectable substance may be pre-applied to a surface, for example a plate, well, bead, or other solid support comprising one or a plurality of reaction vessels. In some embodiments, sample may be pre-mixed with a diluent or reagent before it is applied to a surface. The detectable substance may function as a detection probe that is detectable either visually or by an instrumental device. Any substance generally capable of producing a signal that is detectable visually or by an instrumental device may be used as detection probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

In some embodiments, the detectable substance or probe may be a luminescent compound that produces an optically detectable signal that corresponds to the level or quantity of protease in the sample. For example, suitable fluorescent molecules may include, but are not limited to, fluorescein, europium chelates, phycobiliprotein, phycoerythrin, phycocyanin, allophycocyanin, o-phthaldehyde, fluorescamine, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or non-aqueous environment. For example, some suitable examples of ligands include, but are not limited to, pyridine; pyrazine; isonicotinamide; imidazole; bipyridine; terpyridine; phenanthroline; dipyridophenazine; porphyrin; porphine; and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium (II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537to Ewart. et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are not limited to, bis[(4, 4'-carbomethoxy)-2,2'-bipyridine]2-[3-(4-methyl-2,2'-bi-pyridine-4-yl)propyl]-1,3-dioxolane ruthenium (II); bis(2, 2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid]ruthenium (II) tris(2, 2'bipyridine)ruthenium (II); (2,2'-bipyridine) [bis-bis(1,2-diphenylphosphino)ethylene]2-[3-(4-methyl-2,2'-bipyridine-4'- -yl)propyl]-1,3-dioxolane osmium (II); bis(2, 2'-bipyridine)[4-(4'-methyl-2,2'-bipyridine)-butylamine] ruthenium (II); bis(2,2'-bipyridine)[1-bromo-4(4'-methyl-2, 2'-bipyridine-4-yl)butan-e]ruthenium (II); bis(2,2'-bipyridine) maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein by reference in their entireties.

In some cases, luminescent compounds may have a relatively long emission lifetime and/or may have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent probe or compounds have a Stokes shift of greater than about 50 nanometers, in some embodiments greater than about 100 nanometers, and in some embodiments, from about 100 to about 350 nanometers.

For example, exemplary fluorescent compounds having a large Stokes shift include lanthanide chelates of samarium (Sm (III)), dysprosium (Dy (III)), europium (Eu (III)), and terbium (Tb (I)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent labels. In addition, these chelates have narrow emission spectra, typically having bandwidths less than about 10 nanometers at about 50% emission. One suitable europium chelate is N-(p-isothiocyanatobenzyl)-diethylene triamine tetraacetic acid-Eu.sup.+3.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N,N-bis(carboxymethyl)amin-o]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate.beta.-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. No. 6,030,840 to Mullinax, et al.; U.S. Pat. No. 5,585,279 to Davidson; U.S. Pat. No. 5,573, 909 to Singer, et al.; U.S. Pat. No. 6,242,268 to Wieder, et al.; and U.S. Pat. No. 5,637,509 to Hemmila, et al., which are incorporated herein by reference in their entirety.

The agent may be any suitable compound, such as, for example, an organic compound, a small molecule compound (e.g., a small molecule organic compound), a protein, an antibody, an oligonucleotide (e.g., DNA and/or RNA), a gene therapy vehicle (e.g., a viral vector) and any combination thereof. One or more (e.g., 1, 2, 3, 4, 5, or more) agents may be used in a method of the present invention. For example, a method of the present invention may comprise contacting a spheroid of the present invention with two or more different agents. In some embodiments, a method of the present invention may modulate an activity in a spheroid indirectly, such as, for example, by contacting a spheroid of the present invention with a gene therapy vehicle (e.g., a viral vector).

The disclosure relates to a method of testing the toxicity or function of an agent to one or a plurality of cells cultured by methods disclosed herein.

In some embodiments, the method of culturing cells comprises, exposing the composition of cells disclosed herein with an aqueous saline solution (such as sodium citrate or claicum citrate) for a time period sufficient to dissolve the outer shell and/or core of the microparticle. In some embodiments, the aqueous saline solution is from about 0.01 M sodium citrate to about 1 M sodium citrate. In some embodiments, the compositions disclosed herein are exposed to an aqueous saline solution for from about 1 to about 20 minutes in order to sufficiently dissolve the microcapsule outer shell and/or alginate in the microparticle. After the single cell or plurality of cells are no longer encapsulated, the cells may be seeded and, optionally, differentiated, prior to being exposed to one or a plurality of agents. In some embodiments, the one or plurality of cells is a cancer stem cells or cluster of clonal cancer stem cells or progeny of the single cancer stem cell, isolated by the microencapsulation methods disclosed herein. In some embodiments, the cells are seede in a cell culture system, bioreactor or other vessel, and then differentiated into osteocytes, cardiomyocytes, or neuronal cells by exposure of the cells to one or more differentiation factors. After about 1, 2, 3, 4, 5, 6, 7, 8, 9, 10, 11, 12, 13, or 14 or more days in culture in a fully differentiated state, methods can further comprise exposing the cells to one or more test agents. Systems comprising a bioreactor and one or a plurality of cell compositions can, in some embodiments, further comprise one or more test agents.

A method of the present disclosure relates to a method of culturing cells and/or a spheroid. Culturing may be carried out using methods known to those knowledgeable in the field. In some embodiments, cells and/or a spheroid may be cultured for any desired period of time, such as, but not limited, hours, days, weeks, or months. In some embodiments, cells and/or a spheroid may be cultured for about 1, 2, 3, 4, 5, 6, or 7 days, or about 1, 2, 3, 4, 5, 6, 7, 8, 9, 10, or 11 or more weeks. In some embodiments, the methods of the disclosure relate to exposing the composition disclosed herein to tissue or cell culture medium for no less than 7 days, such that the composition comprises one single cancer stem cell and their progeny.

Cell culture media suitable for the methods of the present invention are known in the art and include, but are not limited to, BEGM™ Bronchial Epithelial Cell Growth medium, Dulbecco's Modified Eagle's Medium (DMEM), Dulbecco's Modified Eagle's Medium high glucose (DMEM-H), McCoy's 5A Modified Medium, RPMI, Ham's media, Medium 199, mTeSR, and so on. The cell culture medium may be supplemented with additional components such as, but not limited to, vitamins, minerals, salts, growth factors, carbohydrates, proteins, serums, amino acids, attachment factors, cytokines, growth factors, hormones, antibiotics, therapeutic agents, buffers, etc. The cell culture components and/or conditions may be selected and/or changed during the methods of the present invention to enhance and/or stimulate certain cellular characteristics and/or properties. Examples of seeding methods and cell culturing methods are described in U.S. Pat. Nos. 5,266,480, 5,770,417, 6,537,567, and 6,962,814 and Oberpenning et al. "De novo reconstitution of a functional mammalian urinary bladder by tisme engineering" Nature Biotechnology 17:149-155 (1999), which are incorporated herein by reference in their entirety. Table 1 below provides the components comprised in DMEM-F12 cell culture medium.

TABLE 1

Components of Dulbecco's Modified Eagle's Medium and Ham's F-12 Nutrient Mixture (DMEM/F12).

| Component | Conc. (g/L) |
|---|---|
| Ammonium Molybdate•4H$_2$O (optional) | 0.00000618 |
| Ammonium Metavandate (optional) | 0.00000058 |
| Calcium Chloride | 0.1166 or 0.1545 |
| Cupric Sulfate•5H$_2$O | 0.0000013 |
| Ferric Nitrate•9H$_2$O | 0.00005 |
| Ferrous Sulfate•7H$_2$O | 0.000417 |
| Manganese Sulfate (optional) | 0.000000151 |
| Magnesium Chloride•6H$_2$O | 0.0612 |
| Magnesium Sulfate (anhydrous) | 0.04884 |
| Nickel Chloride (optional) | 0.00000012 |
| Potassium Chloride | 0.3118 |
| Sodium Bicarbonate (optional) | 1.2 |
| Sodium Chloride | 6.996 |
| Sodium Metasilicate•9H$_2$O (optional) | 0.0000142 |
| Sodium Selenite (optional) | 0.00000519 |
| Sodium Phosphate Dibasic (anhydrous) | 0.07102 |
| Sodium Phosphate Monobasic (anhydrous) | 0.0543 |
| Stannous Chloride•2H$_2$O (optional) | 0.00000011 |
| Zinc Sulfate•7H$_2$O | 0.000432 |
| L-Alanine | 0.00445 |
| L-Arginine•HCl | 0.1475 |
| L-Asparagine•H$_2$O | 0.0075 |
| L-Aspartic Acid | 0.00665 |
| L-Cystine•2HCl | 0.03129 |
| L-Cysteine•HCl•H$_2$O | 0.01756 |
| L-Glutamic Acid | 0.00735 |
| L-Glutamine (optional) | 0.365 |
| Glycine | 0.01875 |
| L-Histidine•HCl•H$_2$O | 0.03148 |
| L-Isoleucine | 0.05447 |
| L-Leucine | 0.05905 |
| L-Lysine•HCl | 0.09125 |
| L-Methionine | 0.01724 |
| L-Phenylalanine | 0.03548 |
| L-Proline | 0.01725 |
| L-Serine | 0.02625 |
| L-Threonine | 0.05345 |
| L-Tryptophan | 0.00902 |
| L-Tyrosine•2Na•2H$_2$O | 0.05579 |
| L-Valine | 0.05285 |
| D-Biotin | 0.0000035 |
| Choline Chloride | 0.00898 |
| Folic Acid | 0.00265 |
| myo-Inositol | 0.0126 |
| Niacinamide | 0.00202 |
| D-Pantothenic Acid (hemicalcium) | 0.00224 |
| Pyridoxal•HCl (optional) | 0.002 |
| Pyridoxine•HCl (optional) | 0.002031 |
| Riboflavin | 0.000219 |
| Thiamine•HCl | 0.00217 |
| Vitamin B12 | 0.00068 |

TABLE 1-continued

Components of Dulbecco's Modified Eagle's Medium and Ham's F-12 Nutrient Mixture (DMEM/F12).

| Component | Conc. (g/L) |
|---|---|
| D-Glucose | 3.15 |
| HEPES (optional) | 3.5745 |
| Hypoxanthine | 0.0021 or 0.00244 |
| Linoleic Acid | 0.000042 |
| Phenol Red•Na (optional) | 0.00863 |
| Putrescine•HCl | 0.000081 |
| Pyruvic Acid•Na | 0.11 or 0.055 |
| DL-Thioctic Acid | 0.000105 |
| Thymidine | 0.000365 |

EXAMPLES

Example 1. Bioinspired Isolation and Culture of Highly Tumorigenic and Metastatic Cancer Stem Cells Capable of Multilineage Differentiation Cancer stem cells (CSCs) are rare cancer cells that are postulated to be responsible for cancer relapse and metastasis. However, CSCs are difficult to isolate and poorly understood. Here, we report a bioinspired approach for label-free isolation and culture of CSCs, by microencapsulating one cancer cell in the nanoliter-scale hydrogel core of each prehatching embryo-like core-shell microcapsule. Only a small percentage of the individually microencapsulated cancer cells could proliferate into a cell colony. Gene and protein expression analyses indicate high stemness of the cells in the colonies. Importantly, the colony cells are capable of cross-tissue multilineage (e.g., endothelial, cardiac, neural, and osteogenic) differentiation, which is not observed for "CSCs" isolated using other contemporary approaches. Further studies demonstrate the colony cells are highly tumorigenic, metastatic, and drug resistant. These data show the colony cells obtained with our bioinspired one-cell-culture approach are truly CSCs. Significantly, multiple pathways are identified to upregulate in the CSCs and enrichment of genes related to the pathways is correlated with significantly decreased survival of breast cancer patients. Collectively, this study may provide a valuable method for isolating and culturing CSCs, to facilitate the understanding of cancer biology and etiology and the development of effective CSC-targeted cancer therapies.

1. Materials and Methods i. Materials

Chitosan oligosaccharide of pharmaceutical grade (MW: 80 kDa, 95.5% deacetylation) was purchased from Zhejiang Golden-Shell Biochemical Co. Ltd (Zhejiang, China). Hyaluronan (HA, MW: 151-300 kDa) was purchased from Lifecore Biomedical (Chaska, MN, USA).

Doxorubicin hydrochloride (DOX) was purchased from LC laboratories (Woburn, MA, USA). Irinotecan/camptothecin-11 (CPT-11) was purchased from Selleck Chemicals (Houston, TX, USA). The cell counting kit-8 (CCK-8) cell proliferation reagent was purchased from Dojindo Molecular Technologies (Rockville, MD, USA). Fetal bovine serum (FBS) and penicillin/streptomycin were purchased from Invitrogen (Carlsbad, CA, USA). The DMEM, EMEM, F12K, RPMI-1640, and DMEM/F-12K cell culture media were purchased from ATCC (Manassas, VA, USA). Sodium alginate was purchased from Sigma (St. Louis, MO, USA) and further purified by washing in chloroform and charcoal and dialyzing (MWCO: 50 kD) for 24 hours, followed by freeze-drying to remove water. All other chemicals were purchased from Sigma unless specifically mentioned otherwise.

ii. Fabrication of Microfluidic Devices

Polydimethylsiloxane (PDMS) based microfluidic devices were fabricated as described previously.[S1] Briefly, a non-planar silicon master with patterned microfluidic channels was prepared by utilizing a 3-layer SU8 fabrication technique. To do this, a 100 μm-thick layer of SU82050 was coated on a 4-inch silicon wafer. The wafer was then soft-baked at 95° C., followed by exposure to UV light through a shadow mask for the core channel. After post-exposure baking, an additional layer (50-μm thick) of SU8 2050 was coated and baked at 95° C. Thereafter, the wafer was exposed to UV light with a different shadow mask to pattern the shell channel. Afterward, a third SU8 2050 layer of 50-μm thickness was coated and baked at 95° C. Finally, the wafer was exposed to UV light with a shadow mask to pattern the oil and extraction channels. All three exposures were aligned by utilizing an EVG620 mask aligner. In the end, the SU8 pattern was developed in SU8 developer solution. To fabricate PDMS microfluidic devices, a PDMS pre-polymer solution (at 10:1 ratio of the pre-polymer to its curing agent) was poured onto the silicon wafer followed by baking at 65° C. for a minimum of 3 hours. Thereafter, two PDMS slabs with identical channel design were plasma treated for 30 seconds using the Harrick PDC-32G plasma cleaner and aligned under microscope to form an assembled device. The devices were kept at 65° C. for at least 2 days to make them sufficiently hydrophobic for further experimental use.

iii. Microencapsulation of One Single Cell and ACA Coating

The fluid in the core channel was an aqueous sodium alginate solution (2%) with or without 0.5% hyaluronic acid (HA), whereas the fluid in the shell channel was the 2% alginate solution. To encapsulate one single cell in each microcapsule, the core solution was suspended with cells at $10^4$ cells ml$^{-1}$. Solution in the extraction channel (FIG. 7) was composed of 0.5% wt high-viscosity sodium carboxymethyl cellulose and 0.5% wt low-viscosity sodium carboxymethyl cellulose. All solutions were prepared in 0.3 M D-Mannitol solution and buffered with 10 mM HEPES to maintain the neutral pH 7.4. In order to crosslink alginate in the microcapsules, stable emulsion composed of mineral oil and 1 g ml$^{-1}$ aqueous calcium chloride solution (volume ratio: 10 to 3with the addition of 1.5% SPAN 80) was prepared by sonication for 1 minute using a Branson 450 digital sonifier. All the solutions were injected into the microfluidic device using a syringe pump to generate microcapsules. Flow rates for core, shell, oil, and aqueous extracting fluids were 120 μl hr$^1$, 220 μl hr$^{-1}$, 4 ml hr$^{-1}$, and 4 ml hr$^{-1}$, respectively. Outlets were connected to a 50 ml tube containing the cell culture medium to collect the microcapsules. For ACA coating, a layer-by-layer coating approach was utilized.[S2] Microcapsules after collection were washed twice with mannitol and suspended in a 0.4% wt chitosan (in 0.9% saline) solution for 30-40 seconds to form the AC coating. Thereafter, microcapsules were washed twice with isotonic mannitol solution to remove chitosan. The AC coated microcapsules were then suspended in an 0.2% wt sodium alginate (in 0.9% saline) solution for 2-3 minutes to form a stable alginate coating. Finally, the resultant microcapsules with ACA coating were washed twice with the mannitol solution and placed in growth medium for culture. Alginate is a negatively charged polymer which forms strong electrostatic interactions with the positively charged chitosan polymer.[S2] Lastly, the microcapsules contained two or more cells were removed by pipetting with a 100-ul pipette tip under microscope.

iv. Cell Culture and In Vitro Cell Viability

For 2Dcells culture, human MDA-MB-231, MCF-7, PC-3, and OVCAR-8 cancer cells were cultured in Corning (Lowell, MA, USA) T75 flasks in DMEM, EMEM, F12K, and RPMI-1640 medium supplemented with 10% FBS and 1% penicillin/streptomycin at 37° C. in a humidified 5% $CO_2$ incubator, respectively. For Ucells culture, cells were cultured in Corning (Lowell, MA, USA) 6-well ultralow attachment plate (ULAP) at a density of 20,000 cells ml$^{-1}$ in CSC medium consisting of serum-free DMEM/F12 supplemented with 5 μg ml$^{-1}$ insulin, 20 ng ml$^{-1}$ epidermal growth factor (EGF), 20 ng ml$^{-1}$ basic fibroblast growth factor (bFGF), 1×B27 (Invitrogen, Carlsbad, CA, USA), 0.4% (w v$^{-1}$) bovine serum albumin, 100 U ml$^{-1}$ penicillin, and 100 μg ml$^{-1}$ streptomycin. The cell spheroids or aggregates were collected after 7 days for further experiments. For lcsc and Mcells cultures, microcapsules encapsulated with one (for lcsc) or multiple (for Mcells) cells were cultured in the aforementioned CSC medium. To determine viability of cells under 2Dcells culture, cells were transferred into 96-well plates first. After 12 hours, the pure medium was replaced with medium containing various drug formulations and further cultured for 24 hours. For Ucells, Mcells, and lcsc cultures, cell aggregates/spheroid/colonies were divided equally into three groups and cultured with medium containing various drug formulations in 24-well plate for 24 hours. The cell viability was then evaluated using the CCK-8 cell proliferation reagent per the manufacturer's instructions. Cell viability was calculated as the ratio of the cell number determined for each group with a treatment to that of control group with no treatment.

v. RNA sequencing

PicoPure RNA Isolation Kit was used to extract RNAs from cells in the lcsc group because of the small number of cells available in this group, while RNAs in cells from the other three groups were isolated with a Qiagen (Germantown, MD, USA) RNAeasy Plus Mini Kit. Quality and quantity of the extracted RNAs were analyzed using an Agilent Technology 2100 Bioanalyzer with a high sensitivity DNA chip (RIN>8) (Table 2). RNAs were processed through SMARTer Ultra Low RNA Seq Kit v4 (Clontech) for library preparation according to the manufacturer's instructions. Libraries were finally sequenced on an Illumina HiSeq sequencer with paired (2×125 base pairs) end reads at the DNA Sequencing Center in Brigham Young University, Provo, UT, USA.

TABLE 2

Detailed information on the amount and quality of the RNAs extracted from cells of the 2Dcells, Ucells, Mcells, and 1csc groups.

| Sample ID | Group | Sample Type | Species | Reference Genome | RNA Integrity | Concentration (ng μl$^{-1}$) | Volume (μl)* | Extraction method | A260/280 |
|---|---|---|---|---|---|---|---|---|---|
| 1 | 2Dcells | RNA | Human | Human | 9.8 | 1263 | >20 | A | 2.06 |
| 2 | 2Dcells | RNA | Human | Human | 9.9 | 1652 | >20 | A | 2.03 |
| 3 | 2Dcells | RNA | Human | Human | 9.9 | 820.7 | >20 | A | 2.03 |

TABLE 2-continued

Detailed information on the amount and quality of the RNAs extracted
from cells of the 2Dcells, Ucells, Mcells, and 1csc groups.

| Sample ID | Group | Sample Type | Species | Reference Genome | RNA Integrity | Concentration (ng $\mu l^{-1}$) | Volume ($\mu l$)* | Extraction method | A260/ 280 |
|---|---|---|---|---|---|---|---|---|---|
| 4 | Ucells | RNA | Human | Human | 10 | 13.5 | >20 | A | 1.99 |
| 5 | Ucells | RNA | Human | Human | 10 | 1403 | >20 | A | 2.01 |
| 6 | Ucells | RNA | Human | Human | 9.9 | 33.9 | >20 | A | 2.03 |
| 7 | Mcells | RNA | Human | Human | 9.5 | 64.4 | >20 | A | 1.98 |
| 8 | Mcells | RNA | Human | Human | 10 | 123 | >20 | A | 1.94 |
| 9 | Mcells | RNA | Human | Human | 10 | 92.6 | >20 | A | 1.9 |
| 10 | 1csc | RNA | Human | Human | 9.3 | 26.7 | ~11 | B | 1.76 |
| 11 | 1csc | RNA | Human | Human | 9.8 | 37.1 | ~11 | B | 1.78 |
| 12 | 1csc | RNA | Human | Human | 9.5 | 93.7 | ~11 | B | 1.82 |

1*: A: Qiagen RNAeasy plus mini kit; B: Amhion Pico Pure RNA isolation kit.

vi. Differential Gene Expression Analysis

RNA-sequencing quality was analyzed using the FASTQC program (bioinformatics.babraham.ac.uk/projects/fastqc/). Reads were trimmed and aligned to the GRCh38 human reference genome. At least 30 million reads per sample were aligned to the genome. Differential gene expression analyses were performed using DESEQ2. For our downstream analyses, we focused on transcripts with change greater than 2.0 in expression and adjusted p value less than 0.05. Pathway analyses on the differentially expressed genes were performed using the ingenuity pathway analysis (IPA, Qiagen) method. Gene set enrichment analysis (GSEA, http://www.broadinstitute.org/gsea) was performed to determine if the predefined gene sets (hallmark gene sets downloaded from the Molecular Signature Database available from Broad Institute, Cambridge, MA, USA) show significant differences between the 1csc and other groups.

vii. In Vitro Imaging

For imaging OCT4, SOX2, NANOG, and KLF4, cells from the 2Dcells (cultured on collagen-coated cover glasses), Ucells, Mcells, and 1csc groups were fixed with 4% paraformaldehyde (PFA) for 20 minutes at room temperature. After washing with PBS for 3 times, the fixed cells were incubated in 0.1% TritonX-100 and 3% BSA in PBS at room temperature for 1 hour to permeabilize the cell plasma membrane and block nonspecific binding. Then, the cells were incubated at 4° C. with OCT4 (Abcam, Cambridge, MA, USA, ab18976), SOX2 (Abcam, ab97959), NANOG (Abcam, ab109250), and KLF4 (Abcam, ab215036) antibodies at the dilution ratio of 1:200. After 12 hour, the unbounded antibody was removed by washing with PBS for three times. Afterward, the cells were incubated with FITC-conjugated secondary antibody (Thermo Fisher) at the dilution ratio of 1:200 in PBS with 1% BSA at room temperature for 1 hour, followed by washing for three times with PBS. The cells were then covered with cover glass and anti-fade mounting medium (Vector Laboratories Burlingame, CA, USA) for examination using an Olympus FluoView™ FV1000 confocal microscope.

viii. Flow Cytometry

Samples of the Mcells and 1csc groups were incubated with an isotonic solution of sodium citrate first to release cell spheroids/colonies from the microcapsules by pipetting. These cell spheroids and colonies together with cells in the 2Dcells and Ucells groups were treated with 0.25% Trypsin to obtain detached single cells (3-5×10^5 cells per sample). The cells were then fixed, permeabilized, and blocked with non-specific binding in the same way as aforementioned for in vitro imaging. Afterward, the cells were incubated with antibodies at the dilution ratio of 1:200 at room temperature for 1 hour and the unbounded antibody was removed by washing with PBS for three times. The cells were then incubated with FITC-conjugated secondary antibody (Thermo Fisher) at the dilution ratio of 1:200 in PBS with 1% BSA at room temperature for 1 hour, followed by washing for three times with PBS. Lastly, the cells were analyzed using a BD (Franklin Lakes, NJ, USA) LSR-II flow cytometer and Diva software. When needed, the cells were collected by centrifugation at 400 g for 5 minutes without significant cell loss during the procedure.

ix. Endothelial Differentiation.

The endothelial differentiation was conducted by following a previously published protocol with slight modification.[S3] Briefly, dissociated single cells of the four groups were obtained in the same way as aforementioned for flow cytometry studies and cultured with the endothelial growth medium (EGM) supplemented with 50 ng ml^{-1} VEGF in 6-well plate for 4-6 days. For tube formation, Matrigel (Corning, Lowell, MA, USA) was added into 24-well plates and incubated at 37° C. for 30 minutes to coat the plates. The gels were then overlaid with 1×10^5 cells suspended in the EGM medium and incubated for 12 hours. Successful endothelial differentiation was confirmed with immunostainings of human CD31 (Abcam, ab28364) and VE-cadherin (Cell Signaling Technology, Danvers, MA, USA, #2158) at the dilution ratio of 1:200 and 1:100, respectively. For the immunostaining, cells were fixed (without permeabilization) and blocked for non-specific binding in the same way as aforementioned for in vitro imaging. For actin staining, fixed cells were incubated with FITC-labeled phalloidin (Sigma, 10 µg ml^{-1} in PBS) for 30 minutes and washed with PBS for three times before imaging. The imaging was conducted in the same as that mentioned above.

x. Cardiac Differentiation

Cardiac differentiation was conducted using the PSC Cardiac Differentiation Kit (Thermo Fisher, A2921201) according to the manufacturer's instructions. Briefly, dissociated single cells obtained as aforementioned were cultured in 6-well plate for 24 hours in either DMEM medium for 2Dcells or CSC medium for other groups and then replaced with pre-warmed Cardiomyocyte Differentiation Medium A given in the kit. After 2 days, the medium was aspirated slowly from each well and replaced with pre-warmed Cardiomyocyte Differentiation Medium B given in the kit. Following culture for 2 days, the medium in each well was replaced with pre-warmed Cardiomyocyte Maintenance Medium given in the kit and the medium was changed every two days. The cells were then collected for further characterization after one week of culture. For immunostaining, cells were cultured on collagen-coated cover glass, blocked, fixed, and permeabilized as aforementioned. Cells were then incubated at 4° C. with cTnI (Abcam, ab47003) and a-AC-TININ (Sigma, A7811) antibodies at the dilution ratio of 1:200. After 12 hours, the unbounded antibody was removed by washing with PBS for three times. Cells were then incubated with secondary antibody at the dilution ratio of 1:200 in PBS with 1% BSA at room temperature for 1 hour and washed for three times with PBS. Afterward, the cells were covered with cover glass and anti-fade mounting medium (Vector Laboratories Burlingame, CA, USA) for examination using an Olympus FluoView™ FV1000 confocal microscope. For flow cytometry studies, the cells after cardiac differentiation were detached by trypsin and stained with cTnI and a-actinin in the same way as aforementioned and further analyzed using a BD (Franklin Lakes, NJ, USA) LSR-II flow cytometer and Diva software.

xi. Osteogenic Differentiation

This was conducted using the StemPro™ Osteogenesis Differentiation Kit (Thermo Fisher, A1007201) according to the manufacturer's instructions. Briefly, single cells obtained as aforementioned were cultured in 6-well plate for 24 hours in either DMEM medium for 2Dcells or CSC medium for other groups. Afterward, the medium was slowly replaced with pre-warmed Osteogenesis Differentiation Medium given in the kit. After 21 days of culture, the cells were stained with Alizarin Red S given in the kit to stain and visualize calcium deposition in the samples.

xii. Neural Differentiation

The neural induction was done by following a previously published protocol with slight modification.[S4] Briefly, single cells obtained as aforementioned for all the four groups were plated on a cell culture dish and cultured to 50-70% confluency in either DMEM medium for the 2Dcells group or CSC medium for other groups. Then, the culture medium was replaced with neural induction medium prepared by supplementing the neural basal medium (Gibco, Gaithersburg, MD, USA) with 10 M SB431542 (Sigma) and 1 µM desomorphine (Sigma), 1×N2 (Gibco), 1×B27(Gibco), and 1 mM L-glutamine. The cells were cultured for 10 days with the medium being changed every other day. For immunostaining, cells were processed as aforementioned with primary antibodies of MUSASHI-1 and β-TUBULIN (R&D Systems, Minneapolis, MN, USA) at the dilution ratio of 1:500. The nuclei were stained with 1 µM DAPI at room temperature for 5 minutes. Images were taken using a Zeiss (Thornwood, NY, USA) LSM 710 confocal scanning microscope.

xiii. Animals and Animal Experiments

All animal experiments were performed in accordance with the "Guide for the Care and Use of Laboratory Animals of the US National Institutes of Health". The experimental protocols were reviewed and approved by the Institutional Animal Care and Use Committee of the Ohio State University and all efforts were made to minimize animal suffering. Both the female NOD SCID and C57BL/6 mice of 6-week old were purchased from Charles River (Wilmington, MA, USA) and maintained on a 16:8 hours light-dark cycle.

To investigate tumorigenesis, detached single cells were suspended at 5,000 cells ml$^{-1}$ in a mixture (1:1) of PBS and Matrigel. A total of 500 cells in 100 µl of the mixture was injected into the fat pad of each 7-week-old female NOD SCID mouse. Tumor growth was monitored every 5 days. The tumor volume was calculated as: $V=(L\times W^2)\times 0.5$, where L is long diameter and W is short diameter of the tumors determined using a caliper. The mice were euthanized on day 55 and tumors were collected. For histological analyses, tumors were fixed with 4% PFA, embedded with paraffin, and stained with hematoxylin and eosin (H&E).

For 2Dcells, Ucells, Mcells, or 1csc culture of in vivo tumor cells, fresh tumors were gashed into small squares (~0.5 mm3) and put in a 50 ml conical tube. After washed with Hank's balanced salt solution (HBSS, Thermo Fisher) containing calcium and magnesium for 3 times, the small squares were incubated with collagenase (100 U ml$^{-1}$, Life Technologies, NY, USA) for 4 hours at 37° C. with careful agitation of the samples approximately every half an hour. The dispersed cells were collected into another sterile 50-ml conical tube by passing through filtration with a 40-µm sterile nylon mesh cell strainer. The cells were then collected by centrifugation at 200 g for 5 minutes and further treated with 0.25% Trypsin to obtain dissociated single cells. The dissociated cells were cultured in Corning (Lowell, MA, USA) T75 flasks in DMEM medium for 12 hours and then replaced with fresh medium to remove dead cells and debris. After cultured to 70-80% confluency, the cells were detached with 0.25% Trypsin and further cultured in ultralow attachment plate for 3 days with DMEM medium to remove the fibroblasts. Finally, the tumor cells were collected by centrifugation at 200 g for 5 minutes and treated with 0.25% Trypsin for 2Dcells, Ucells, Mcells, or 1csc culture as aforementioned in the microencapsulation or in vitro cell culture sections.

To investigate metastasis, dissociated single cells obtained as aforementioned for the four groups were intravenously injected into the C57BL/6 mice of 7-week old through the tail vein ($2\times 10^6$ cells per mouse and 8 mice per group). After 2 months, mice were sacrificed, and their major organs collected. The lungs were fixed with Bouin solution (Sigma) for imaging. For immunostaining of CD44 (Abcam, ab157107) and Ki-67 (Thermo Fisher, MA5-14520), lungs were collected and then frozen with the Tissue-Tek (Sakura Finetek, Torrance, CA, USA) O.C.T. Compound and Cryomold at-80° C. for 24 hours. The lungs were then cut into slices of 10-µm thick using a cryomicrotome (Leica Biosystems Inc, IL, USA) and transferred onto microscope slides. The immunostaining was conducted as aforementioned at the dilution ratio of 1:200 for both antibodies. For histological analysis, lungs, kidneys, and livers were fixed with 4% PFA, embedded with paraffin, and then stained with H&E as aforementioned.

xiv. Immunostaining of Tumor Tissue

For staining of mouse CD31 (mCD31, R&D Systems, AF3628), human CD31 (hCD31, R&D Systems, BBA7), and human VE-cadherin (hVE-cadherin, Cell Signaling Technology, #2158), tumors collected at day 55 were conducted as aforementioned to obtain the 10 pm-thick slices for immunostaining. The slides were incubated in 3% BSA and 0.1% TritonX-100 in 1×PBS at room temperature for 1 hour, followed by overnight incubation at 4° C. with mouse CD31 and hVE-cadherin antibodies. The samples were then washed for 3 times with PBS and incubated in the dark at room temperature for 1 hour with Alexa 680 and Rhodamine B-labeled secondary antibody (Thermo Fisher) diluted (1:50 dilution) in 1×PBS containing 1% BSA. Afterward, the preparations were incubated with hCD31 antibody at 4° C. overnight, washed for 3 times with PBS, and incubated with FITC-labeled secondary antibody (Thermo Fisher, diluted at 1:50 dilution in 1×PBS containing 1% BSA) in the dark at room temperature for 1 hour. For PCNA staining, the tumor tissues on glass slides were incubated in PCNA antibody (Sigma, AV03018) at 4° C. for 12 hours after blocking potential non-specific binding and permeabilizing with 3% BSA and 0.1% TritonX-100 in 1×PBS at room temperature for 1 hour. The slides were then washed for 3 times with PBS and incubated in dark at room temperature for 1 hour with FITC-labeled secondary antibody (Abcam) diluted in PBS containing 1% BSA. Finally, the preparations were washed and further stained for nuclei using Hoechst 33342 for examination with an Olympus FV1000 confocal microscope.

xv. EMT Staining

Attached 2D cells (for 2Dcells culture), spheroids (for Mcells and Ucells cultures), and colonies (for 1csc culture) were fixed with 4% paraformaldehyde for 20 minutes at room temperature. All samples were then washed for 3 times with PBS and incubated in 3% BSA and 0.1% TritonX-100 in PBS at room temperature for 1 hour to block nonspecific binding and permeabilize the cell plasma membrane, respectively. Afterwards, samples were incubated overnight with primary antibodies (Cell Signaling Technology, EMT antibody sampler kit #9782) including VIMENTIN (1:100), E-CADHERIN (1:200), and β-CATENIN (1:100). Next day, unbounded antibody was removed by washing with PBS for three times. Samples were then incubated with FITC-labeled secondary antibody at the dilution ratio of 1:200 in PBS with 1% BSA at room temperature for 1 hour and washed for three times with PBS. Finally, samples were mounted using an antifade mounting medium (Vector Laboratories Burlingame, CA, USA) for examination using an Olympus FluoView™ FV1000 confocal microscope.

xvi. Statistical Analysis

All data are reported as mean±standard deviation (s.d.) from at least three independent runs. One-way ANOVA with post hoc Tukey test was used for comparison among more than two groups by GraphPad Prism8 Software. For the patient survival analysis, Kaplan-Meier method was used and carried out with the IBM SPSS 22 software. The invasive breast cancer dataset[S5] from the cBioPortal for Cancer Genomics database was used for the patient survival analysis. In all cases, a p value less than 0.05 was considered to be statistically significant.

2. Results i. Bioinspired One Cell Culture for Isolating CSCs

Figure 7:
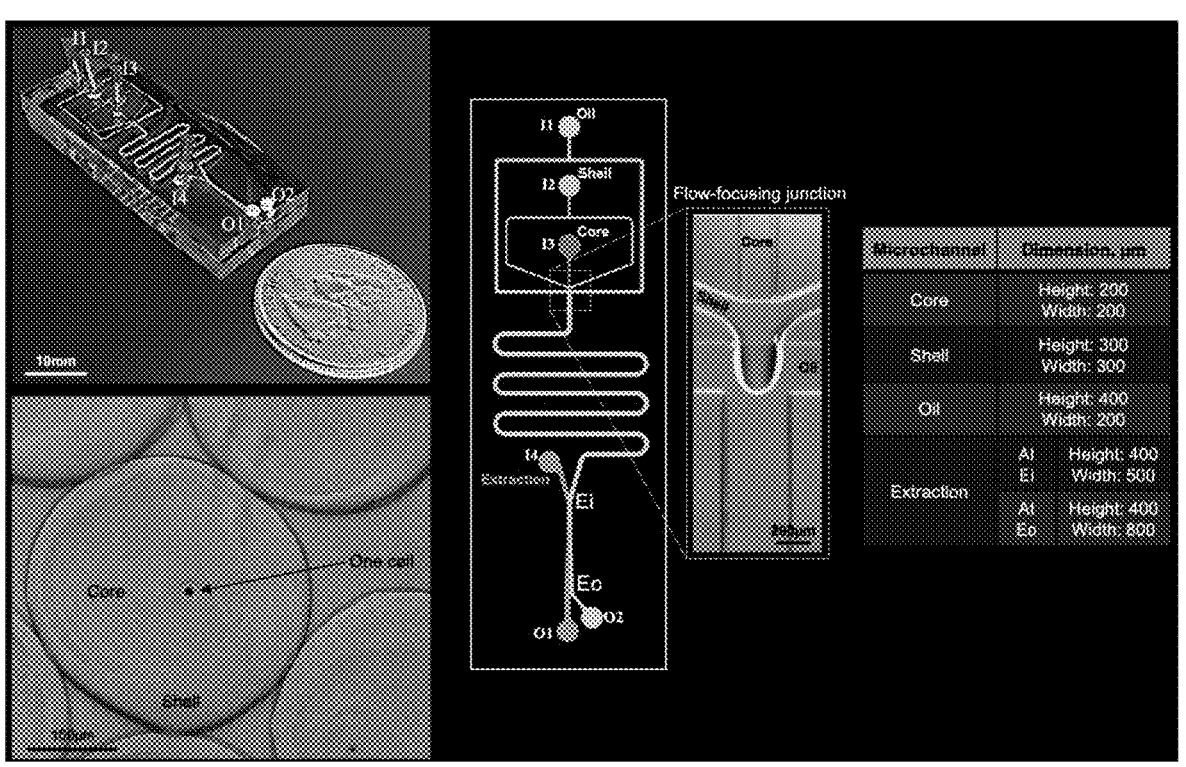
FIG. 7 depicts the microfluidic device (top left: real image and middle: a schematic diagram and real image) used for one single cell microencapsulation with the flow-focusing mechanism in this study. The microchannel system in the real image of the device on the top left is filled with the aqueous solution of 0.08% (w v$^{-1}$) Fast Green FCF dye (Sigma) for better visualization of the microchannels. The bright field image in the middle shows the design of the flow-focusing junction and the table on the right indicates the dimensions of the various channels in the device. The height is in the direction perpendicular to the schematic diagram in the middle. Mineral oil emulsified with aqueous calcium chloride solution, aqueous sodium alginate solution (to form the microcapsule shell), a mixture of aqueous sodium alginate and hyaluronan (HA) solutions (with or without cells) to form the microcapsule core, and aqueous extraction solution are pumped into the device via inlets I1, I2, I3, and I4, respectively. The aqueous extraction solution (containing core-shell microcapsules) and mineral oil exit the device from outlets O1 and O2, respectively. Also shown is a typical image (bottom left) of the one cell-laden microcapsule with a core-shell configuration collected from the aqueous exit 01.

To address the aforementioned challenges and efficiently isolate and culture CSCs, we have been inspired by the nature's approach of culturing stem cells in the prehatching embryos, which starts from one cell (zygote) that proliferates into a cell colony (morula) in a miniaturized (nanoliter) core surrounded by a shell known as the zona pellucida.[13] More specifically, we fabricated miniaturized, three-dimensional (3D), prehatching embryo-like, core-shell microcapsules to encapsulate one single cancer cell in the nanoliterscale hydrogel core of each of the microcapsules for CSC isolation and culture. This mimics the formation of stem cell colony (i.e., morula) from one cell (i.e., zygote) in the prehatching embryo. To achieve this, a microfluidic device was used to fabricate the one cancer cell-laden core-shell hydrogel microcapsules with a core diameter of 206.5±19.7 μm and shell thickness of 40.5±14.2 μm (FIG. 1A and FIG. 7). Since recent studies show that the 3D hydrogel/scaffold may induce anoikis of non-stem cancer cells,[14] we applied an alginate-based hydrogel scaffold in the core of the microcapsules. Alginate is used because it is highly biocompatible and does not have cell adhesion molecules.[15] The latter is good for inducing anoikis of non-stem cancer cells. To optimize the concentration of alginate, the aforementioned MDA-MB-231, MCF-7, PC-3, and OVCAR-8 cancer cells were cultured in alginate hydrogel scaffolds with concentrations ranging over 0.5-3% wt. Few cancer cells can proliferate or survive in the 2% and 3% alginate hydrogels.

Figure 1B:
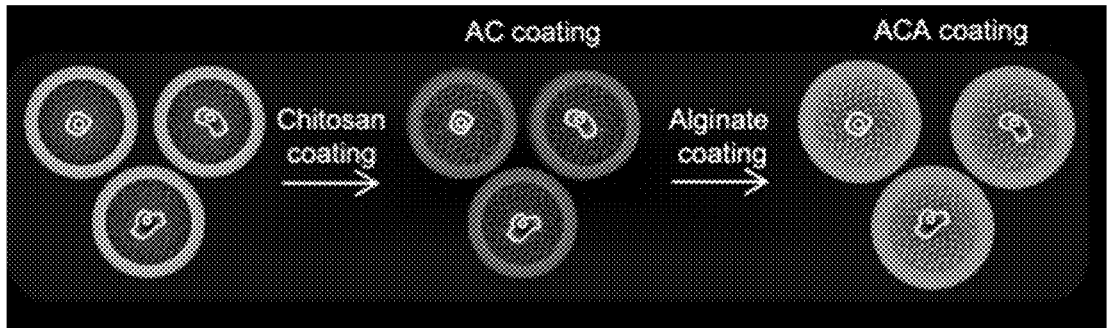
Figure 1C:
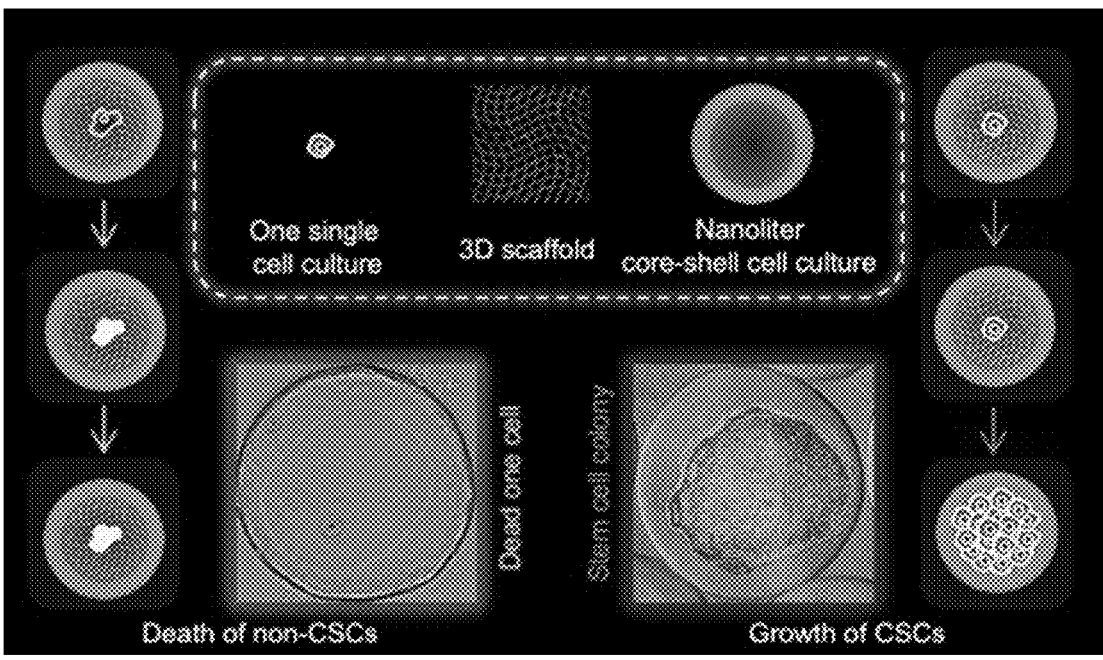
Figure 8A:
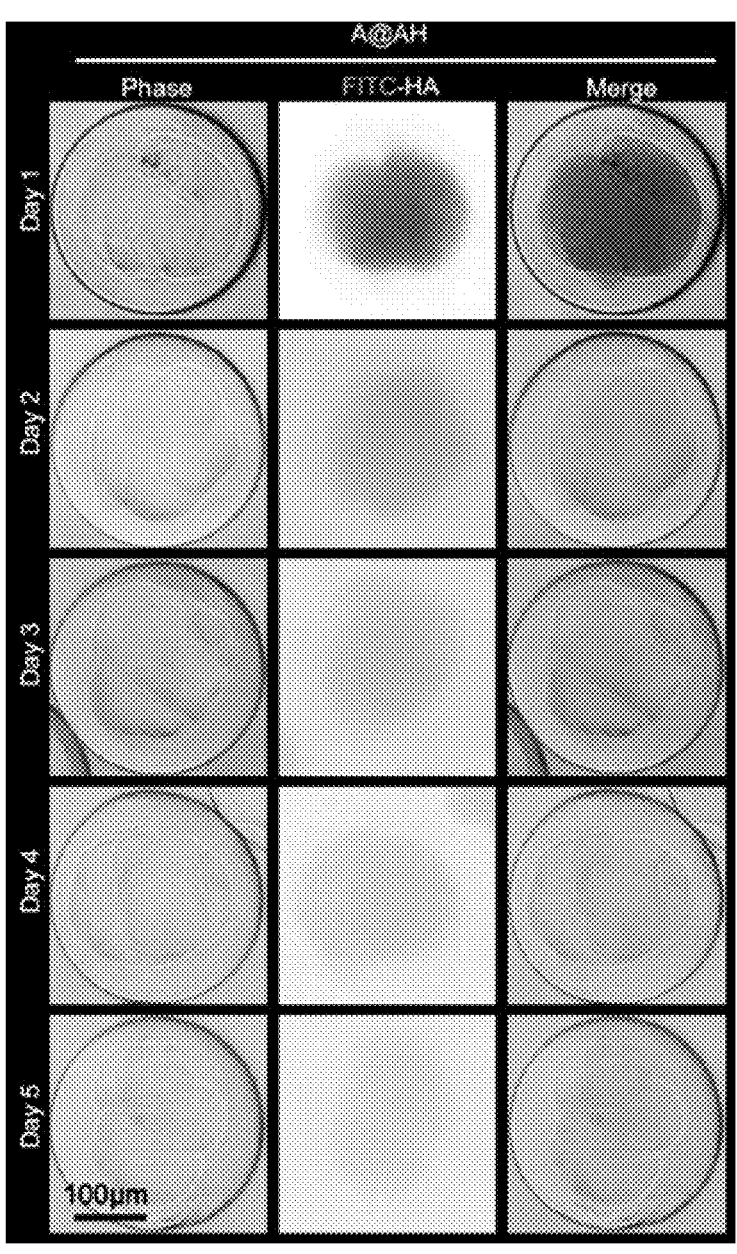
FIG. 8A-8C depict that ACA coating retains HA inside the core of the core-shell microcapsules.
Figure 8B:
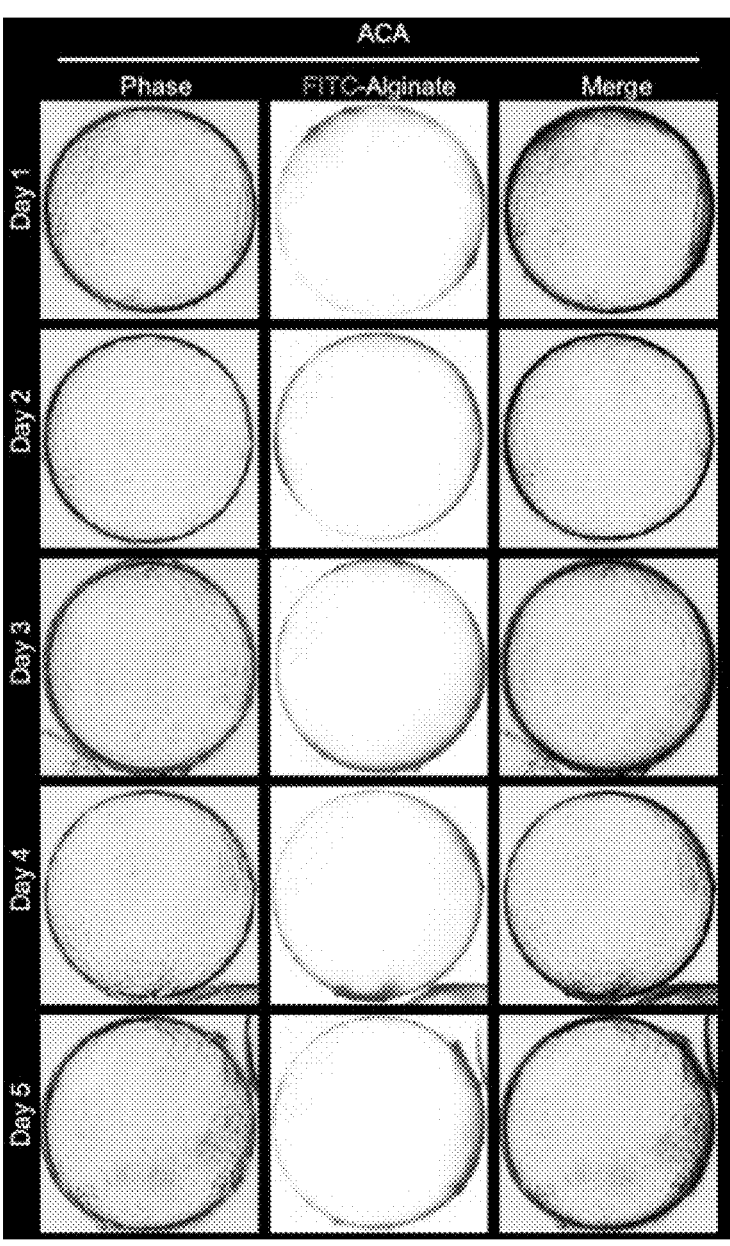
Figure 8C:
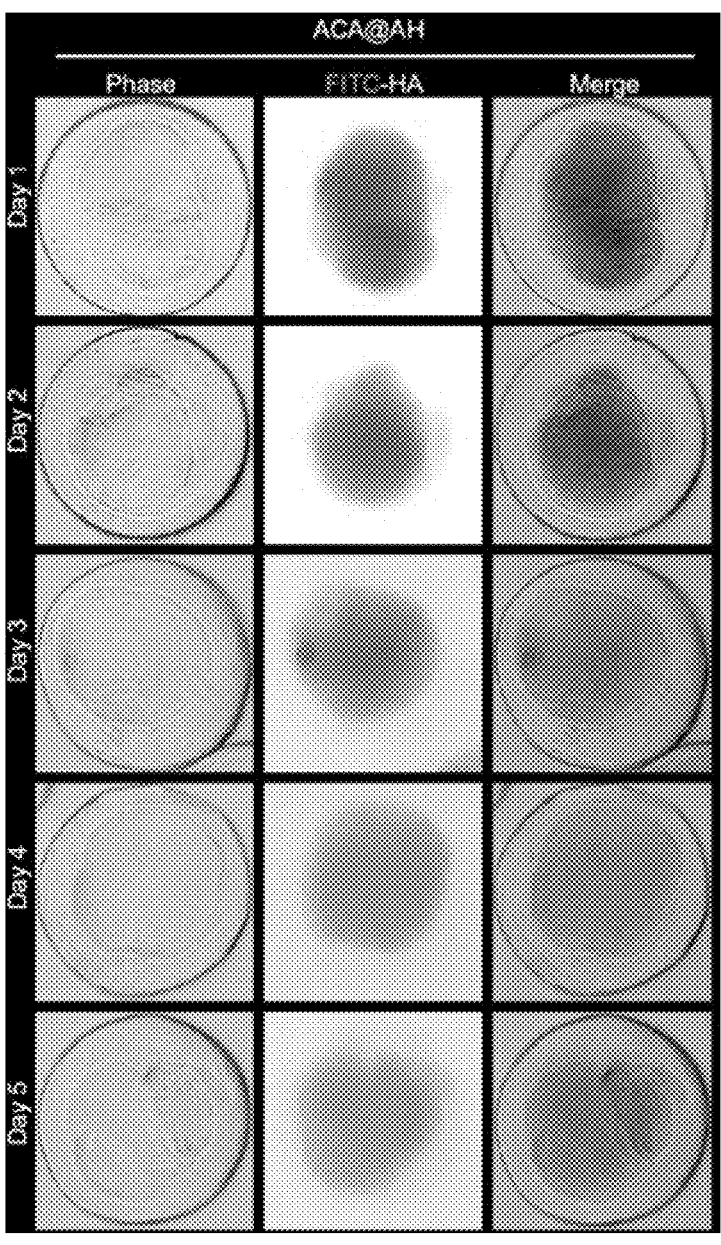

Therefore, 2% alginate was utilized as the core scaffold of the microcapsules to induce anoikis of non-stem cancer cells. Furthermore, hyaluronan (HA, 0.5% wt) was embedded in the core as it could play a key role in the CSC niche.[16] The shell of the microcapsules was fabricated with pure alginate hydrogel (2%, FIG. 1A). A stable core-shell structure was observed in the resultant microcapsules with an overall size of 300 μm (FIG. 8A). However, the HA (labeled with fluorescein isothiocyanate or FITC in short) may gradually diffuse out of the microcapsules during five days of incubation in medium. To overcome this, we further incubate the microcapsules sequentially with chitosan and alginate (FIG. 1B), to form an alginate-chitosan-alginate (ACA) coating (FIG. 8B, where the alginate in the ACA coating is labelled with FITC) on the microcapsule surface for reducing the shell permeability. This effectively prevents the leaking of HA from the microcapsule core (FIG. 8C) although the coatings are very thin and do not significantly change the overall size of the microcapsules. By combining the bioinspired one single cell culture and miniaturized 3D hydrogel scaffold selection (FIG. 1C), we hypothesized that only the one single CSC in the ACA coated microcapsules consisting of a core scaffold of both alginate and HA and an alginate shell (ACA@AH: A for alginate, H for HA, and C for chitosan) could survive and proliferate during culture.

Figure 1D:
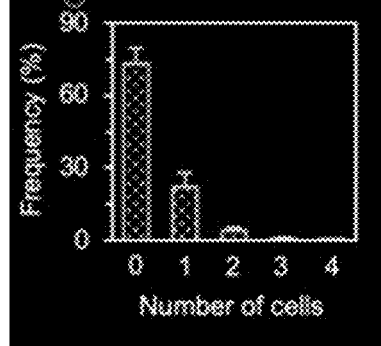
Figure 1E:
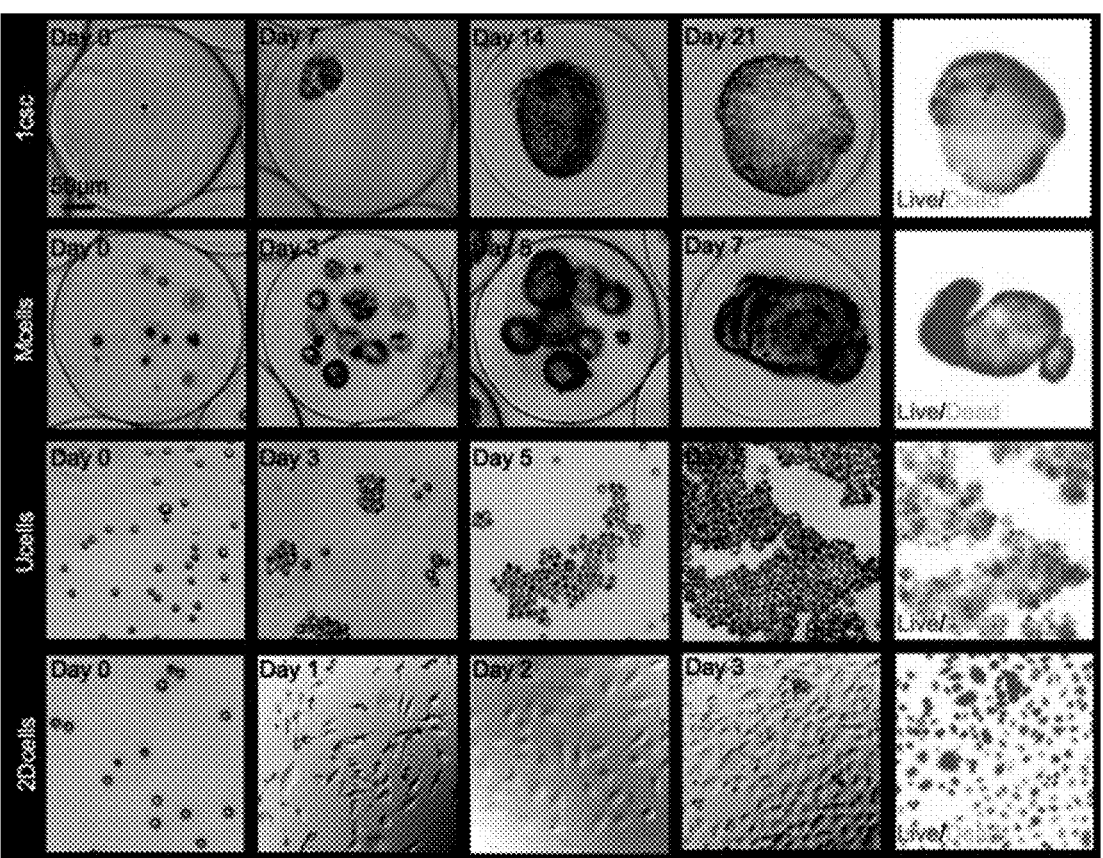
Figure 1F:
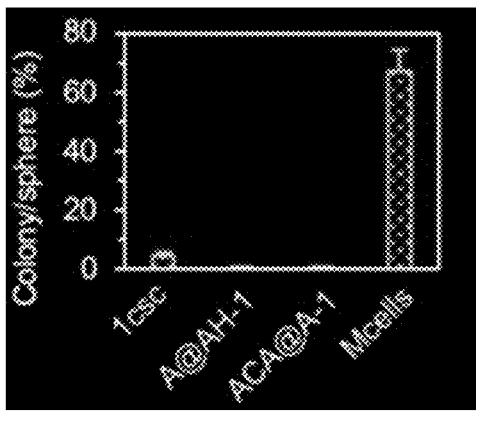
Figure 9A:
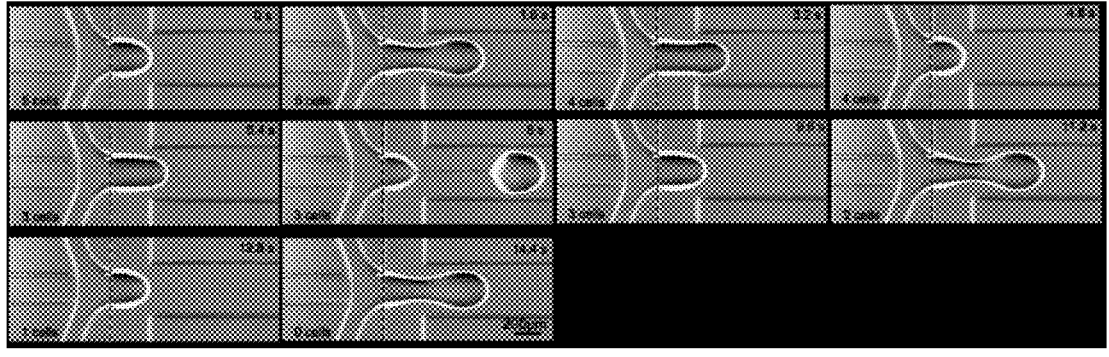
FIG. 9A-9B depict time-sequenced bright-field micrographs showing the microfluidic process of encapsulating one single cell in each core-shell microcapsule. Micrographs either without (FIG. 9A) or with (FIG. 9B) dashed color circles to indicate the location of cells in the flow-focusing junction.
Figure 9B:
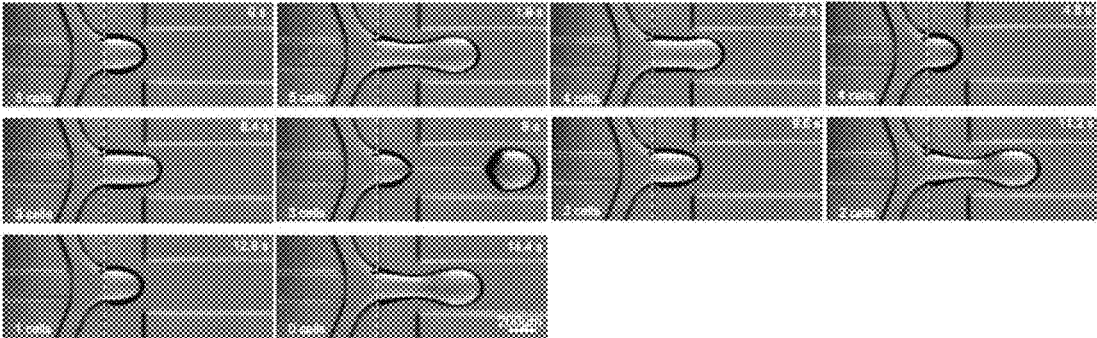
Figure 10A:
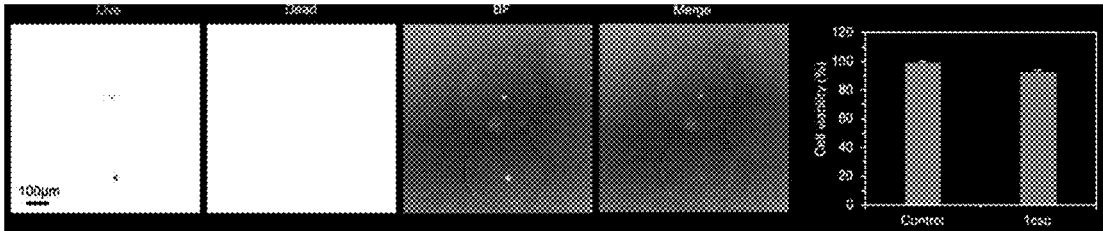
FIG. 10A-10D depict that the one single cell in microcapsules is highly viable after the microencapsulation procedure and the colonies formed are highly stable.
Figure 10B:
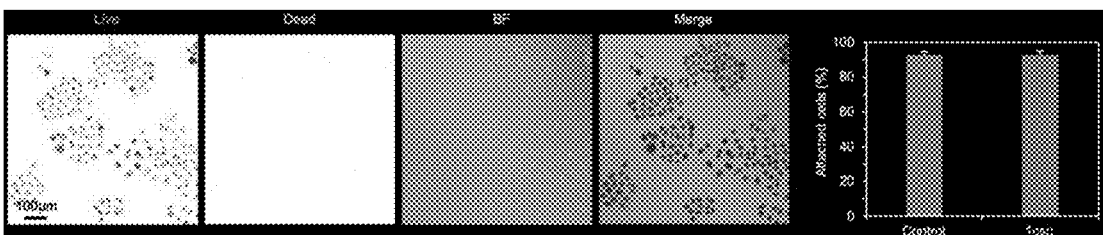
Figure 10C:
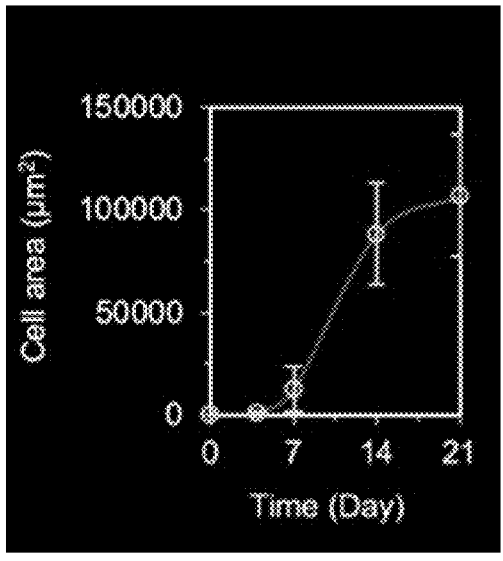
Figure 10D:
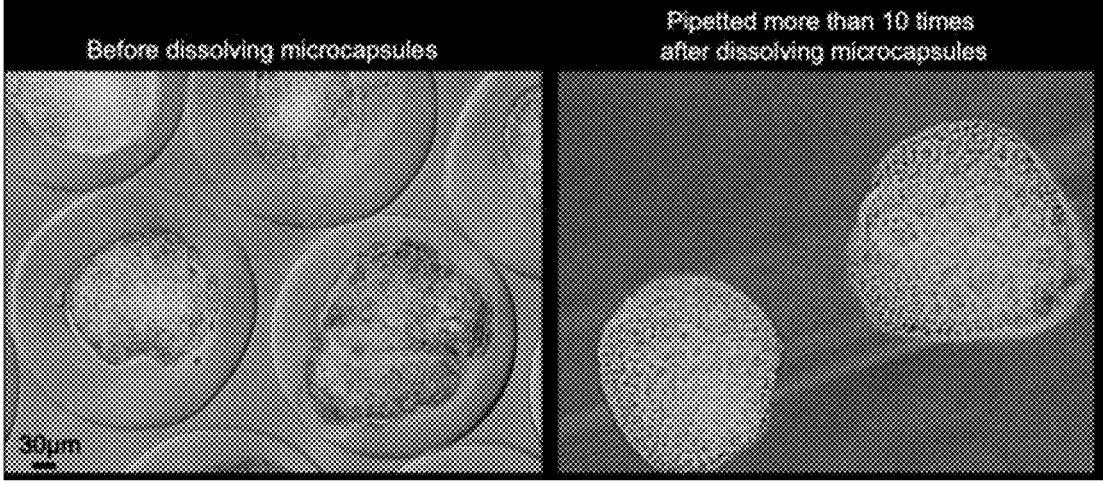
Figure 20:
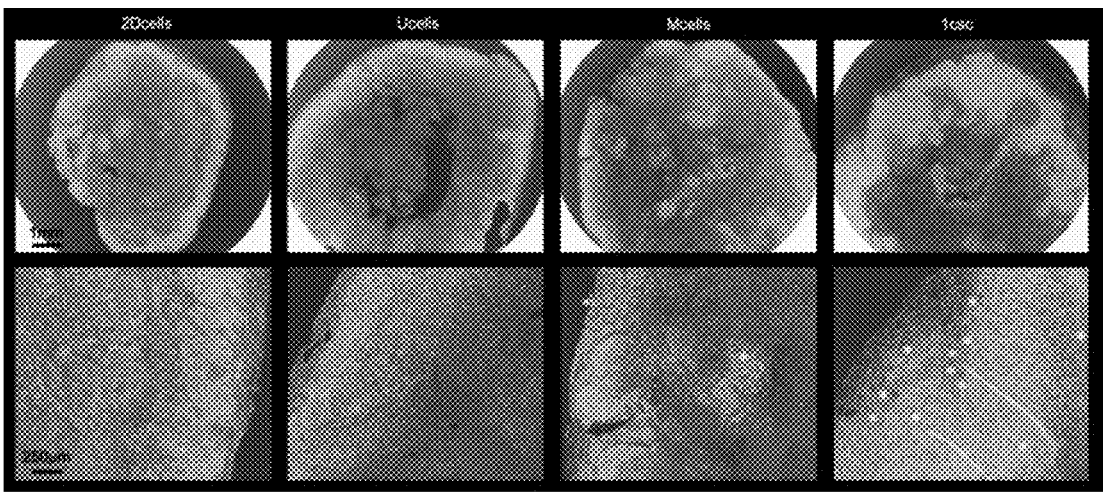
FIG. 20 depicts significantly increased formation of blood vessels and decreased area of necrosis in G1 tumors of the 1csc group. Representative images of hematoxylin and cosin (H&E) staining of G1 tumor tissues collected after sacrificing mice on day 55 for the 2Dcells, Ucells, Mcells, and 1csc groups. Quantitative analyses show that tumors of the 1csc group have significantly less necrotic area than tumors in the other three groups. This is potentially due to the greater capability of the 1csc colony cells in differentiating into endothelial cells to form blood vessels indicated by blue asterisks. Error bars denote mean±s.d., n=3. Statistical analyses were performed by one-way ANOVA with post hoc Tukey test. The 1csc group is compared with the 2Dcells, Ucells, and Mcells groups altogether.
Figure 20:
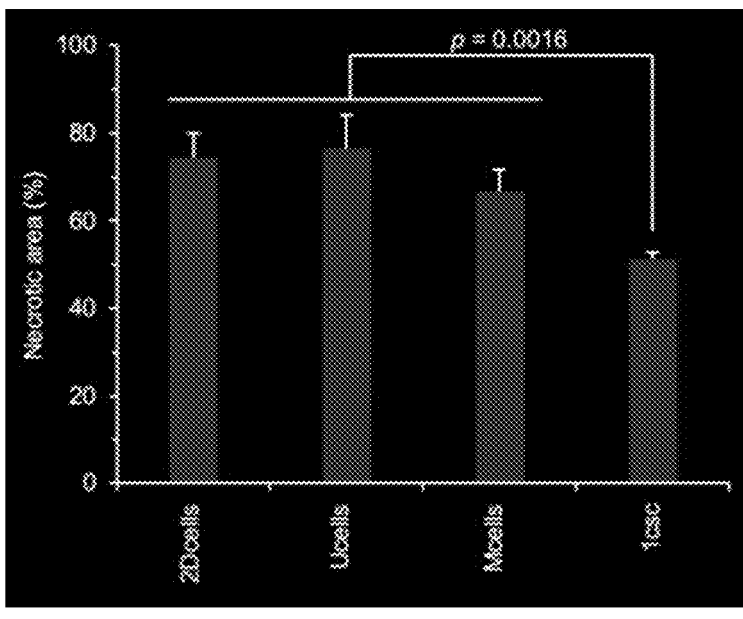

To test the hypothesis, we quantified the efficiency of obtaining one single cell in the microcapsules after microfluidic encapsulation first. As shown in FIG. 1D and FIG. 9, ~20% of the ACA@AH microcapsules contained one single cell, whereas ~4% of the microcapsules contained two or more cells which were removed immediately by pipetting. Furthermore, viability of the one single MDA-MB-231 cell in the ACA@AH microcapsule is greater than 90% (FIG. 10A) and the cell could attach and proliferate on the regular cell culture plate after releasing them out of the microcapsules by dissolving the alginate hydrogel in the microcapsules with an isotonic solution of sodium citrate and pipetting (FIG. 10B). The one single cell cultured in each of the ACA@AH microcapsule in CSC medium (1csc culture) could form a cell colony (note: we use the term colony only for spheroid grown from one cell) in 21 days (FIG. 1E). The cell proliferates slowly during the first and the last 7 days, but fast during days 7-14 (FIG. 10C). Unlike the MDA-MB-231 cell aggregates obtained from the conventional ULAP culture (Ucells, FIG. 1E) that easily dissociate into single cells after pipetting for 5 times, colonies obtained from the 1csc culture are stable even after dissolving the microcapsules with sodium citrate and pipetting for 10 times (FIG. 10D). Importantly, only ~4.4% of the MDA-MB-231 cells under the 1csc culture could survive and proliferate to form a colony (FIG. 1F). However, essentially no colonies could be observed either in the absence of the ACA coating (A@AH-1) to keep HA inside the microcapsules or without HA in the core alginate hydrogel scaffold (ACA@A-1), confirming that HA plays a pivotal role in the survival and proliferation of CSCs (FIG. 1F). However, when encapsulating multiple MDA-MB-231 cells in the ACA@AH microcapsules (~10-15 cells per microcapsules, Mcells in short, FIG. 1E), cell spheroids are observed in more than 67% of the microcapsules after only 7 days of culture (FIG. 1F). This suggests the bioinspired use of one single cell is crucial for CSC isolation.

Figure 1G:
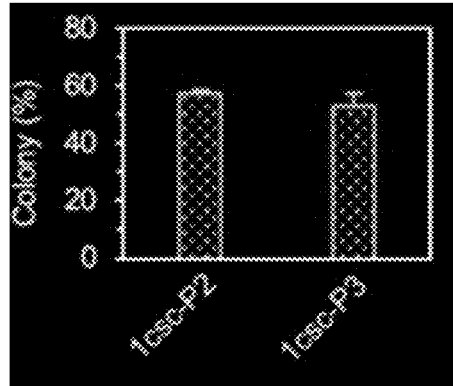
Figure 11:
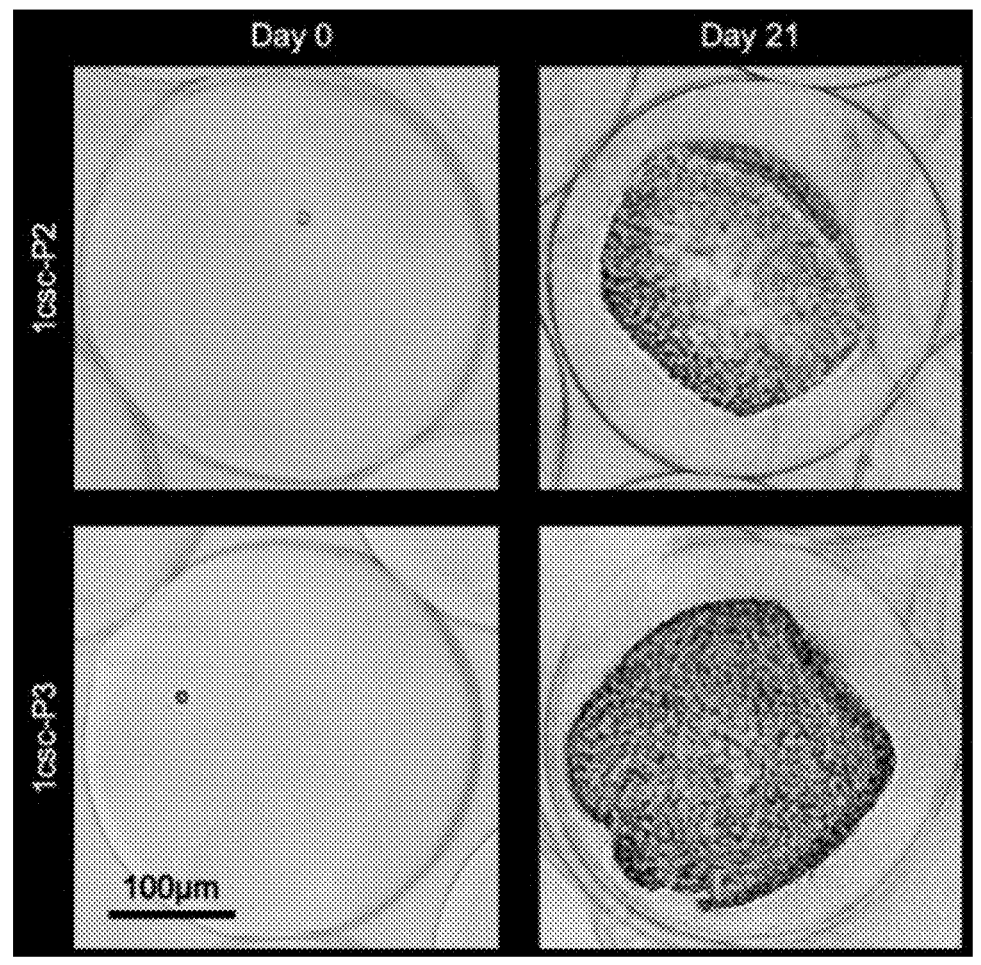
FIG. 11 depicts representative phase contrast micrographs of second-passage (1csc-P2) and third-passage (1csc-P3) colonies formed under the 1csc culture from one single cell. The single cells for making the 1csc-P2 and 1csc-P3 colonies were obtained by dissociating the first-passage 1csc (1csc-Pl that is the 1csc group in FIG.1E-1F) and second-passage (1csc-P2) colonies, respectively.
Figure 12A:
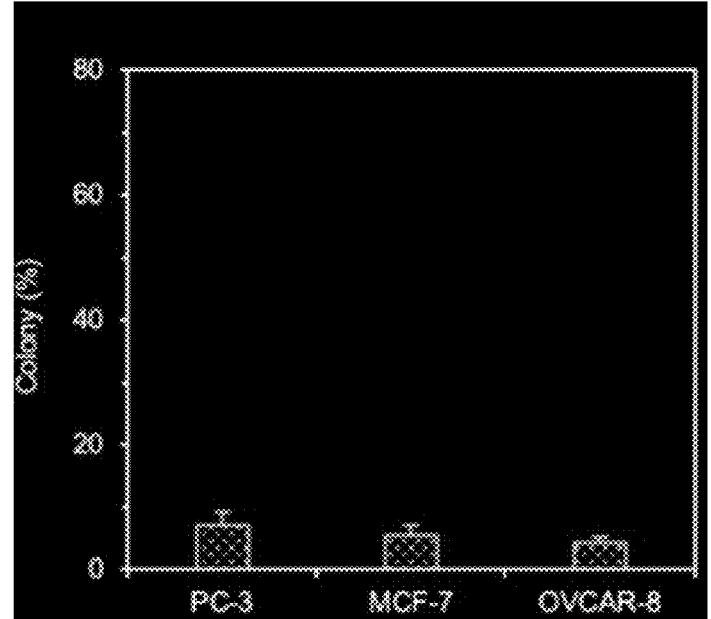
FIG. 12A-12B depict the bioinspired one single cell (1csc) culture method for CSC isolation and culture is applicable to different types of cancer cells.
Figure 12B:
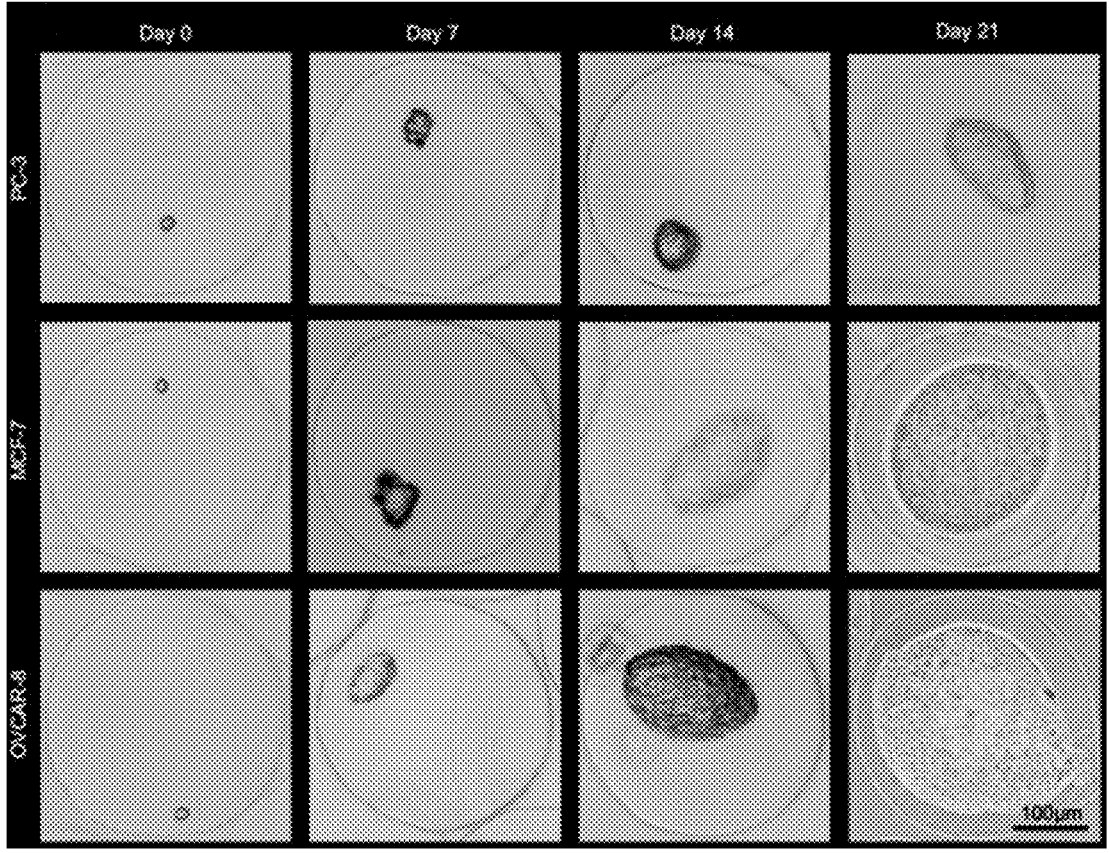

The stemness of the survived cells is then studied with the serial passaging assay first, for which detached cells obtained by dissociating the first-passage 1csc (1csc-Pl or 1csc by default) colonies were encapsulated in the ACA@AH microcapsules (one cell in each microcapsule)

for culture to form the second-passage (1csc-P2) colonies. Strikingly, more than 50% of the encapsulated one single cell can survive and proliferate to form colonies (FIG. 1G and FIG. 11). Similar results are obtained when single cells dissociated from the 1csc-P2 colonies are encapsulated in the ACA@AH microcapsules (one cell in each microcapsule) for culture to form the third-passage (1csc-P3) colonies (FIG. 1G and FIG. 11). These serial passaging data suggest the cells isolated with the one single cell culture method (i.e., 1csc culture) are likely CSCs. The capability of isolating CSCs with the 1csc culture in the ACA@AH microcapsule is further confirmed using PC-3, MCF-7, and OVCAR-8 cells: approximately 7.0, 5.5, and 4.2% of the cells under the 1csc culture are able to survive and proliferate into colonies, respectively (FIG. 12).

ii. Gene and Protein Expression Analyses

Figure 2A:
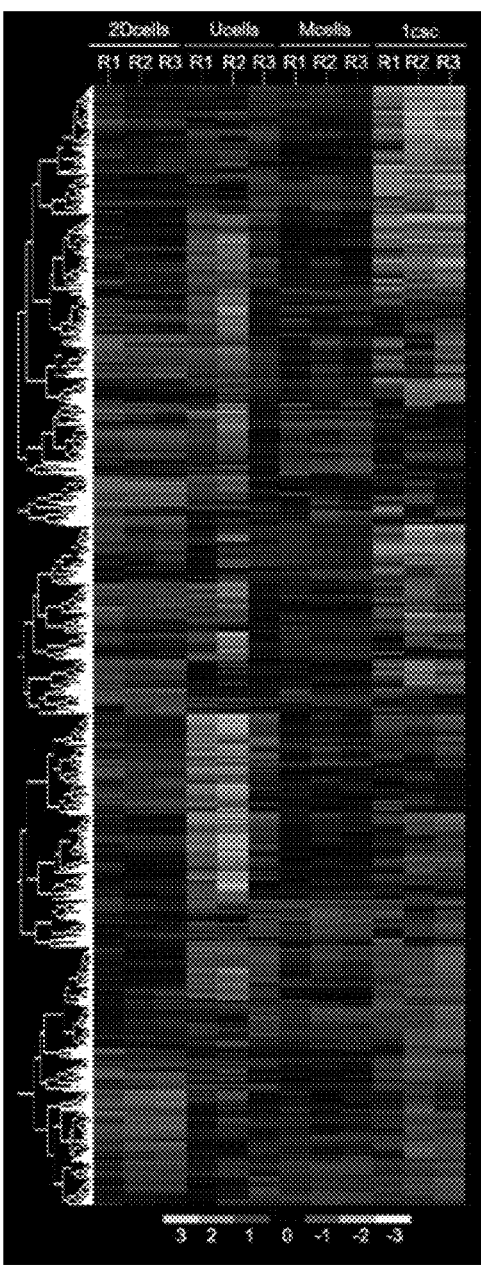
FIG. 2A-2F depict the characterization of stemness with gene and protein expressions.
Figure 2B:
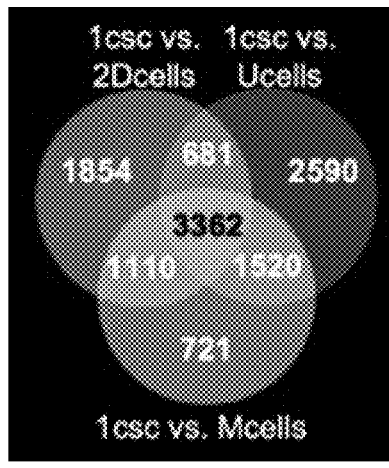

To gain a transcriptome-wide perspective of alterations in cellular characteristics including stemness in response to different methods for CSC isolation, we performed RNA sequencing (RNA-Seq) analyses on the cells in the colonies, spheroids, and aggregates obtained from the 1csc, Mcells, and Ucells culture of MDA-MB-231 cells in CSC medium, together with cells under 2D culture in non-CSC (or regular) medium (2Dcells, FIG. 1E). Results obtained from RNA-Seq were further validated by performing RT-PCR for six differentially expressed genes: ABCG2, CD24, FASN, CD44, MUCI and NDUFA1. First, we confirmed correlation between the four sets of experiments by developing a Pearson correlation matrix. All the triplicates are tightly and positively correlated (the diagonal of the heat map, correlation value: 0.97-0.99) and the four culture methods also exhibit high degree of positive correlation (>0.93). This is not surprising as the cells studied in the four groups are all derived from the same cell line. Next, to identify differentially expressed genes, the volcano plots for the four culture methods are assembled by plotting the negative log10 of the p value on the y-axis, where highly significant changes appear high on the plot. The expression of ~37,000 genes in the cells of the 2Dcells, Ucells, Mcells, and 1csc groups was analyzed. The results show that the 1csc group has the highest number of differentially expressed genes when compared with the other three groups. A clustergram of the top 10,000 genes that are differentially expressed among the four groups is shown in FIG. 2A. In addition, unsupervised hierarchical clustering leads to their organization into distinct clusters. The 1csc group shows significantly greater changes in its transcriptional profiles than the other three groups. Specifically, 7007 (summation of numbers in the red circle), 8153 (summation of numbers in the green circle), and 6713 (summation of numbers in the purple circle) genes were differentially expressed in the 1csc group compared to the 2Dcells, Ucells, and Mcells groups, respectively, as shown by the Venn diagram in FIG. 2B. A total of 3362 genes were differentially expressed in the 1csc group compared to all the other three groups.

Figure 2C:
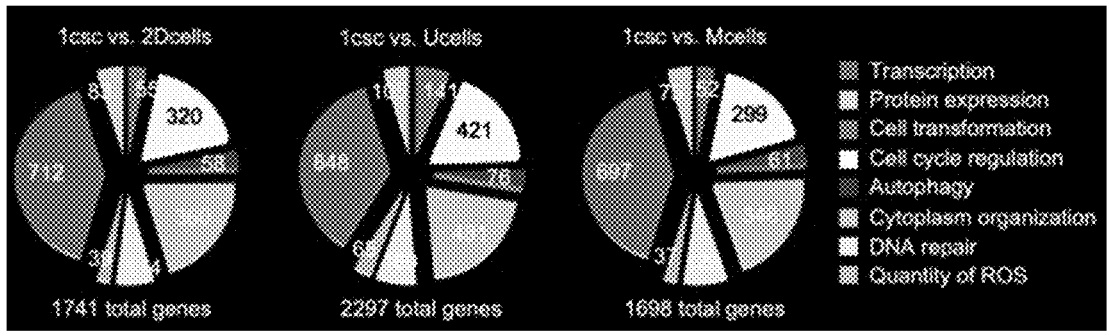
Figure 2D:
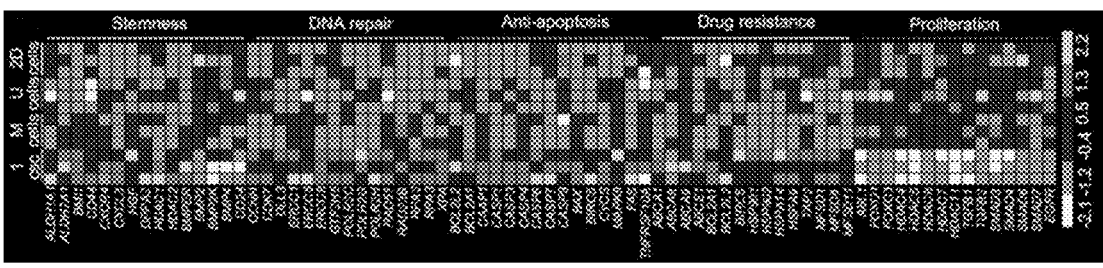
Figure 2E:
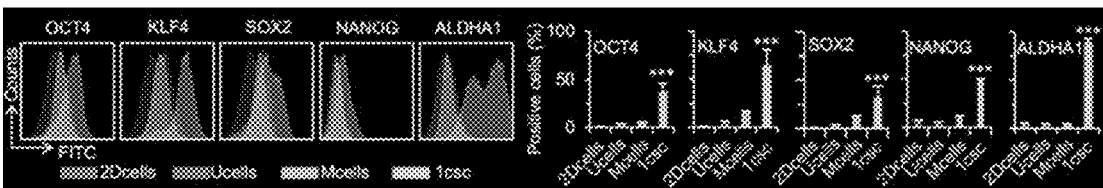
Figure 2F:
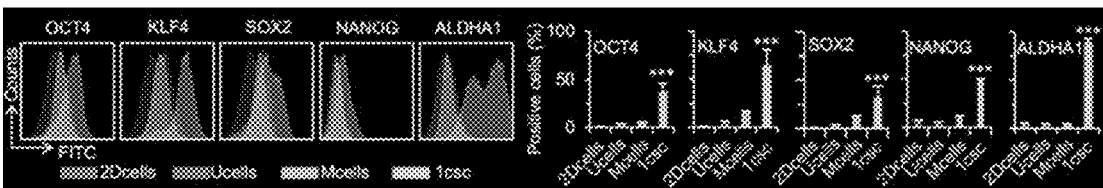

Gene ontology (GO) enrichment analysis was also conducted to determine the significantly altered genes in different biological processes. The top eight enriched GO terms are presented in FIG. 2C. It shows that the biological processes related to cellular structure organization (chromatin organization/transcription, cytoplasm organization, and cell transformation), cell proliferation (cell cycle regulation and autophagy), and cellular stress-related signals (DNA repair and quantity of reactive oxygen species, ROS) are significantly different in the 1csc group compared to all other groups (FIG. 2C). The expression of genes that are relevant to stemness (positive and negative) of CSCs, DNA repair, and anti-apoptosis, and drug in the 1csc group compared to all other groups, is shown in FIG. 2D. Known functional markers of self-renewal (CD44 and BM11) and malignancy (ALDH1A1, ALDH7A1) are significantly upregulated in the 1csc group (FIG. 2D). Expression of genes (CXCR4, CXCL3 and HGF) involved in secretion of chemokines/cytokines in the tumor microenvironment is significantly upregulated in the 1csc group, as well (FIG. 2D). In addition, genes for maintaining pluripotency (e.g., DPPA2, HDAC1, HDAC2, and BMPER) are abundantly expressed in the 1csc group. In contrast, genes (BMP2, BMP2K, BMP4 and CD24) that promote differentiation and cellular proliferation are downregulated in the 1csc group (FIG. 2D. It is worth noting that some key genes (OCT4, SOX2, NANOG, KLF4) important for the maintenance of pluripotency are not upregulated in the 1csc group. However, the expressions of these proteins are high in the 1csc group according to the confocal microscopy (FIG. 2E) and flow cytometry analyses with immunofluorescence staining (FIG. 2F). This is probably because the translation of mRNAs into proteins is regulated by many post-transcriptional processes in cells.[17] Indeed, further analyses indicate that many repressors and activators associated with these four stemness genes are downregulated and upregulated, respectively, in the 1csc group. This may contribute to the increase in the activity of the four proteins in the 1csc group. The stemness of the cells in the 1csc group is also indicated by the increased expression of two other commonly used stemness markers, ALDHA1 and alkaline phosphatase (AP), compared with the other three groups (FIG. 2E). The capability of CSCs to survive in stressful conditions is correlated to high expression of anti-apoptotic markers as well as protection of genome integrity by prompt activation of DNA damage sensor and repair machinery.[18] Indeed, many DNA repair-related genes including the CCDH, ERCC, POLR2, RPA families, are upregulated in the 1csc group compared with the other three groups (FIG. 2D). In addition, the expressions of anti-apoptotic genes (e.g., the BCL2L2 and CAP families) are significantly higher in the 1csc group than the other three groups (FIG. 2D). Cells in the 1csc group also express elevated levels of drug-transporter proteins (e.g., the ABCA1, ABCA8, HSP90 families) to expel cytotoxic agents (FIG. 2D), which may lead to high resistance to chemotherapeutic drugs. CSC quiescence has also been hypothesized to protect the cells against cytotoxic therapy.[19] Indeed, many proliferation genes are downregulated in the 1csc group (e.g., ABL1, FOXO1, and FOXO3) compared with the other three groups (FIG. 2D).

iii. Cross-Tissue Multilineage Differentiation

Figure 3A:
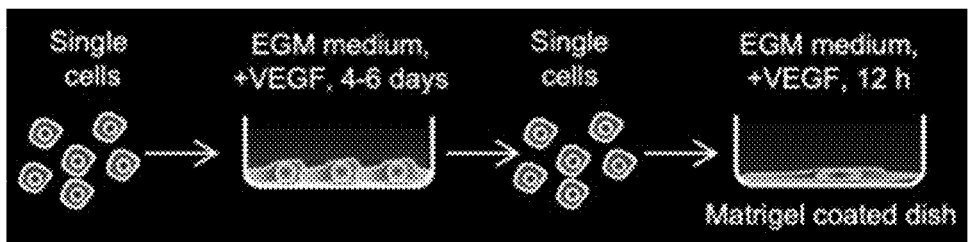
FIG. 3A-3I depict the characterization of stemness with multilineage differentiation.
Figure 3B:
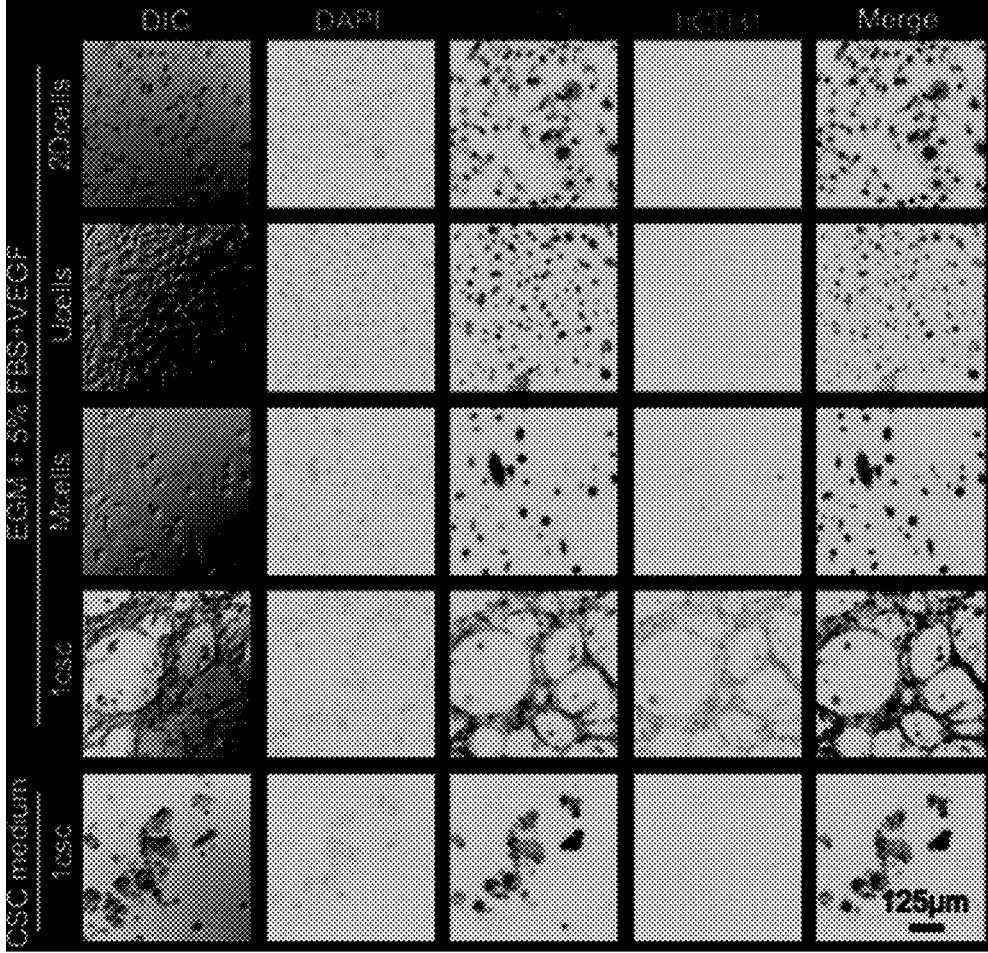
Figure 13:
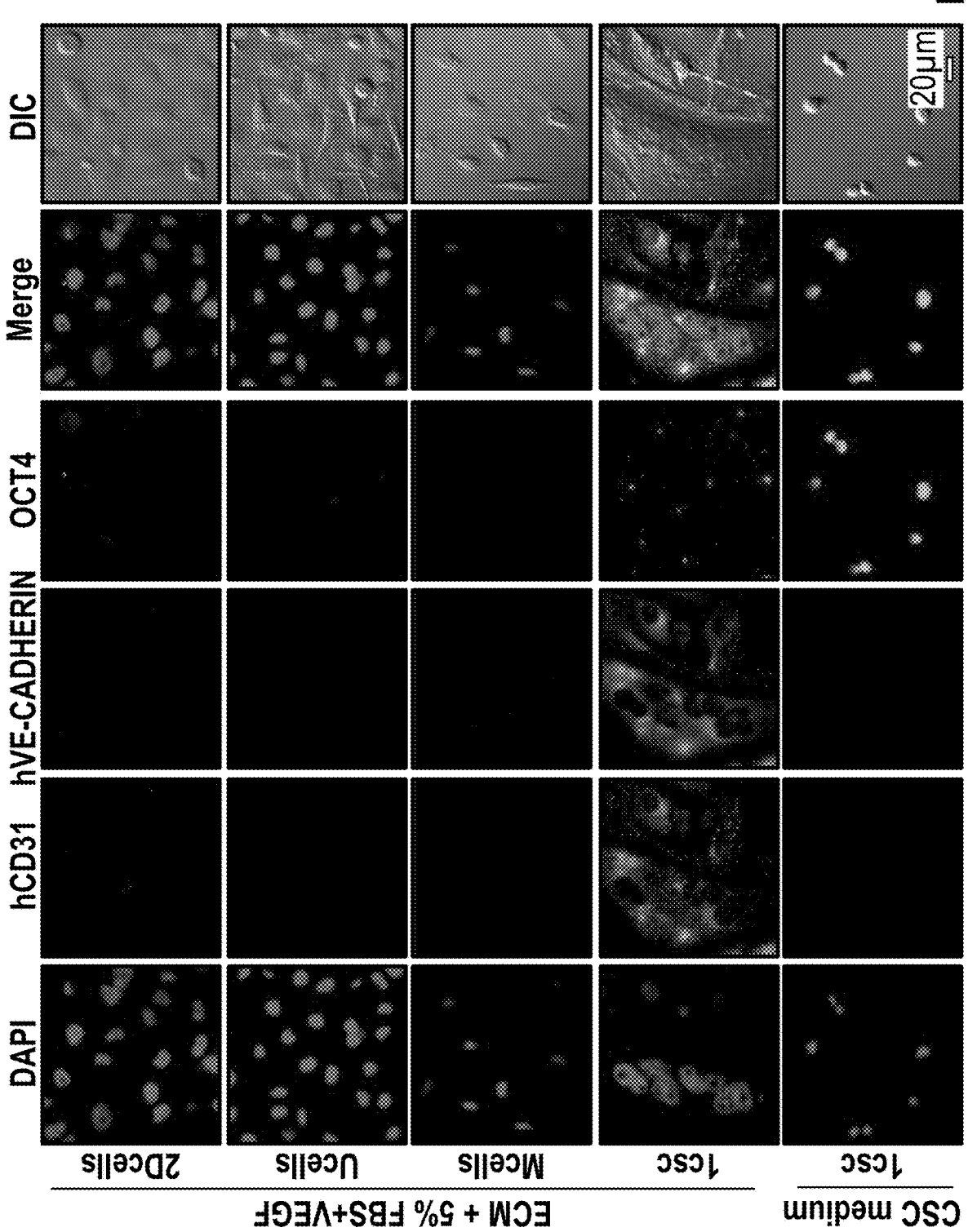
FIG. 13 depicts confocal micrographs of endothelial differentiation showing the expression of human CD31 (hCD31) and human VE-CADHERIN (hVE-CADHERIN) in the cells differentiated from the 1csc colony cells. At the same time, the expression of OCT4 in the differentiated 1csc colony cells is downregulated. In contrast, the 1csc colony cells cultured in CSC medium do not express the two endothelial markers and has high expression of OCT4. All the three protein markers are negligible in the differentiated cells of the 2Dcells, Ucells, and Mcells groups.
Figure 14:
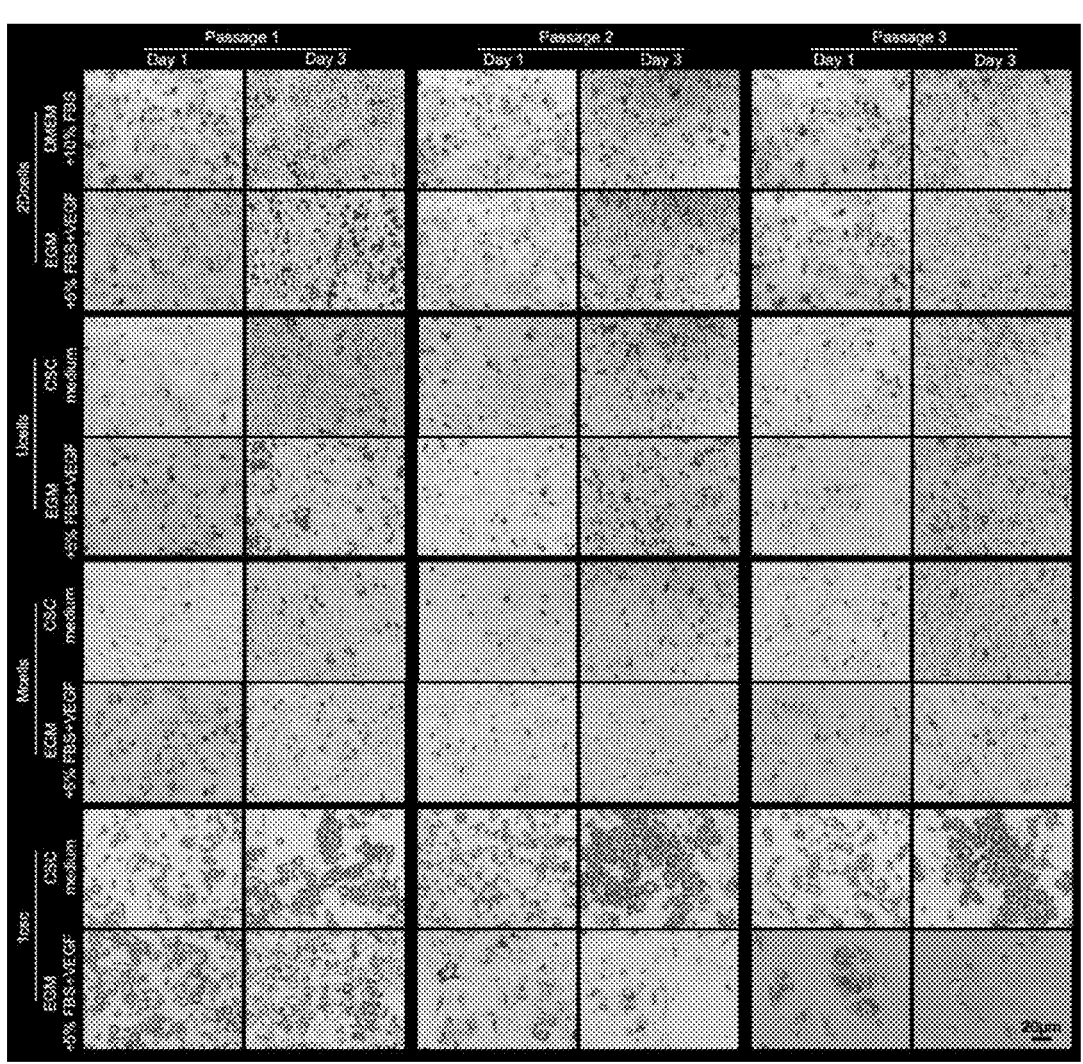
FIG. 14 depicts phase contrast micrographs of cells from the 2Dcells, Ucells, Mcells, and 1csc groups during culturing in CSC medium, endothelial growth medium (EGM) supplemented with 5% FBS and 50 ng ml$^{-1}$ VEGF, or DMEM supplemented with 10% FBS (for 2Dcells only) for up to 3 passages, showing cells from the 2Dcells, Ucells, and Mcells groups proliferate through passage 3. In contrast, most of the cells from the 1csc group cannot survive after the second passage although they survive well in the CSC medium. It is also observed that cells from the 1csc group tend to form aggregates when cultured in the CSC medium.

Besides the expression of stemness genes and proteins, a crucial characteristic of stem cells is their capability of cross-tissue multilineage differentiation.[20] The MDA-MB-231 cells cultured with the aforementioned four methods were then investigated for their capacity of endothelial, cardiac, osteogenic, and neural differentiation. For endothelial differentiation, the cell colonies/spheroids/aggregates were dissociated and the 2D cultured cells were detached into single cells for culture in endothelial growth medium (EGM) supplemented with 50 ng ml$^{-1}$ vascular endothelial growth factor (VEGF) for 4-6 days. Immunostainings of human CD31 and VE-cadherin indicate that the cells derived from the 1csc group express significantly higher levels of the two endothelial cell markers compared with cells derived from the other three groups (FIG. 13). The expression of endothelial cell markers is minimal when the cells obtained from the 1csc colonies are cultured in the CSC medium, while the expression of OCT4 is stronger in the 1csc colony cells cultured in the CSC medium than the differentiation medium (FIG. 13). Moreover, the cells differentiated from the 1csc group are able to self-assemble into blood vessel-like structures after seeded on Matrigel in differentiation medium for 12 hours (FIG. 3A-3B). These data indicate functional endothelial cells can be differentiated from the 1csc colony cells. In stark contrast, no blood vessel formation is observable when culturing the cells from the 2Dcells, Ucells, and Mcells groups on Matrigel in endothelial differentiation medium or the 1csc colony cells in CSC medium on Matrigel. It is worth noting that cells from the 2Dcells, Ucells, and Mcells groups could attach and proliferate efficiently in culture medium or differentiation medium at least for three passages (FIG. 14). In contrast, the 1csc colony cells tend to form cell aggregates and most of them do not attach on the cell culture plate during passage 1. Surprisingly, starting from passage 2, the differentiated cells in the 1csc group could not proliferate and further passaging causes the cells to die and few cells could survive to passage 3 (FIG. 14). These data suggest the 1csc colony cells lose their cancerous property after endothelial differentiation and using VEGF to induce CSC endothelial differentiation might be a valuable strategy for cancer therapy. This may also contribute to the observation that VEGF inhibitor-based cancer therapy is at times associated with cancer drug resistance.[21]

Figure 3C:
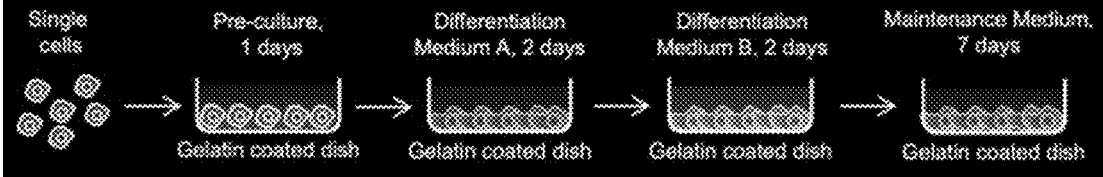
Figure 3D:
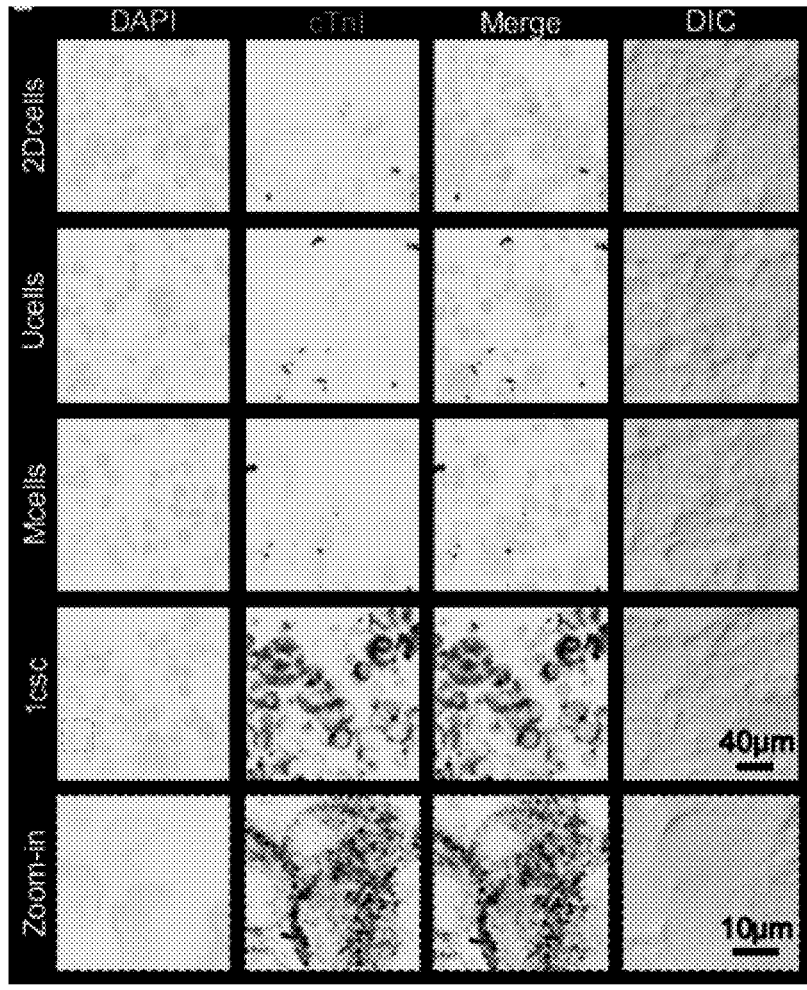
Figure 3E:
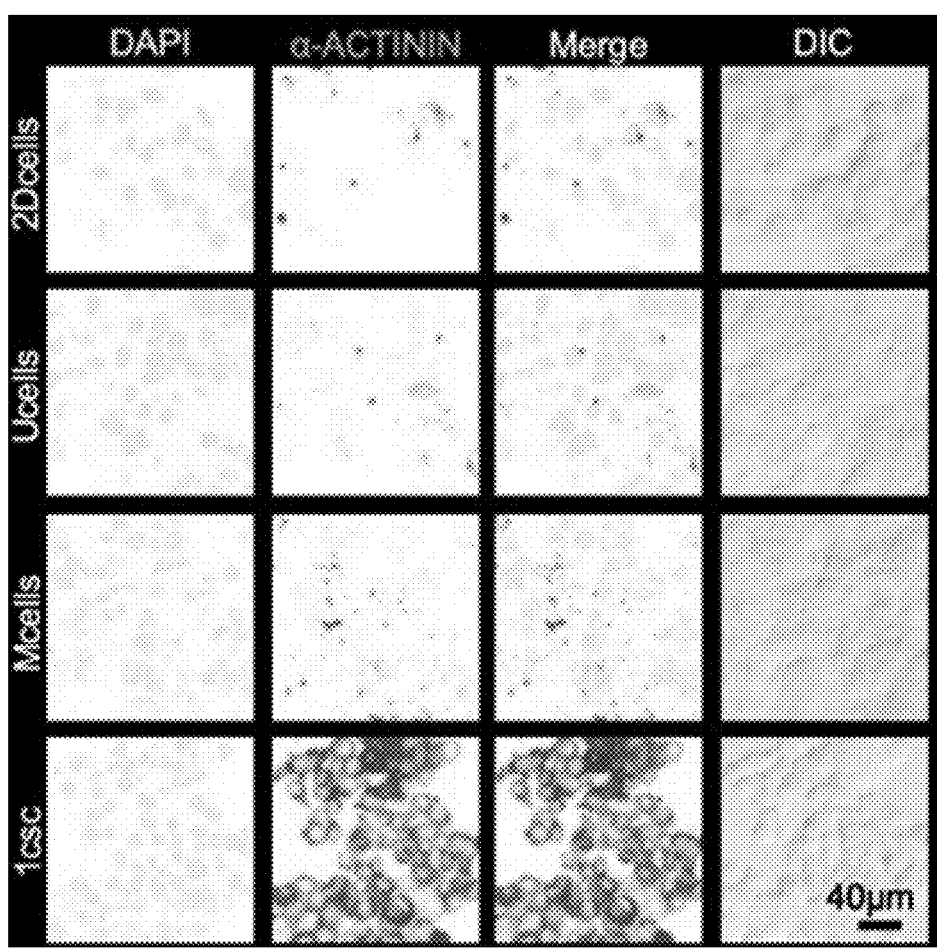
Figure 3F:
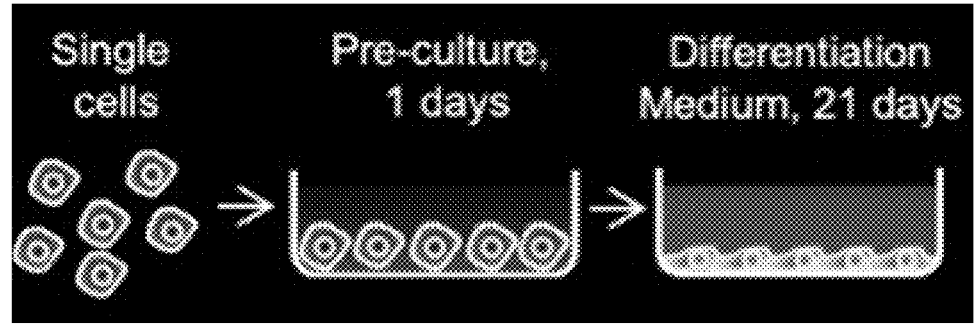
Figure 3G:
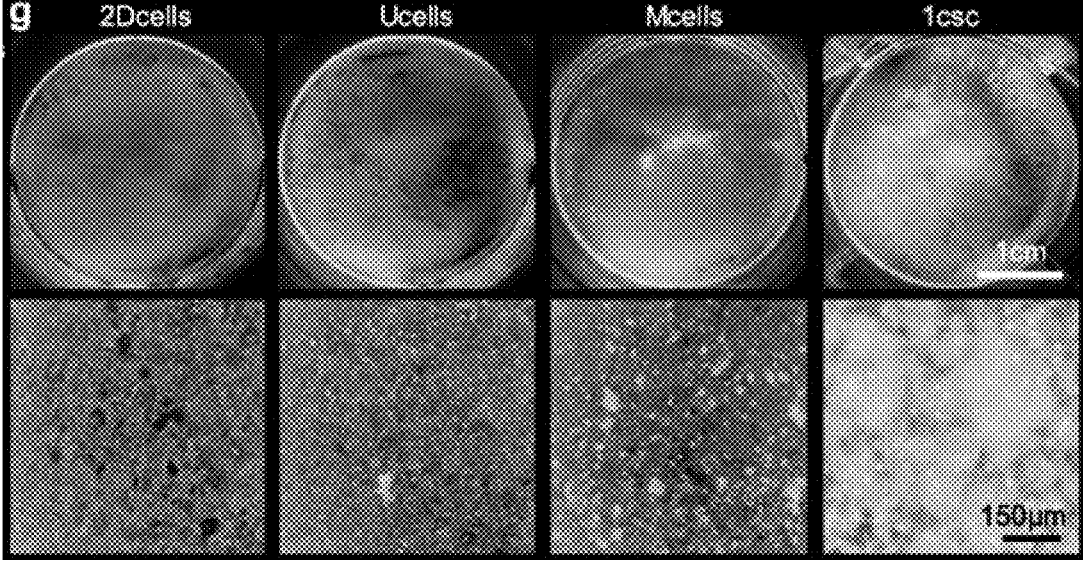
Figure 3H:
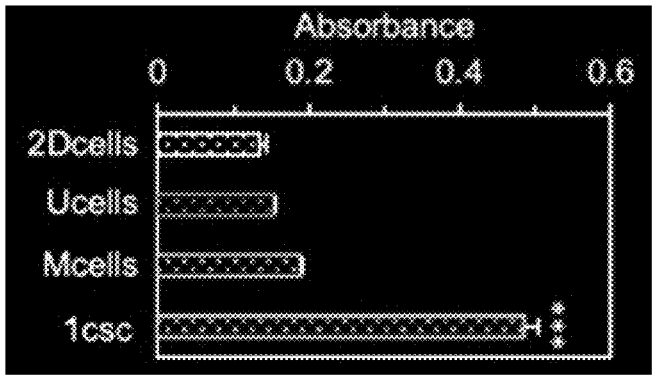
Figure 3I:
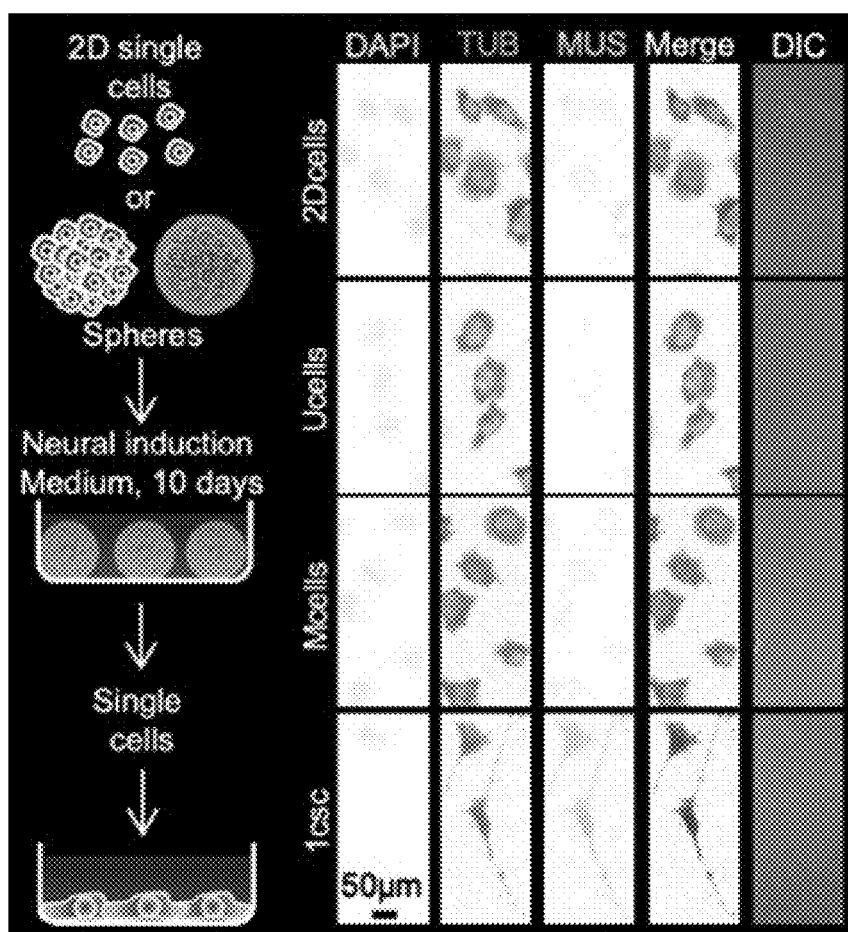
Figure 15:
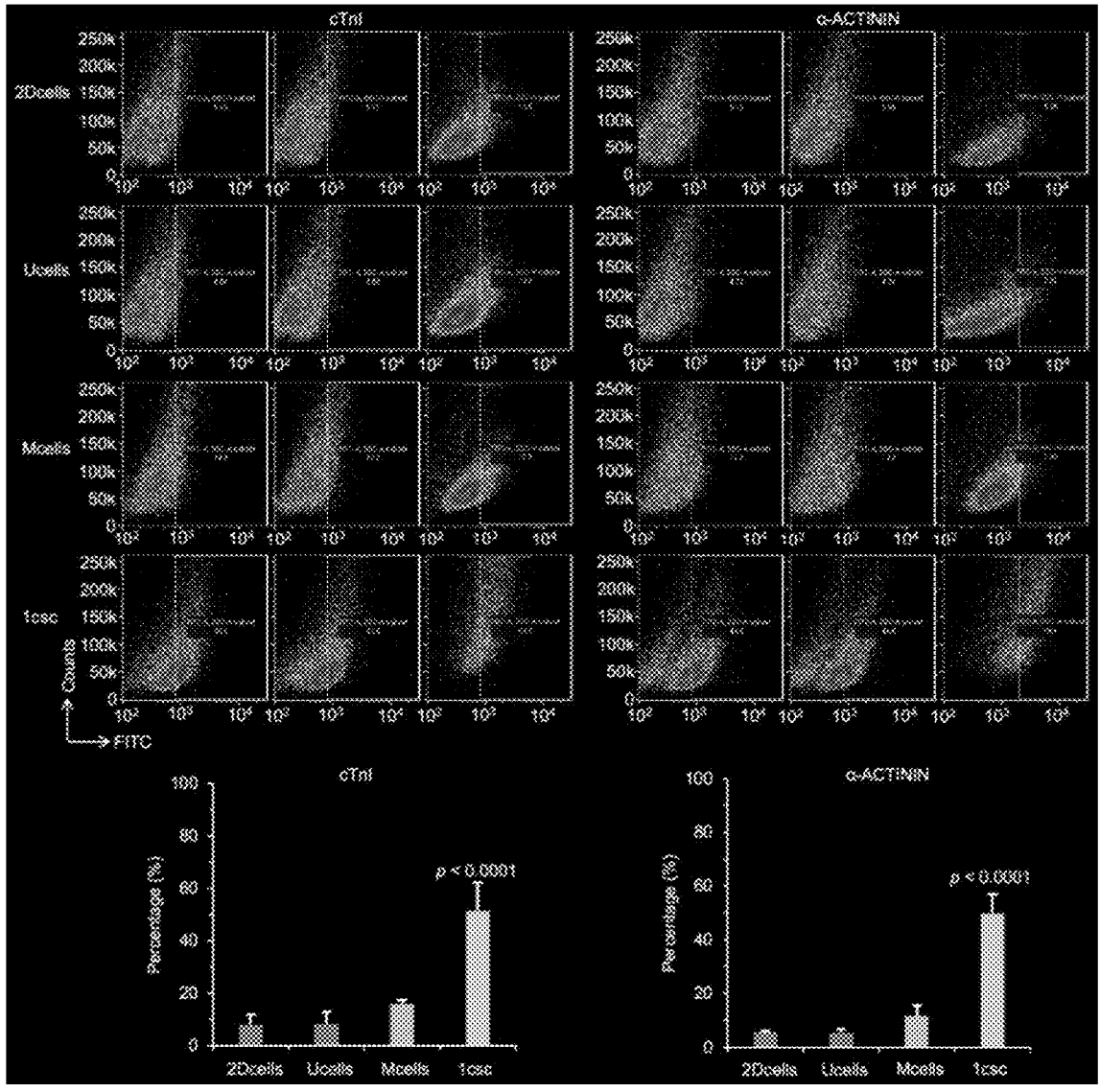
FIG. 15 depicts cardiac specific markers (cTnI and a-AC-TININ) are highly expressed in cells after cardiac differentiation in the 1csc group in comparison to the 2Dcells, Ucells, and Mcells groups. Flow cytometry of three independent runs and quantitative results show significantly higher expression of the cardiac specific markers in the 1csc group than the 2Dcells, Ucells, and Mcells groups. Error bars denote mean±s.d., and statistical significance was assessed by one-way ANOVA with post hoc Tukey test.
Figure 16:
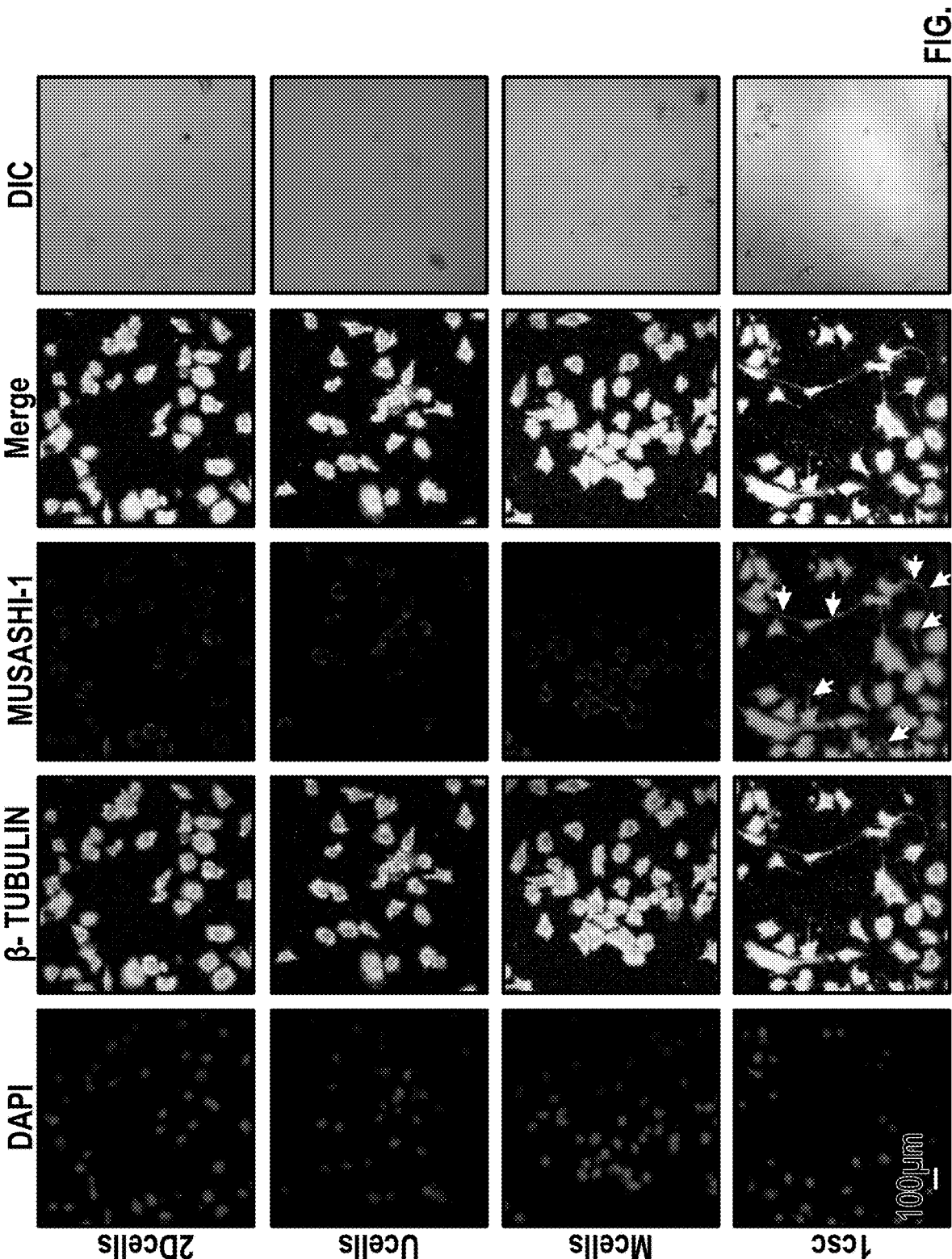
FIG. 16 depicts confocal micrographs of the cells from the 2Dcells, Ucells, Mcells, and 1csc groups after neural differentiation show significantly higher expression of the neural specific marker MUSASHI-1 in the 1csc group than the other three groups. The B-TUBULIMN was stained to show the cytoskeleton of the cells. White arrows indicate neurites of the differentiated cells, which could be seen only in the 1csc group.

We further conducted cardiac differentiation on the cells obtained from the four different cultures using a two-step differentiation assay from Thermo Fisher according to the manufacturer's instructions (FIG. 3C). Although we did not observe spontaneously beating cardiomyocytes, the immunostaining data show that high expression of multiple cardiac specific markers including cardiac troponin I (cTnI) and α-ACTININ can be observed only for the 1csc group (FIG. 3D-3E and FIG. 15). Osteogenic differentiation was also conducted by utilizing a kit from Thermo Fisher as per the manufacturer's instructions FIG. 3F) and staining of calcium deposits with Alizarin Red S was used to judge successful osteogenic differentiation.[22] As shown in FIG. 3G-3H, significantly more calcium deposits could be observed in the 1csc group than the other three groups. Similarly, neural marker (MUSASHI-1 or MUS staining) and neurite-like structure could be observed only for the 1csc group after neural differentiation (FIG. 3I and FIG. 16). All the aforementioned differentiation studies indicate that only the 1csc colony cells possess the capability of multilineage differentiation, indicating they are CSCs. Cells obtained from the conventional Mcells, Ucells, and 2Dcells cultures may not be CSCs because they lack the key feature of multilineage differentiation for stem cells.

iv. In Vivo Tumorigenesis

Figure 4A:
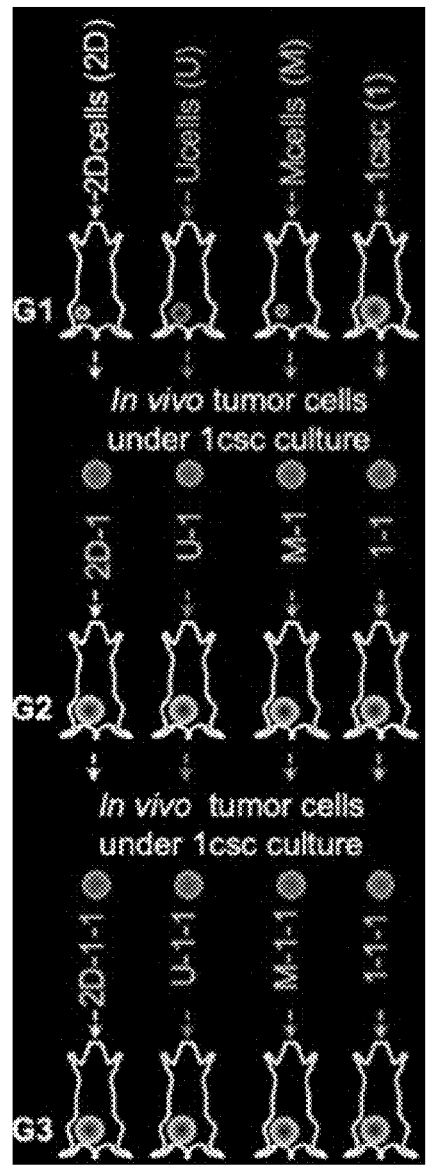
FIG. 4A-4O depict the characterization of stemness with multi-generation tumorigenesis assay in vivo.
Figure 4B:
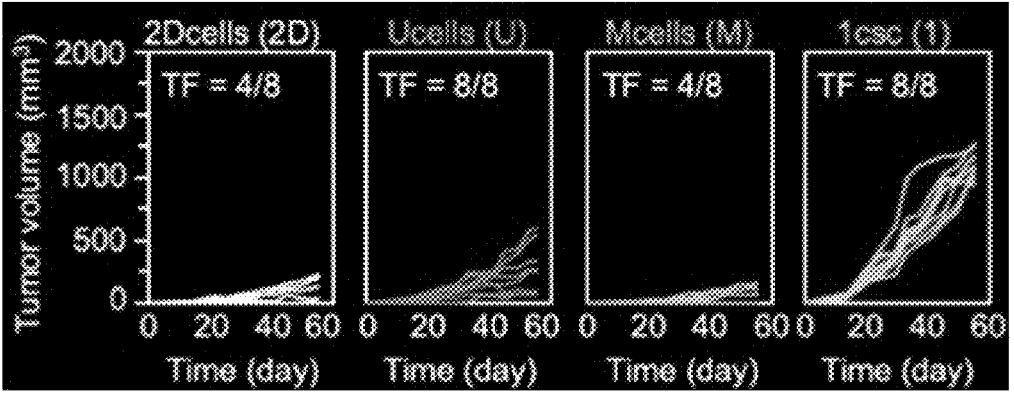
FIG. 4B-4C: Individual growth curves of the G1 tumors (2D, U, M, and 1) in 55 days (FIG. 4B) and weight of the G1 tumors on day 55 (FIG. 4C) for the four groups. The p value for the 1csc (1) group versus the 2Dcells (2D), Ucells (U), and Mcells (M) groups is <0.0001. Statistical significance was assessed by one-way ANOVA with post hoc Tukey test. * $p < 0.001$.
Figure 4C:
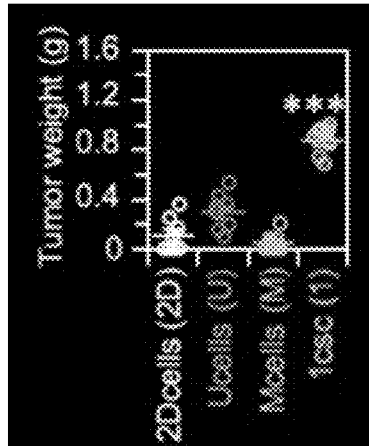
Figure 4D:
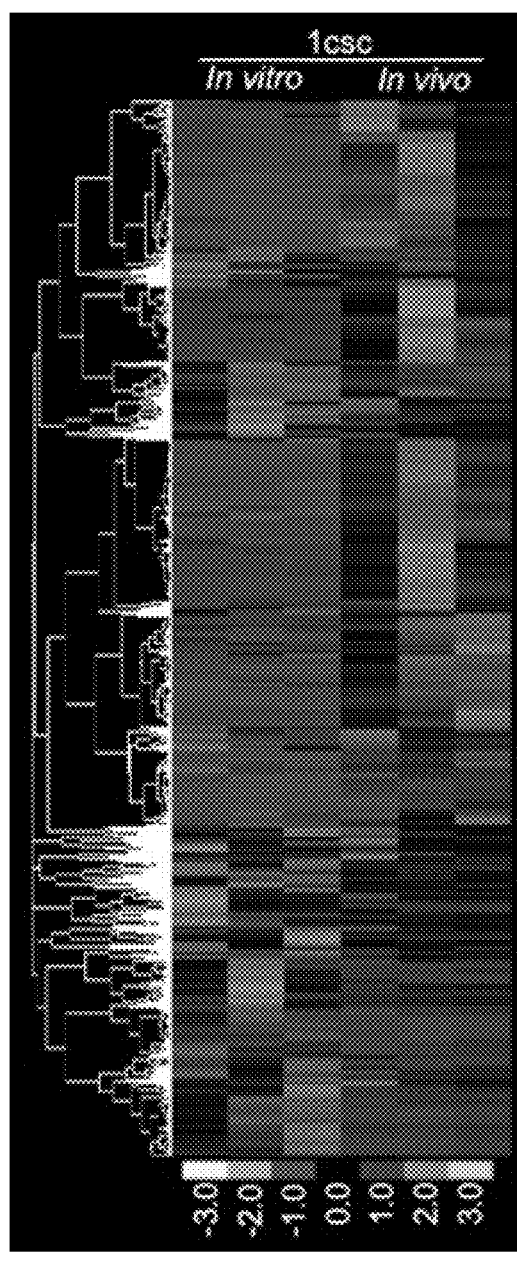
FIG. 4D: Differential gene expression heat map from RNA-Seq analysis of cells in the 1csc group before injection into mice (in vitro) and cells in tumor (in vivo) grown from the 1csc in vitro cells.
Figure 4E:
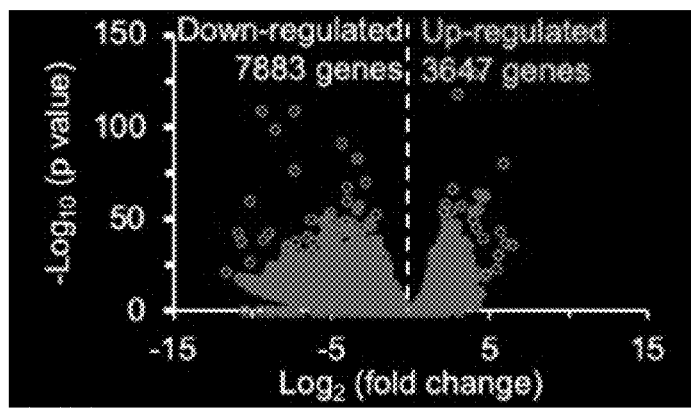
FIG. 4E: The distribution of down-and up-regulated genes in the in vivo cells as compared to the in vitro cells in the 1csc group.
Figure 4F:
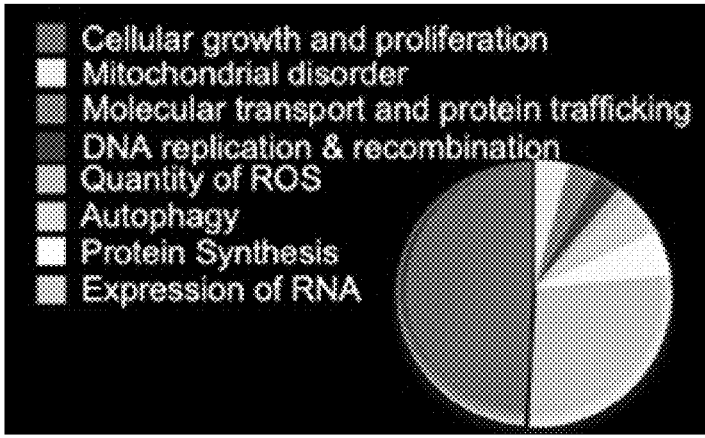
FIG. 4F: Pathway analysis of significantly altered genes in the 1csc in vivo cells as compared to the 1csc in vitro cells. The whole-genome data are representative of three independent experiments.
Figure 4G:
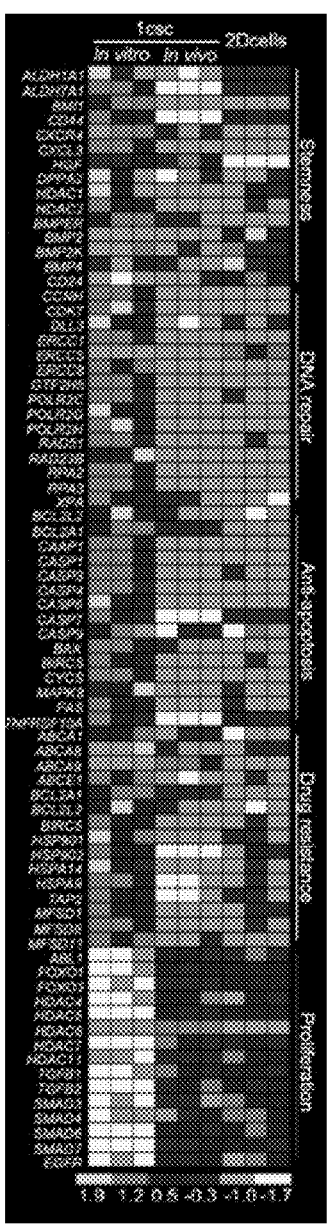
FIG. 4G: Heat map of gene expression in the 1csc in vitro and in vivo cells together with in vitro 2D cultured cells (2Dcells) regarding stemness, DNA repair, anti-apoptosis, drug resistance, and cell proliferation. The gene expression of 1csc in vivo cells is closer to that of cells in the 2Dcells group than 1csc in vitro cells.
Figure 4H:
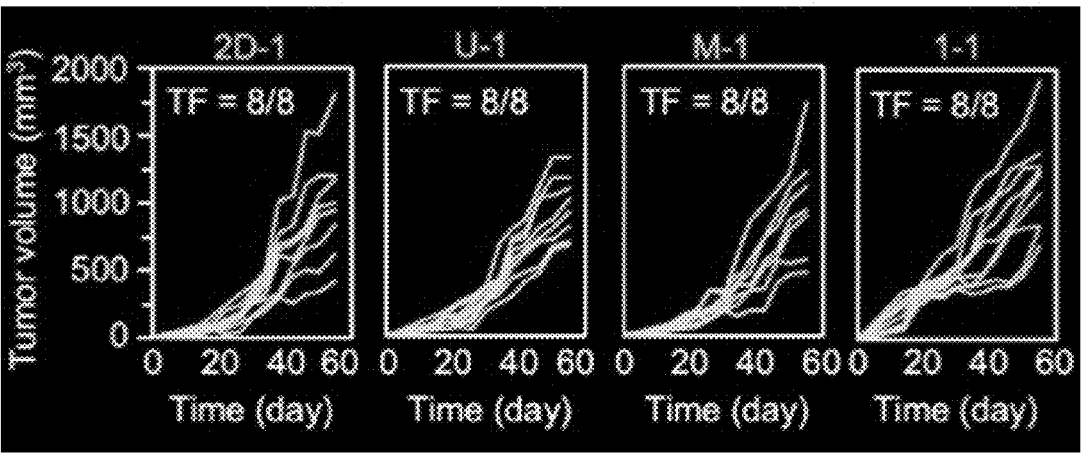
FIG. 4H-4I: Individual growth curves of G2 tumors (2D-1, U-1, M-1, and 1-1) in 55 days (FIG. 4H) and weight of the G2 tumors on day 55 (FIG. 4I) for the four groups.
Figure 4I:
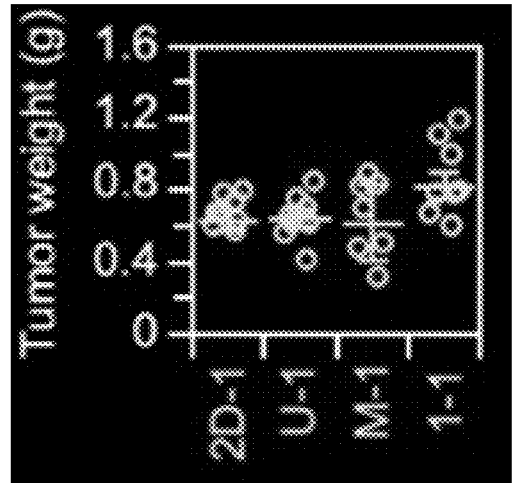
Figure 4J:
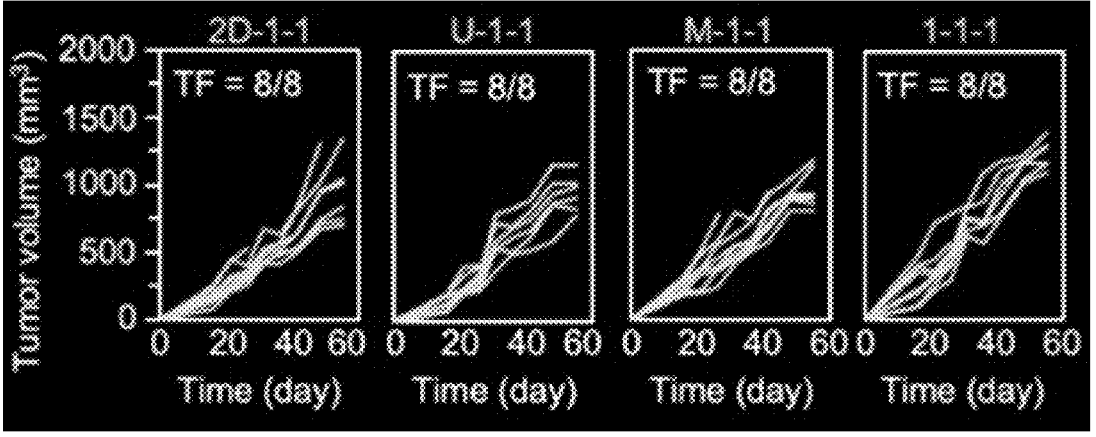
FIG. 4J-4K: Individual growth curves of G3 tumors (2D-1-1, U-1-1, M-1-1, and 1-1-1) in 55 days (FIG. 4J) and weight of the G3 tumors on day 55 (FIG. 4K) for the four groups.
Figure 4K:
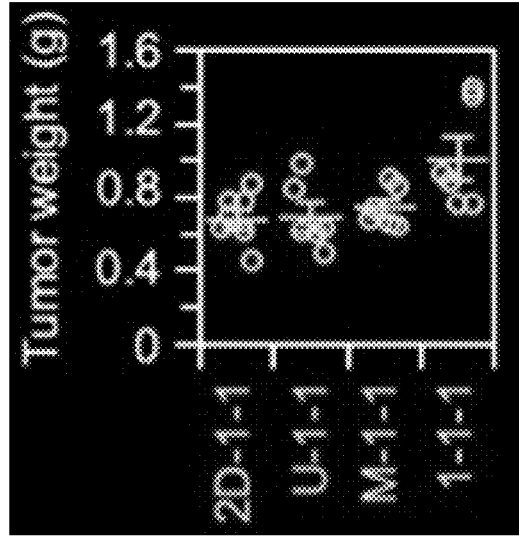
Figure 17:
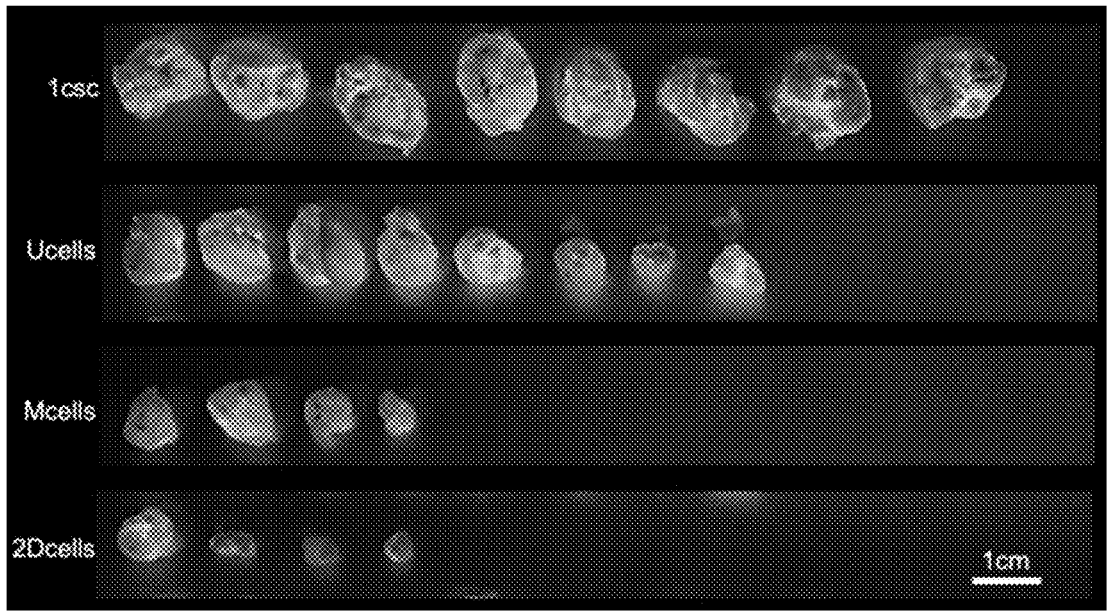
FIG. 17 depicts photographs of tumors obtained on day 55 isolated from in vivo tumors. Photographs showing significantly larger tumors in the 1csc group than the other three groups. Tumor formation occurs in all the eight mice of the 1csc and Ucells groups, but it occurs in only 4 of the eight mice for both the 2Dcells and Mcells groups.

After confirming the stemness of the 1csc colony cells in vitro, we investigated the in vivo tumorigenic capability of the colony cells as compared to cells from the 2Dcells, Ucells, and Mcells groups. As schematically illustrated in FIG. 4A, three generations (G1-G3) of tumors were produced: the first generation (G1) tumors were generated using cells obtained from the MDA-MB-231 cells under 2Dcells (2D), Ucells (U), Mcells (M), and 1csc (1) cultures by injecting them into the mammary fat pads of immunodeficient mice; cells isolated from the G1 tumors (2D, U, M, and 1) of the four groups were then under the 1csc culture to obtain colony cells for injecting into the fat pads of immunodeficient mice to generate the second generation (G2) tumors (2D-1, U-1, M-1, and 1-1); and cells were again isolated from the G2 tumors and further cultured using 1csc method to obtain colony cells for injecting into the fat pads of immunodeficient mice to generate the third generation (G3) tumors (2D-1-1, U-1-1, M-1-1, and 1-1-1). A total of 500 cells were injected into each mouse and the tumor growth was monitored for 55 days. Due to the small number of cells used for injection into each mouse, G1 tumor formation was observed in only 4out of the 8 mice (TF=4/8) for the 2Dcells and Mcells groups (FIG. 4B-4C and FIG. 17). Although the G1 tumor formation does occur in 8 out of 8 mice (TF=8/8) for both the Ucells and 1csc groups, the G1 tumors in the 1csc group grow much faster and are much bigger than that in all the other three groups. Interestingly, we do not observe any significant difference in tumor growth among the Ucells, Mcells, and 2Dcells groups, indicating the inability of the conventional methods for isolating CSCs (at least for the MDA-MB-231 cells and tumor cells derived from the cells). To check the difference in transcriptome profile of the 1csc colony cells before (in vitro) versus after (in vivo) injection into mice, we performed RNA-Seq on cells isolated from the G1 tumors in the 1csc group. All the triplicates correlate very well. Interestingly, many genes were differentially expressed between the in vitro 1csc colony cells and the cells of the in vivo tumors grown from the in vitro 1csc colony cells, as shown in the clustergram of the top 11,530 genes (FIG. 4D). Specifically, 7883 genes are significantly downregulated whereas 3647 genes are significantly upregulated after injecting the in vitro 1csc colony cells into mice to grow in vivo tumors (FIG. 4E). We further found that almost half of the upregulated genes in in vivo tumors were related to cellular growth and proliferation, suggesting that cellular proliferation of the 1csc colony cells is significantly altered after in vivo injection probably due to their spontaneous differentiation into tumor cells in vivo (FIG. 4F). Additionally, the expression of most of the genes related to stemness, DNA repair, anti-apoptosis, and drug resistance is significantly decreased in in vivo tumors compared to the in vitro 1csc colony cells and is similar to that in the 2D cultured cells (2Dcells, FIG. 4G).

Figure 18A:
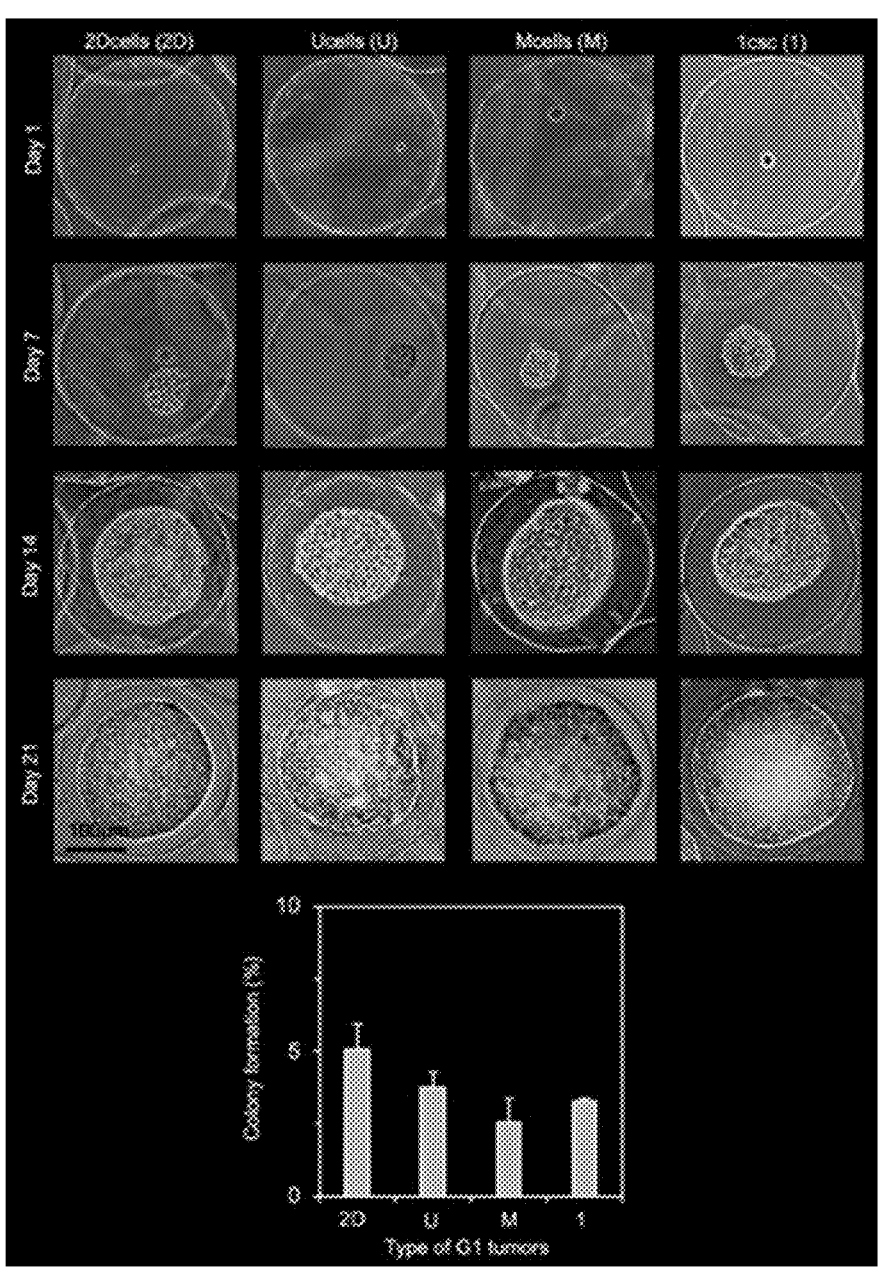
FIG. 18A-18B depict one single cell microencapsulation of cells isolated from in vivo tumors for 1csc culture.
Figure 18B:
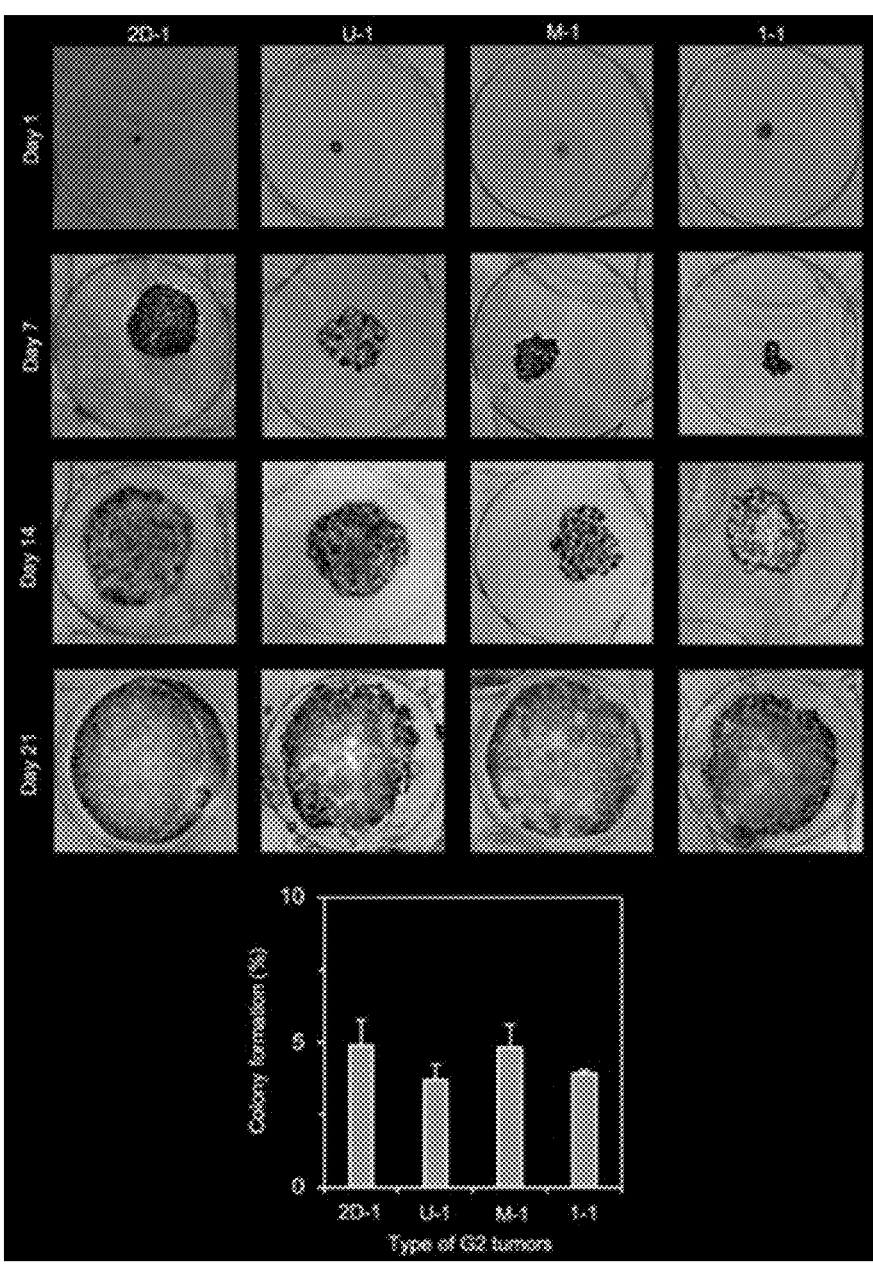

In order to examine if the 1csc culture approach can be used to isolate CSCs from in vivo tumors, cells from the G1 in vivo tumors of the four different groups (2D, U, M, and 1) were isolated and cultured using the 1csc approach with one single cell in each ACA@AH microcapsule in CSC medium. Interestingly, only ~3-5% of the tumor cells are able to form colonies for all the four groups (FIG. 18A). Furthermore, all the 1csc colony cells obtained from the four groups are able to form the G2 (2D-1, U-1, M-1 and 1-1) in vivo tumors in the mouse mammary fat pads efficiently (TF=8/8, FIG. 4H-4I and FIG. 19A-19B). Similarly, the G3 in vivo tumor formation was performed by culturing cells from the G2 (2D-1, U-1, M-1 and 1-1) tumors using the 1csc culture to obtain colony cells for injecting into the mouse fat pads. As with cells from the G1 tumors, only ~3-5% of the cells from the G2 tumors could form a colony in each ACA@AH microcapsule (FIG. 18B). Growth of the G3 (2D-1-1, U-1-1, M-1-1 and 1-1-1) tumors (FIG. 4J-4K and FIG. 19C-19D) is similar to that of the aforementioned G2 tumors. Taken together, a total of three generations of in vivo tumorigenesis studies indicate that the colony cells from the 1csc culture are significantly much more tumorigenic than cells derived from the 2Dcells, Mcells, and Ucells cultures. To further confirm this, cells were isolated from the G1 (1) and G2 (1-1) tumors grown from the 1csc colony cells and cultured using the three conventional culture methods (2Dcells or 2D, Ucells or U, and Mcells or M). The resultant cells were injected into the mouse fat pad for generating the second-generation (1-2D, 1-U, 1-M, FIG. 4L-4M) and third-generation (1-1-2D, 1-1-U, and 1-1-M, FIG. 4N-4O) tumors.

Figure 4L:
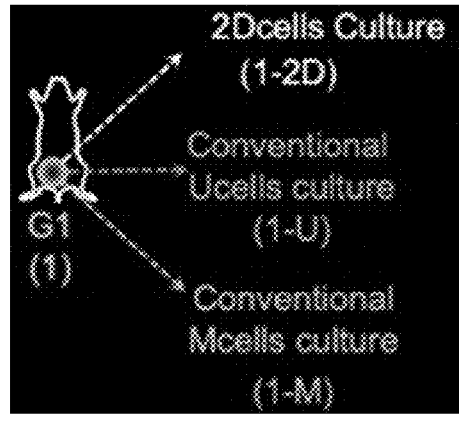
FIG. 4L: A schematic illustration of the second-generation tumors grown from cells obtained by 2Dcells, Ucells, and Mcells cultures of the 1csc G1 tumor cells (left), together with the individual growth curves of the tumors (1-2D, 1-U, and 1-M) (right).
Figure 4M:
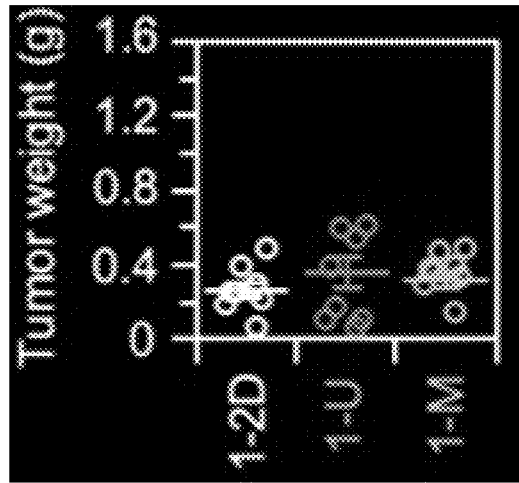
FIG. 4M: Weight of the 1-2D, 1-U, and 1-M tumors.
Figure 4N:
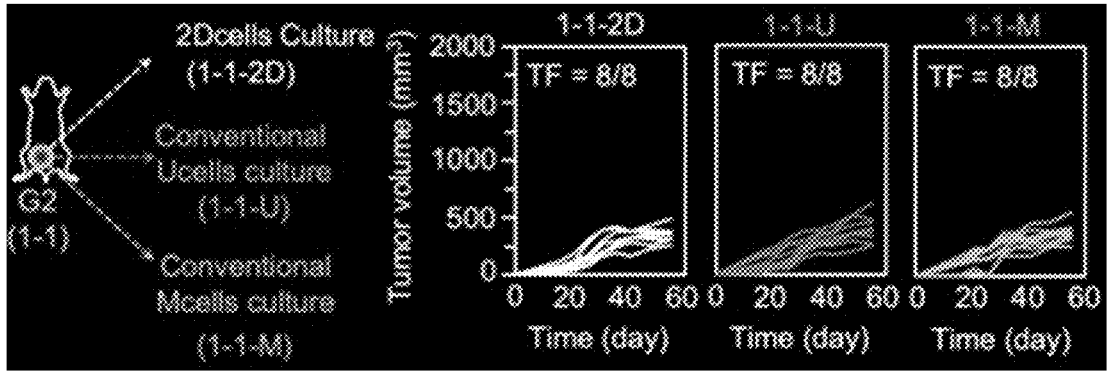
FIG. 4N: A schematic illustration of the third-generation tumors grown from cells obtained by 2Dcells, Ucells, and Mcells cultures of the 1csc G2 tumor cells (left), together with the individual growth curves of the tumors (1-1-2D, 1-1-U, and 1-1-M) (right).
Figure 4O:
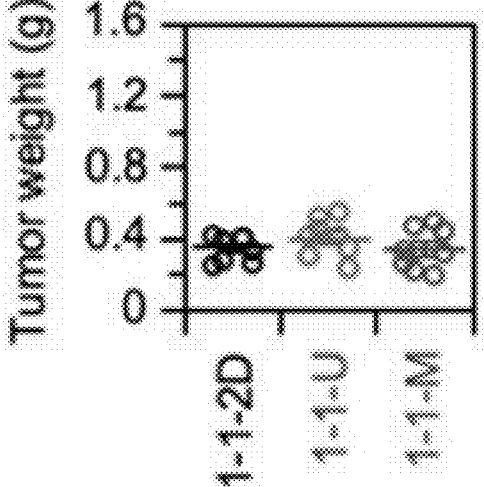
Figure 19A:
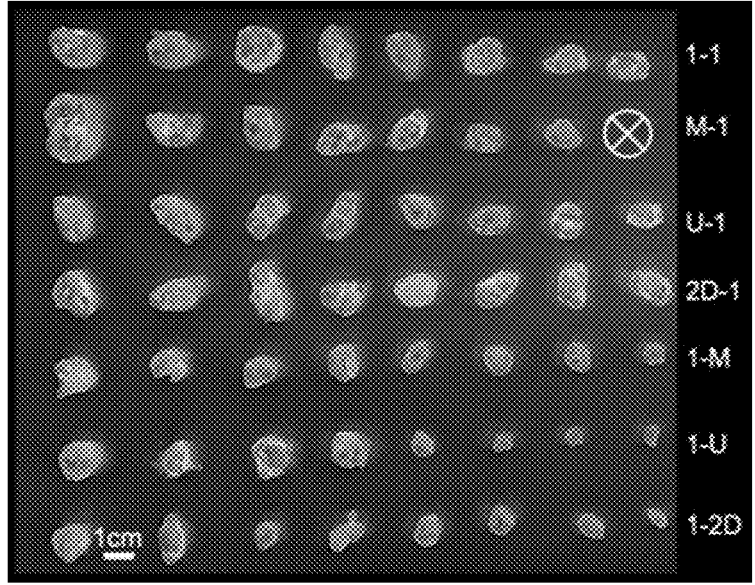
FIG. 19A-19D depict in vivo tumorigenesis of cells obtained by 2Dcells, Ucells, Mcells, and 1csc culture of cells isolated from in vivo tumors.
Figure 19B:
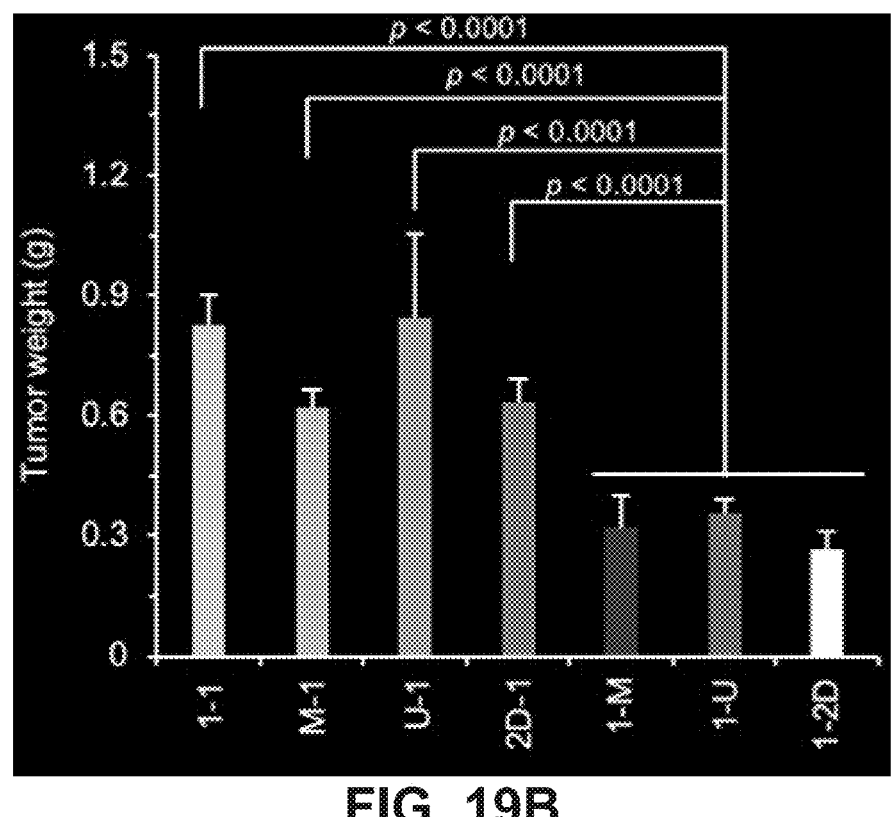
Figure 19C:
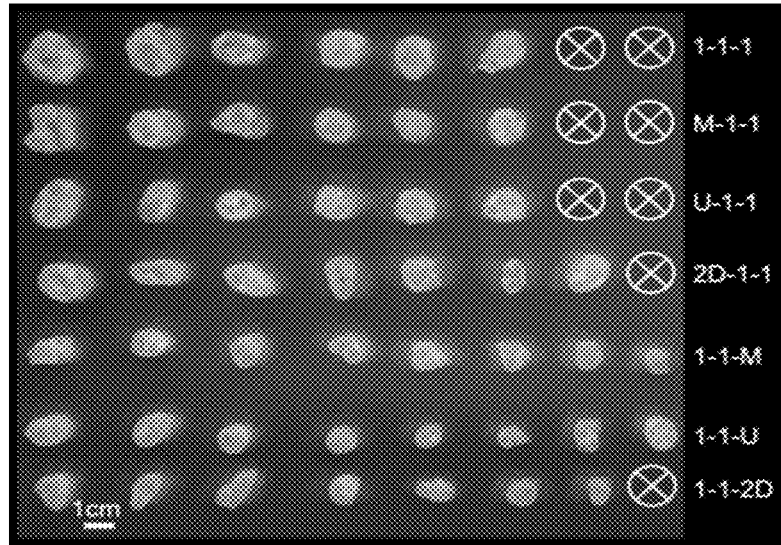
Figure 19D:
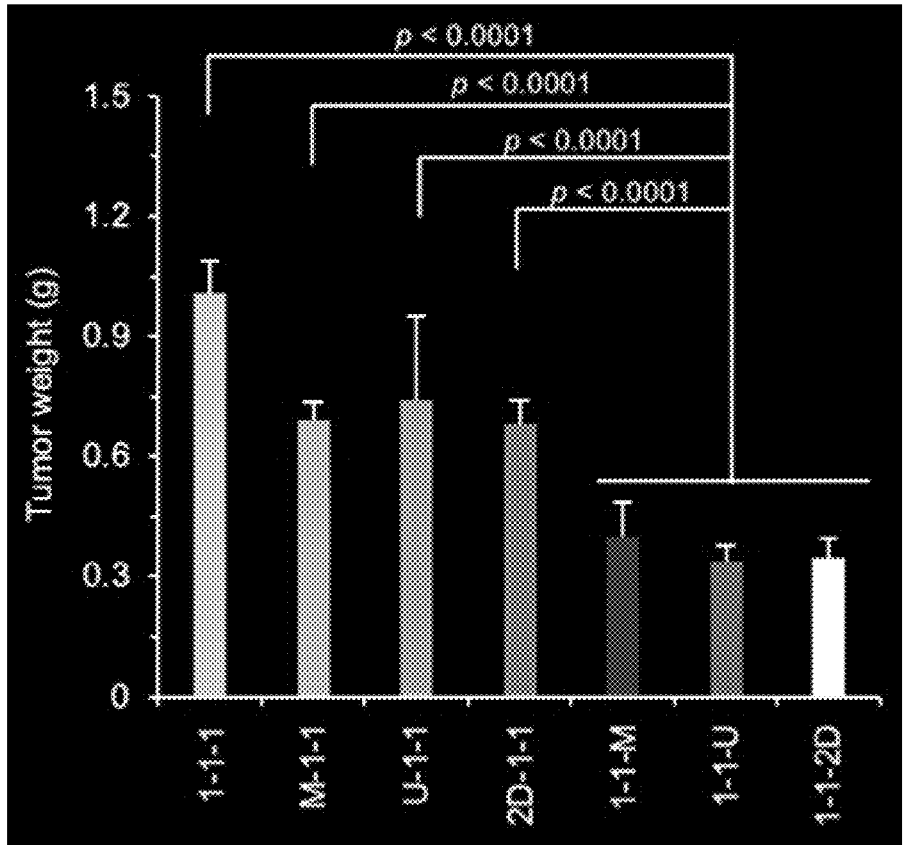

As shown in FIG. 4L-4M, the growth of the second-generation 1-2D, 1-U, and 1-M tumors is much slower than the G2 2D-1, U-1, M-1, and 1-1 tumors and the difference in tumor weight is significant (FIG. 19A-19B). Similarly, the third-generation 1-1-2D, 1-1-U, and 1-1-M tumors grow much slower than the G3 2D-1-1, U-1-1, M-1-1, and 1-1-1 tumors, and the difference in tumor weight is significant (FIG. 4N-4O and FIG. 19C-19D).

Figure 21:
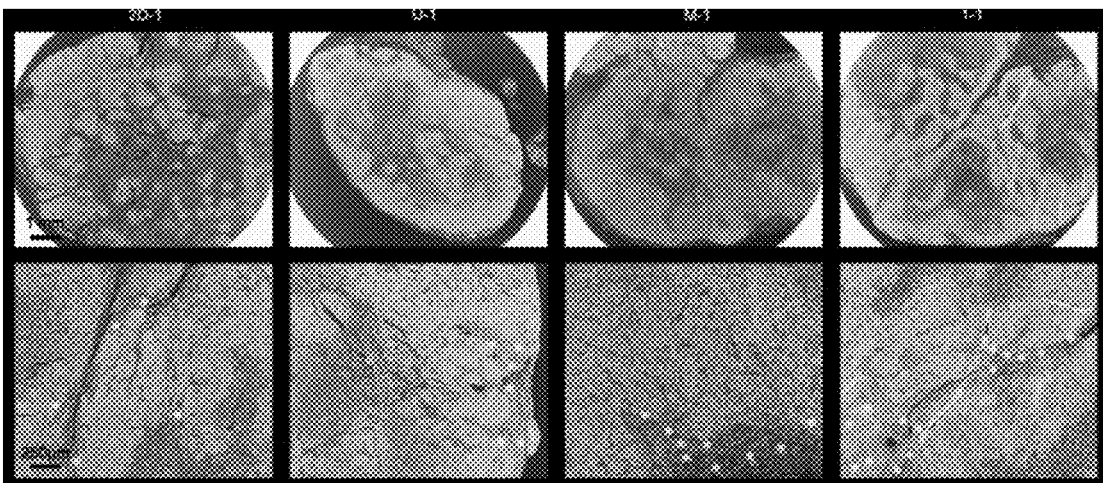
FIG. 21 depicts significantly increased formation of blood vessels and decreased area of necrosis in G2 tumors grown from cells obtained using the 1csc culture method. Representative images of H&E stained G2 tumor tissues collected after sacrificing the mice on day 55 for the 2D-1, U-1, M-1, 1-1, 1-2D, 1-U, and 1-M groups. Quantitative analyses show that the G2 tumors grown from cells obtained with the 1csc culture (the 2D-1, U-1, M-1, and 1-1 groups) have less necrotic area than G2 tumors grown from cells obtained with 2Dcells (1-2D group), Ucells (1-U group), and Mcells (1-M group) cultures. Blue asterisks indicate blood vessels in tumor tissues, showing more blood vessels in the 2D-1, U-1, M-1, and 1-1 tumors than the 1-2D, 1-U, and 1-M tumors. Error bars denote mean #s.d., n=3, and statistical analyses were performed by one-way ANOVA with post hoc Tukey test. The 2D-1, U-1, M-1, or 1-1 group is compared with the 1-2D, 1-U, and 1-M groups altogether.
Figure 21:
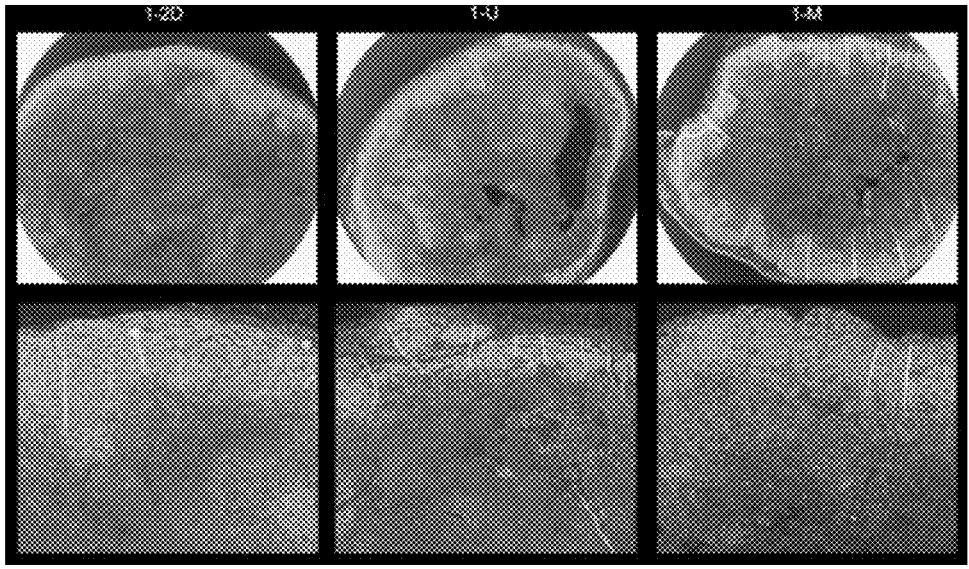
Figure 21:
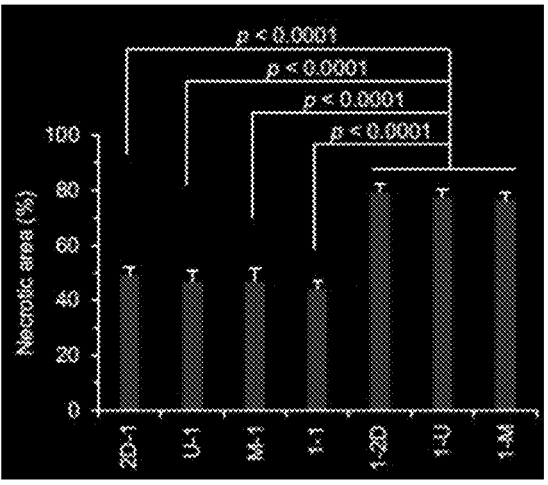
Figure 22:
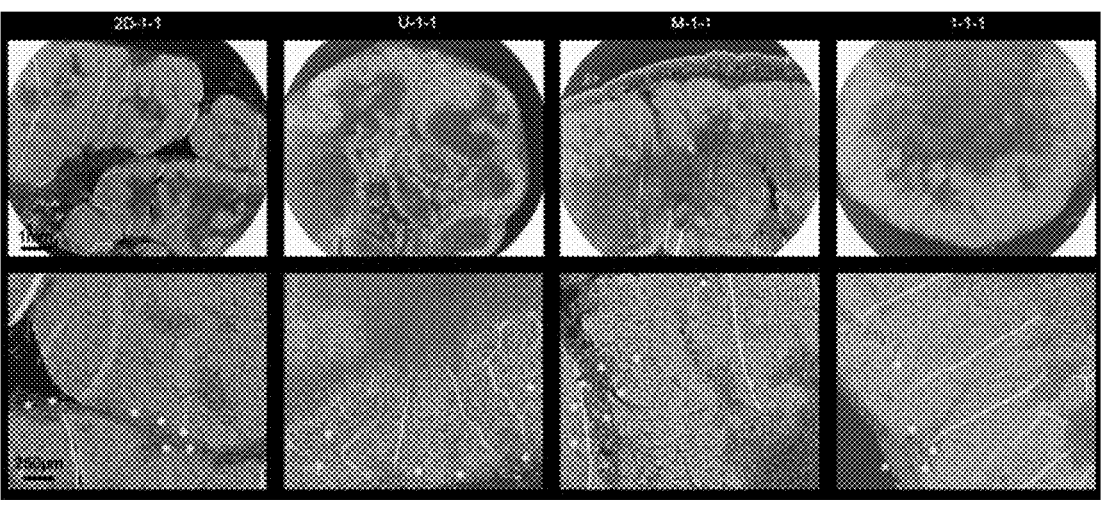
FIG. 22 depicts significantly increased formation of blood vessels and decreased area of necrosis in G3 tumors grown from cells obtained using the 1csc culture method. Representative images of H&E stained G3 tumor tissues collected after sacrificing the mice on day 55 for the 2D-1-1, U-1-1, M-1-1, 1-1-1, 1-1-2D, 1-1-U, and 1-1-M. Quantitative analyses show that the G3 tumors grown from cells obtained with the 1csc culture (the 2D-1-1, U-1-1, M-1-1, and 1-1-1groups) have significantly less necrotic area than G3 tumors grown from cells obtained with 2Dcells (1-1-2D group), Ucells (1-1-U group), and Mcells (1-1-M group) cultures. Blue asterisks indicate blood vessels in the tumor tissues, showing more blood vessels in the 2D-1-1, U-1-1, M-1-1, and 1-1-1tumors than the 1-1-2D, 1-1-U, and 1-1-M tumors. Error bars denote mean±s.d., n=3, and statistical analyses were performed by one-way ANOVA with post hoc Tukey test. The 2D-1-1, U-1-1, M-1-1 or 1-1-1 group is compared with the 1-1-2D, 1-1-U, and 1-1-M groups altogether.
Figure 22:
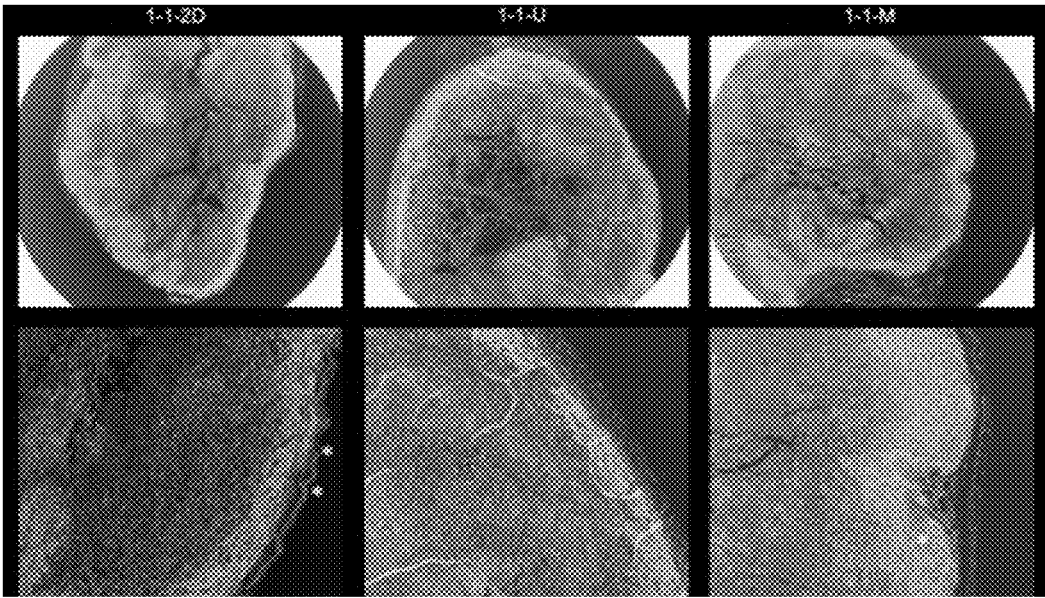
Figure 22:
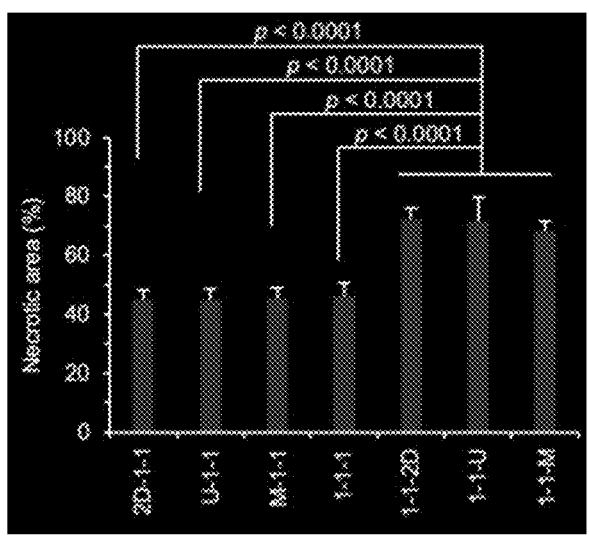
Figure 23:
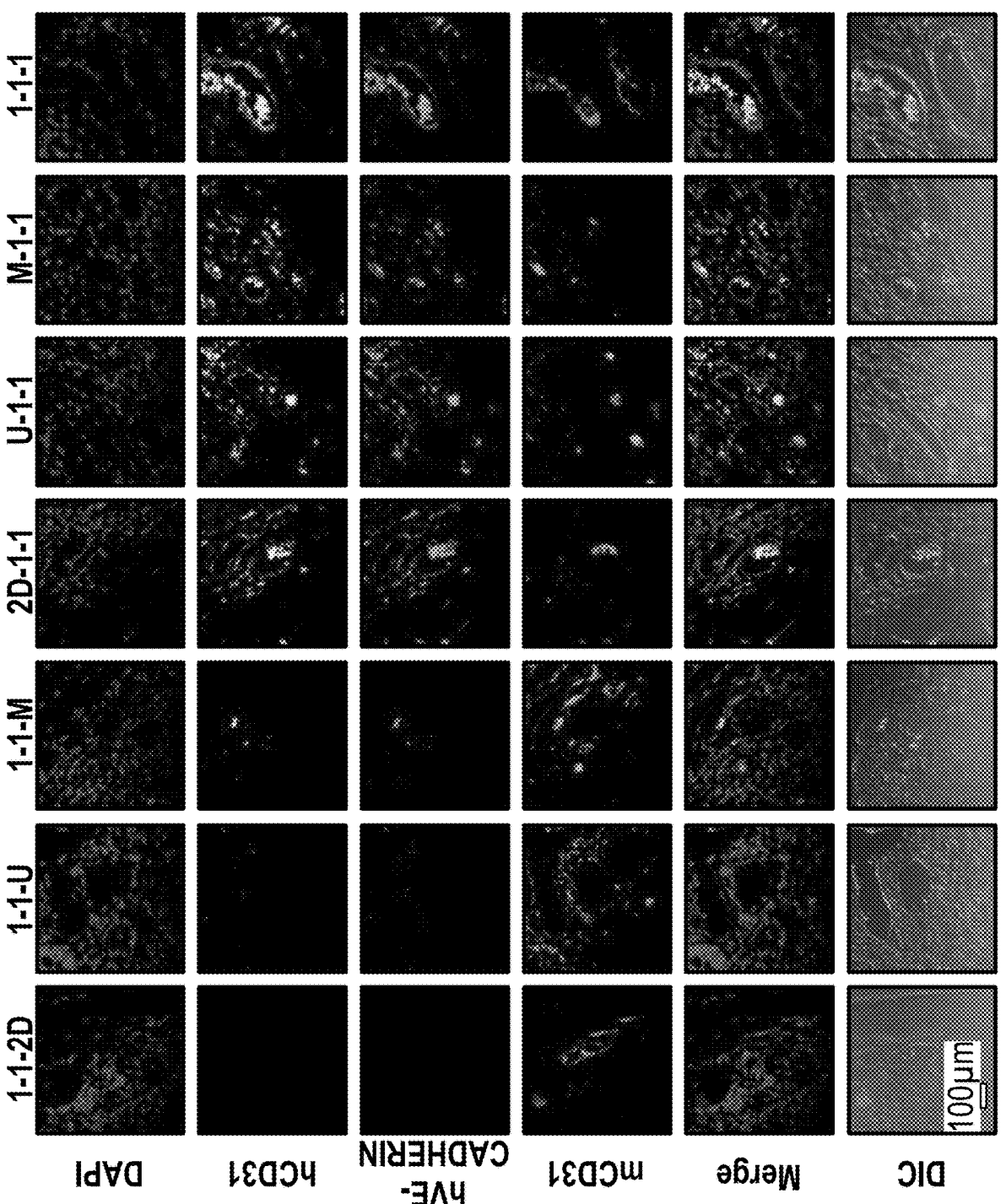
FIG. 23 depicts the 1csc colony cells differentiate into endothelial cells to form blood vessels in vivo. To identify the origin of the blood vessels in 1-1-2D, 1-1-U, 1-1-M, 2D-1-1, U-1-1, M-1-1, and 1-1-1 tumors, immunostainings with human CD31 (hCD31), human VE-CADHERIN (hVE-CADHERIN) and mouse CD31 (mCD31) were performed. The confocal micrographs show that blood vessels with hCD31 and hVE-cadherin are evident in the 2D-1-1, U-1-1, M-1-1, and 1-1-1tumors grown from the 1csc colony cells. In contrast, staining of hCD31 or hVE-CADHERIN is negligible in 1-1-2D, 1-1-U, and 1-1-M tumors grown from cells obtained using the 2Dcells, Ucells, and Mcells culture methods, respectively. The mCD31 staining is observable in all the tumors.
Figure 24:
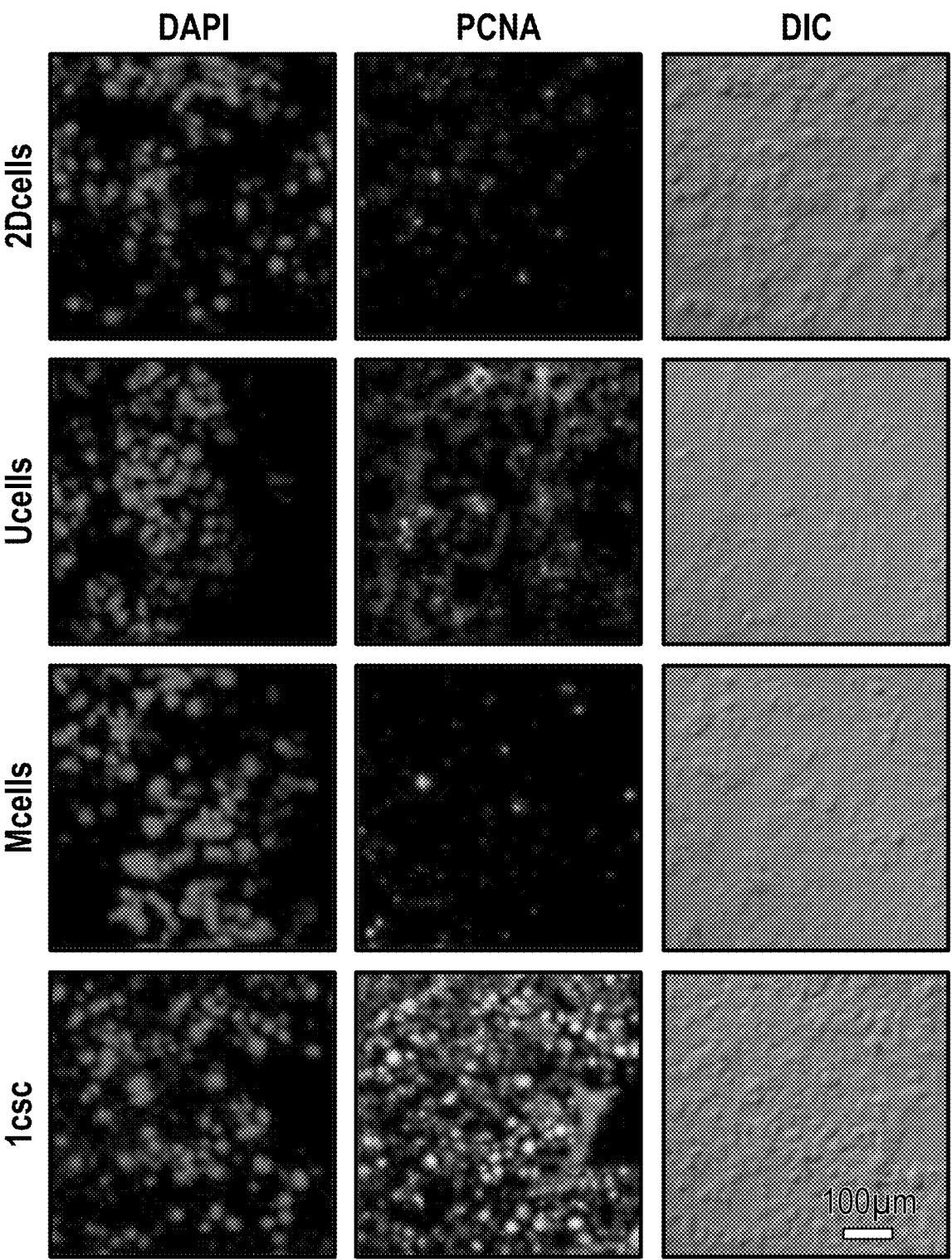
FIG. 24 depicts multiple mechanisms may contribute to the fast growth of tumors from the 1csc colony cells. Confocal images showing that tumors (2D-1, U-1, M-1, 1-1, 2D-1-1, U-1-1, M-1-1, and 1-1-1) grown from the 1csc colony cells express more proliferating cell nuclear antigen (PCNA that promotes cell proliferation) than tumors (2Dcells, Ucells, Mcells, 1-2D, 1-U, 1-M, 1-1-2D, 1-1-U, and 1-1-M) grown from cells obtained with the other three culture methods (i.e., 2Dcells, Ucells, and Mcells).
Figure 24:
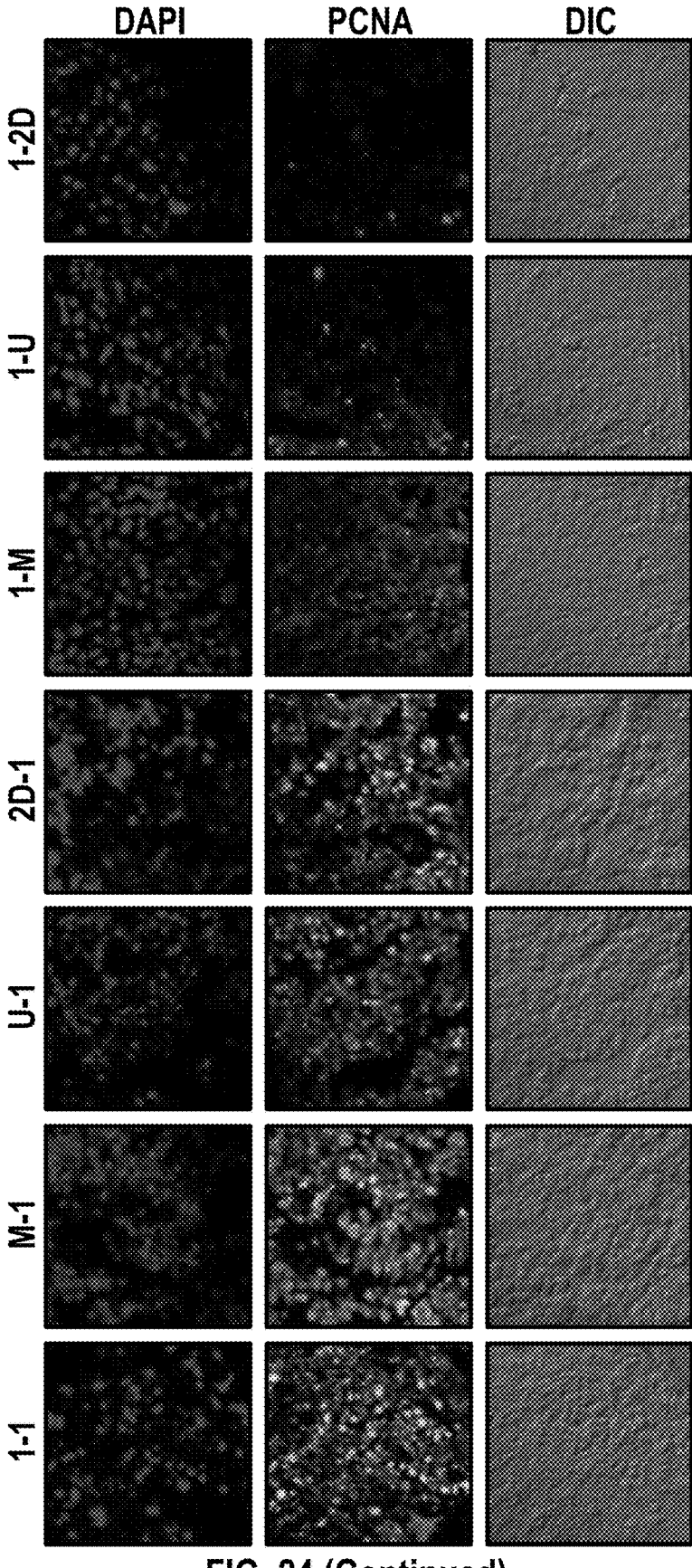
Figure 24:
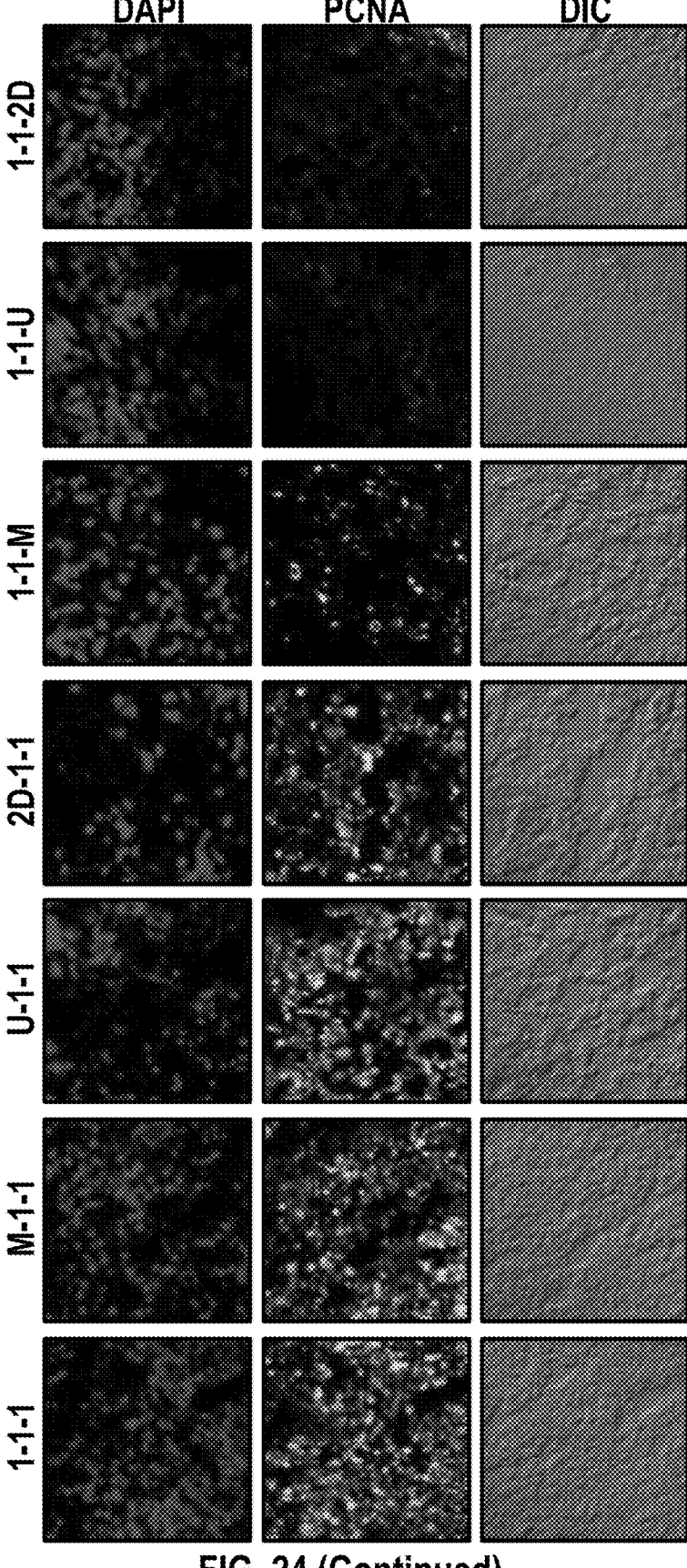

To find out why the 1csc colony cells are highly tumorigenic, histology of the tumor tissues was analyzed through hematoxylin and eosin (H&E) staining. Interestingly, the percentage of necrotic area in the tumors grown from cells obtained with the 2Dcells, Ucells, and Mcells cultures is significantly larger than that in tumors grown from the 1csc colony cells for all three generations (G1-G3) (FIG. 20-22). This is possibly because the 1csc colony cells can better regenerate the tumor microenvironment than cells obtained with the other three culture methods. For example, more blood vessels can be observed in the tumors grown from the 1csc colony cells than cells obtained with the other three culture methods (FIG. 20-22), which may be attributed to the endothelial differentiation capability of the 1csc colony cells (FIG. 3A-3B). This is confirmed by immunofluorescence staining of human endothelial cell markers hCD31 and hVE-cadherin: much higher expression of hCD31 and hVE-cadherin can be observed in the 2D-1-1, U-1-1, M-1-1 and 1-1-1 tumors than 1-1-2D, 1-1-U, and 1-1-M tumors, although the expression of mouse endothelial cells marker (mCD31) is evident in all the tumors (FIG. 23). Increased blood vessels facilitate the transport of nutrients and oxygen inside tumors, which may contribute to the reduced necrosis observed in the tumors grown from the 1csc colony cells. It is worth noting that other mechanisms may contribute to the fast proliferation of tumors grown from the 1csc colony cells, such as the high expression of proliferating cell nuclear antigen (PCNA, FIG. 24) that promotes cell proliferation.

v. In Vivo Metastasis

Figure 5A:
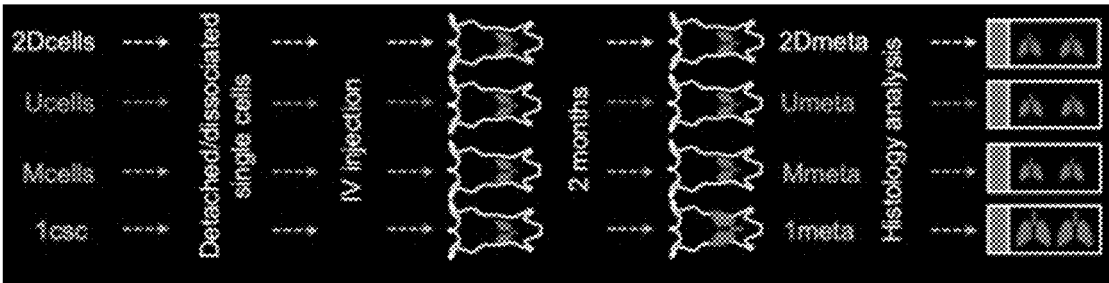
FIG. 5A-5F depict the characterization of stemness with metastasis assay in vivo.
Figure 5B:
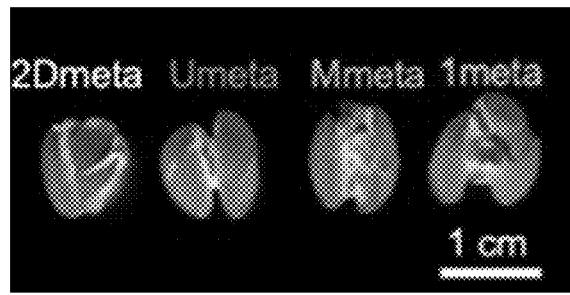
Figure 5C:
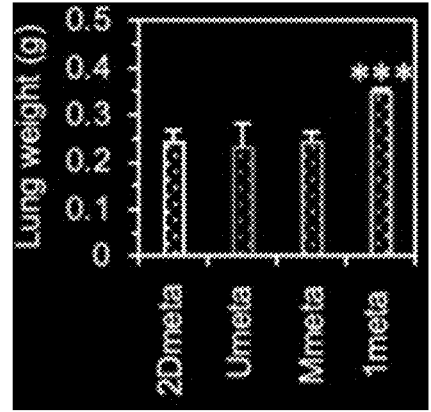
Figure 5D:
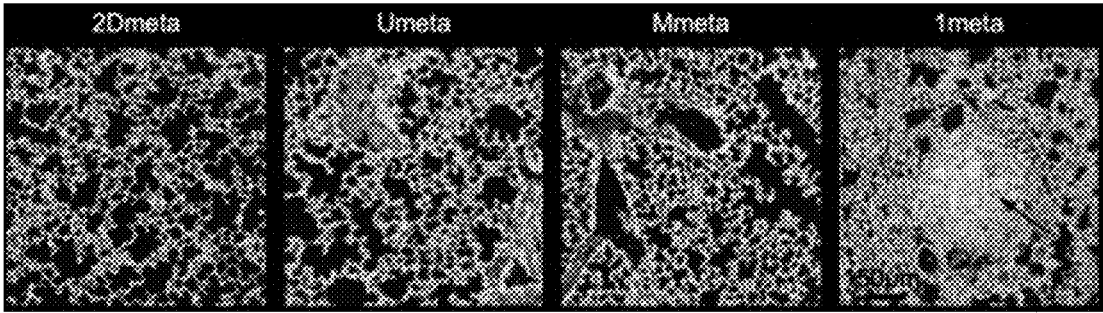
Figure 5E:
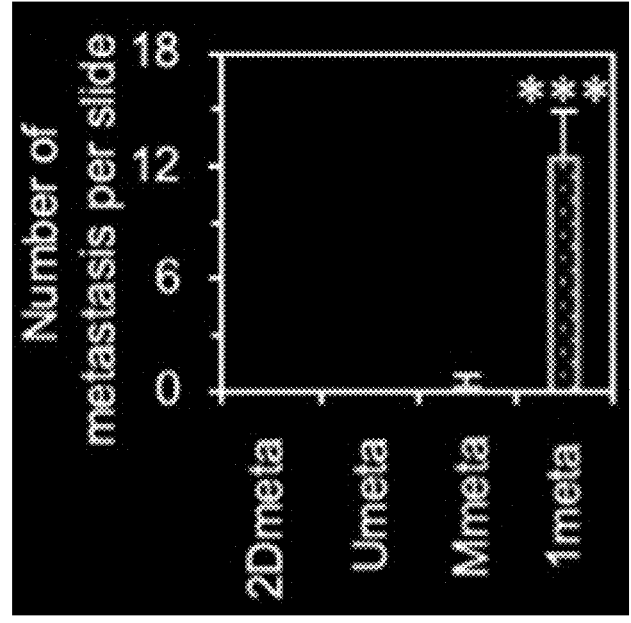
Figure 5F:
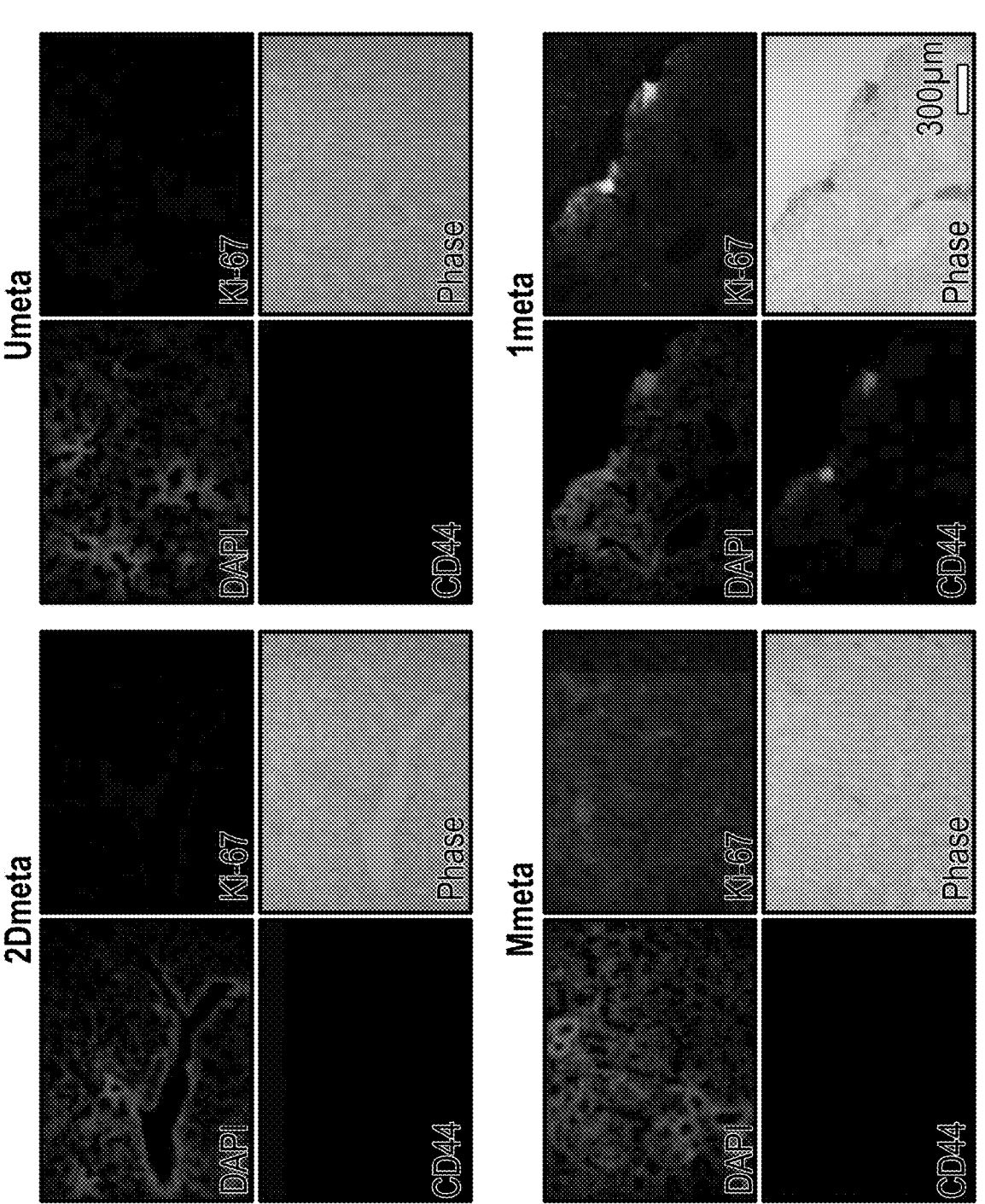
Figure 25:
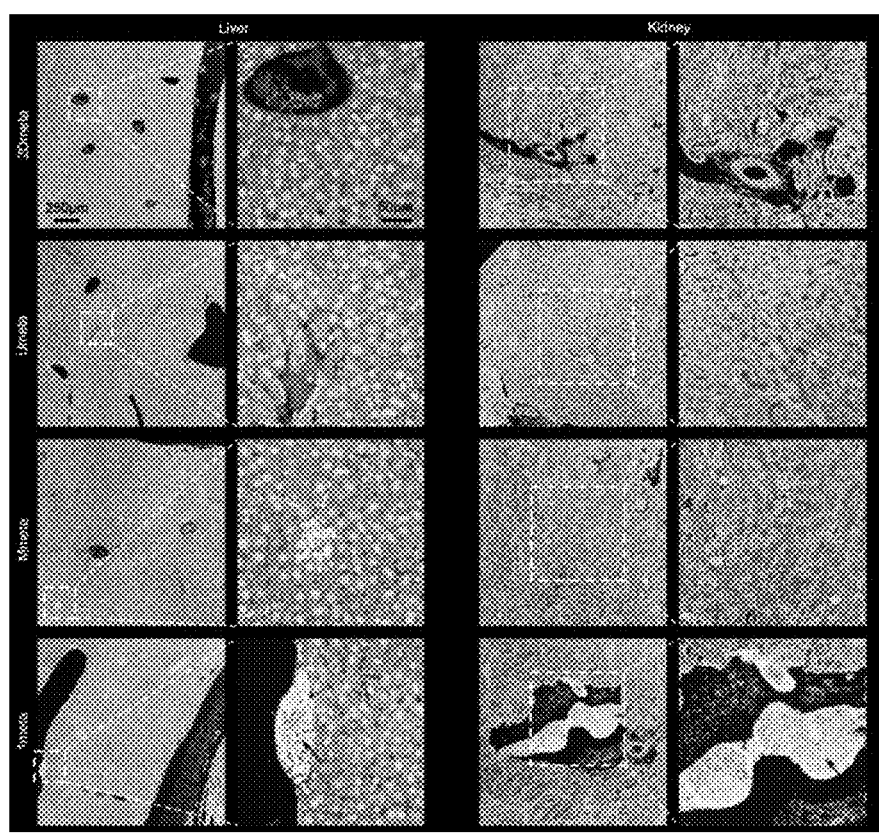
FIG. 25 depicts histology (H&E staining) micrographs show that the 1csc colony cells may metastasize in livers and kidneys to form metastasis (1meta) in the two critical organs (arrows in the zoom-in images at the bottom row) after intravenous injection.
Figure 26:
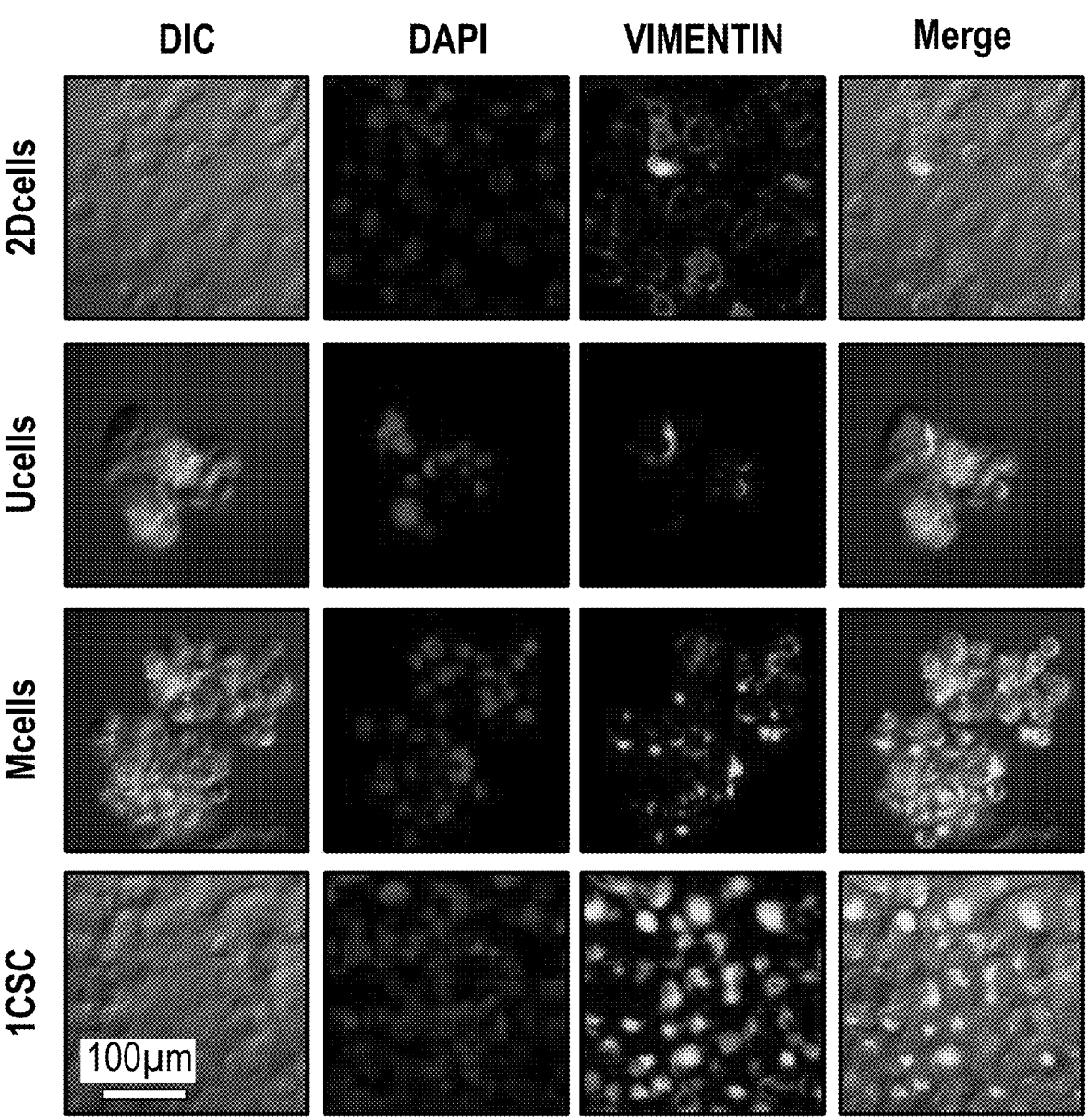
FIG. 26 depicts confocal images showing the expression of epithelial-mesenchymal transition (EMT) markers. The expression of VIMENTIN and β-CATENIN is upregulated and the expression of E-CADHERIN is downregulated in the 1csc colony cells, compared with cells of the other three groups. Increased VIMENTIN and β-CATENIN expression positively correlates with augmented invasiveness and metastasis. Suppression of E-CADHERIN may lead to mesenchymal phenotype, increased cell migration and invasion, as well as metastasis. The data suggest that the 1csc colony cells have higher ability to form metastatic tumors than cells from the 2Dcells, Ucells, and Mcells culture methods.
Figure 26:
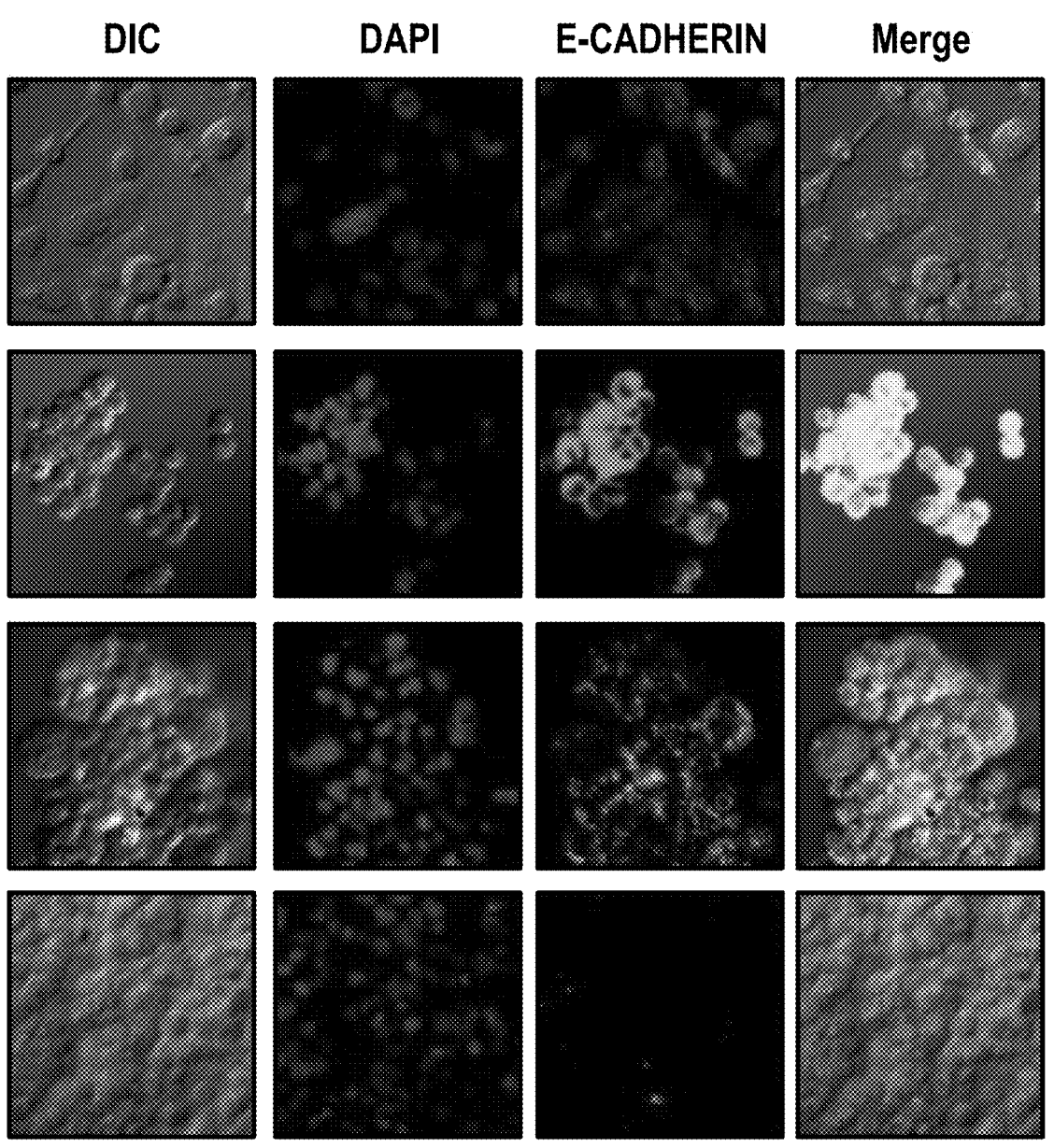
Figure 26:
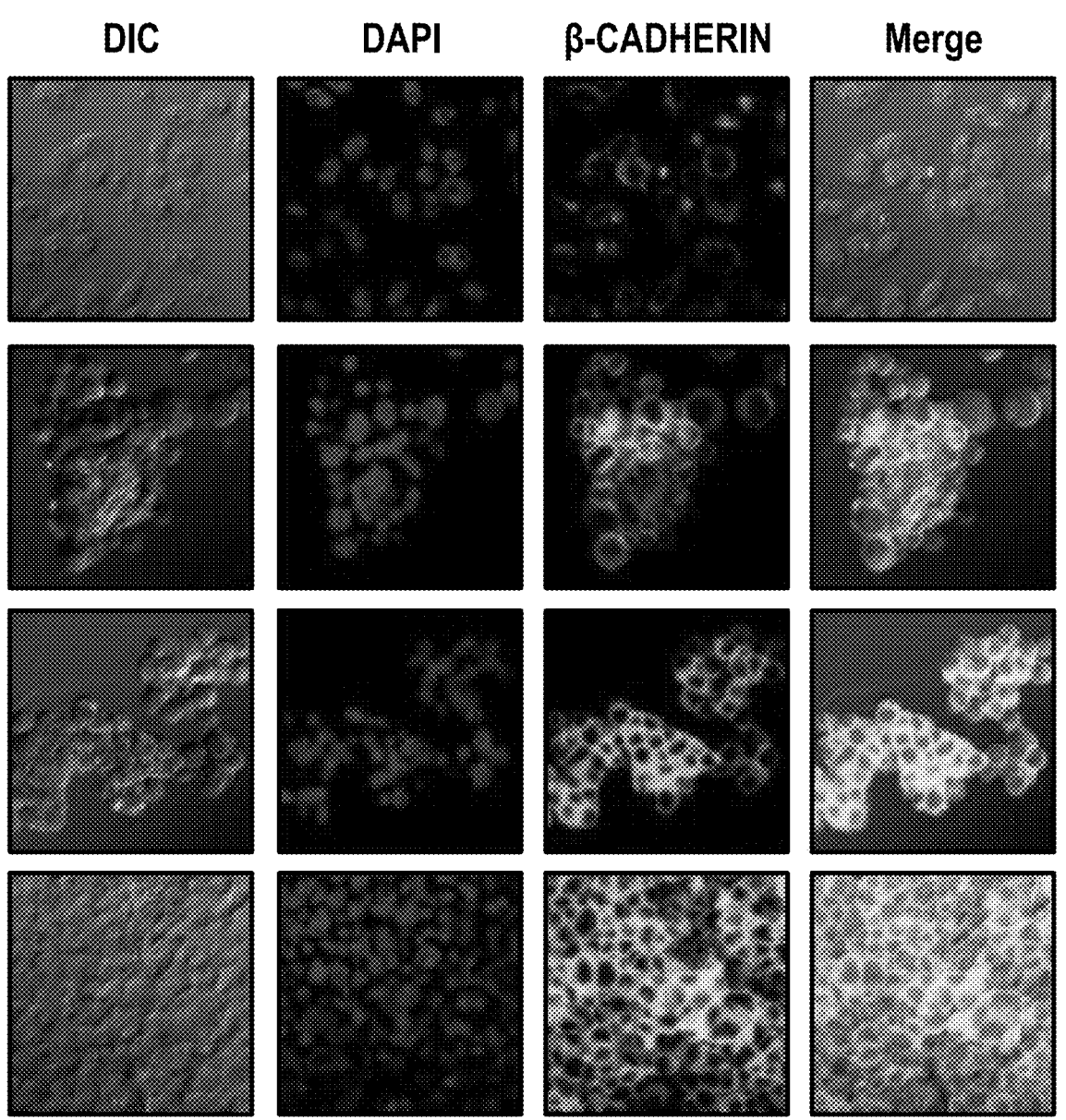

Besides high tumorigenesis, CSCs have been posited to cause metastases. To investigate this, attached cells and cell aggregates/spheroids/colonies from the 2Dcells, Ucells, Mcells, or 1csc cultures were dissociated into single cells for injection into C57BL/6 mice with intact immune system via their tail veins ($2 \times 10^6$ cells per mouse, FIG. 5A). The mice were sacrificed after two months and the lungs from the four groups (2Dmeta, Umeta, Mmeta or 1meta) were collected for further analyses. First, all the lungs in the 1meta group appear larger than that in the other three groups (FIG. 5B), and all the lungs in the 1meta group are significantly heavier than that in all the other three groups (FIG. 5C). This is possibly due to the formation of cancer metastases in this group. Indeed, further histology analyses with H&E staining show that metastases of a few hundred microns in size with densely packed cells formed in all the lungs of the 1meta group (FIG. 5D-5E). The metastatic tumors in the lungs of the 1meta group are further confirmed by immunofluorescence staining with human CD44 and Ki67 (FIG. 5F). In stark contrast, no metastasis was observed in any of the lungs of the 2Dmet and Umeta groups and only one metastasis was observed in one of the lungs of the Mmeta group. This is probably because the cancer cells injected into mice for these groups are not stem cells and can be easily killed by the immune system of the mice. For the 1csc group, the colony cells are likely stem cells and may evade the immune system of the mice. The capability of human stem cells in evading the immune system to survive in murine species (mice and rats) has also been reported in the literature.[23] It is worth noting that metastatic tumors were also observed in the liver and kidney of mice (2/8) in the 1meta group (FIG. 25). The seeding and growth of breast metastatic tumors at sites distant from the primary tumor is a complex and multistep process, and the epithelial-mesenchymal transition (EMT) has been considered a major mechanism for breast cancer metastasis. Increased vimentin expression is frequently used as an EMT marker in cancer and there is a positive correlation of vimentin expression with augmented invasiveness and metastasis. Indeed, as shown in FIG. 26, higher expression of VIMENTIN is observed in the 1csc colony cells than cells from the other three groups. Moreover, decreased expression of E-CADHERIN and increased expression of β-CATENIN are observed in the 1csc colony cells compared with cells in the other three groups (FIG. 26). Previous studies suggest that the suppression of E-cadherin and increased expression of β-catenin lead to mesenchymal phenotype, increased cell migration and invasion, and enhanced metastasis.[26] Similarly, these data suggest that the 1csc colony cells possess stronger capacity of invasion and migration than cells in the other three groups.

vi. Drug Resistance and Clinical Significance

Figure 6A:
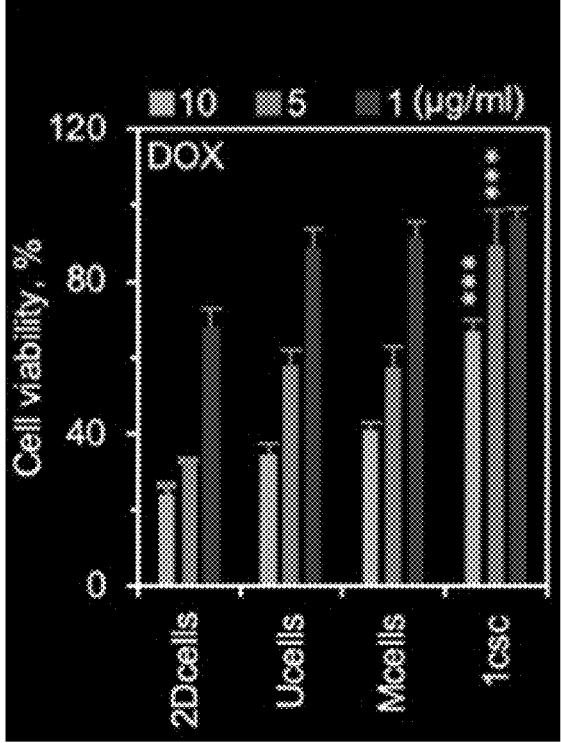
FIG. 6A-6D depict the implications for developing CSC-targeted therapeutic strategies.
Figure 6B:
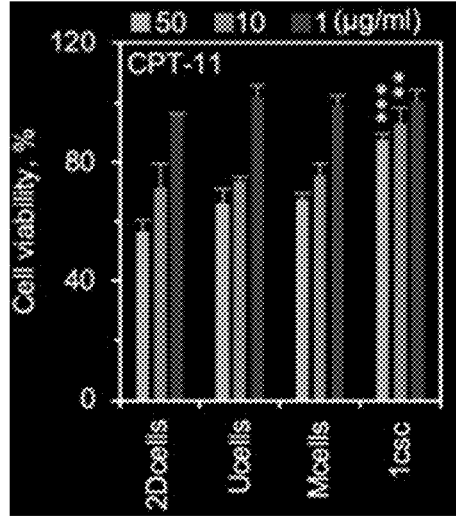
Figure 6C:
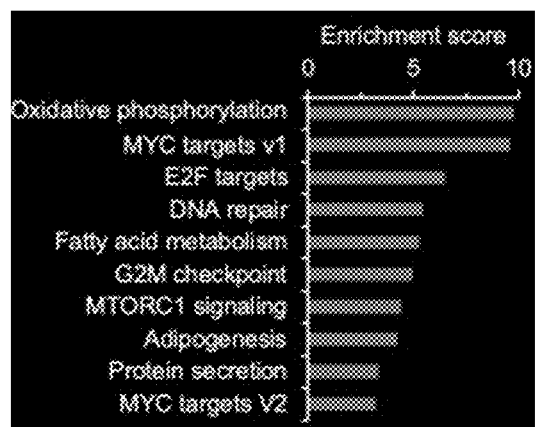
Figure 27A:
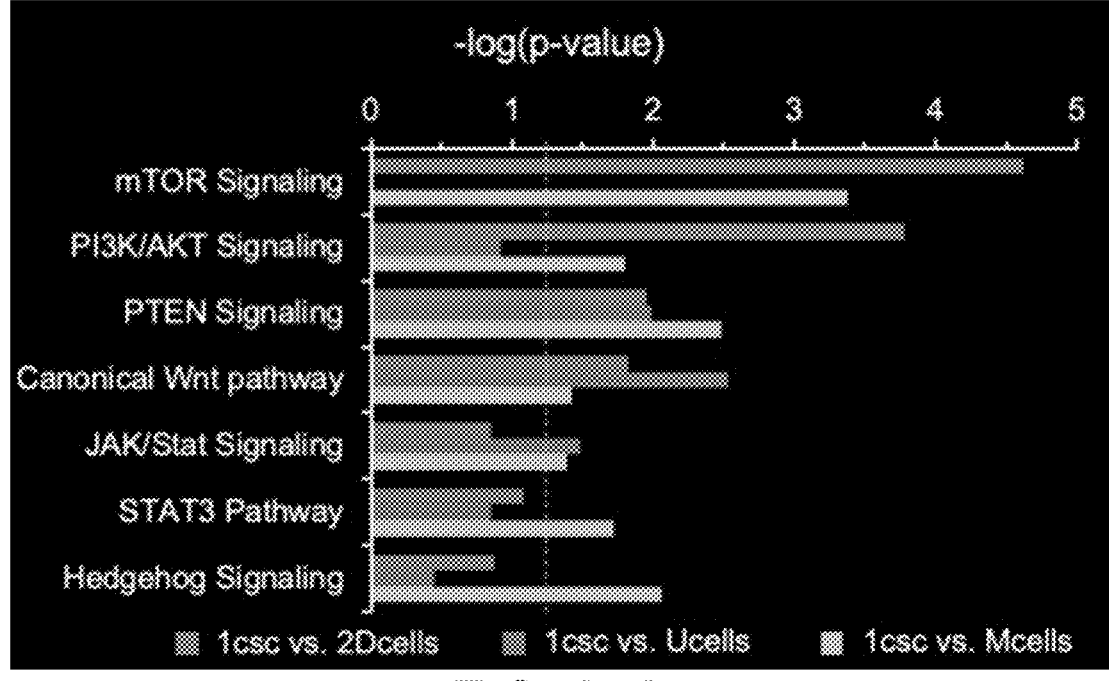
Figure 27B:
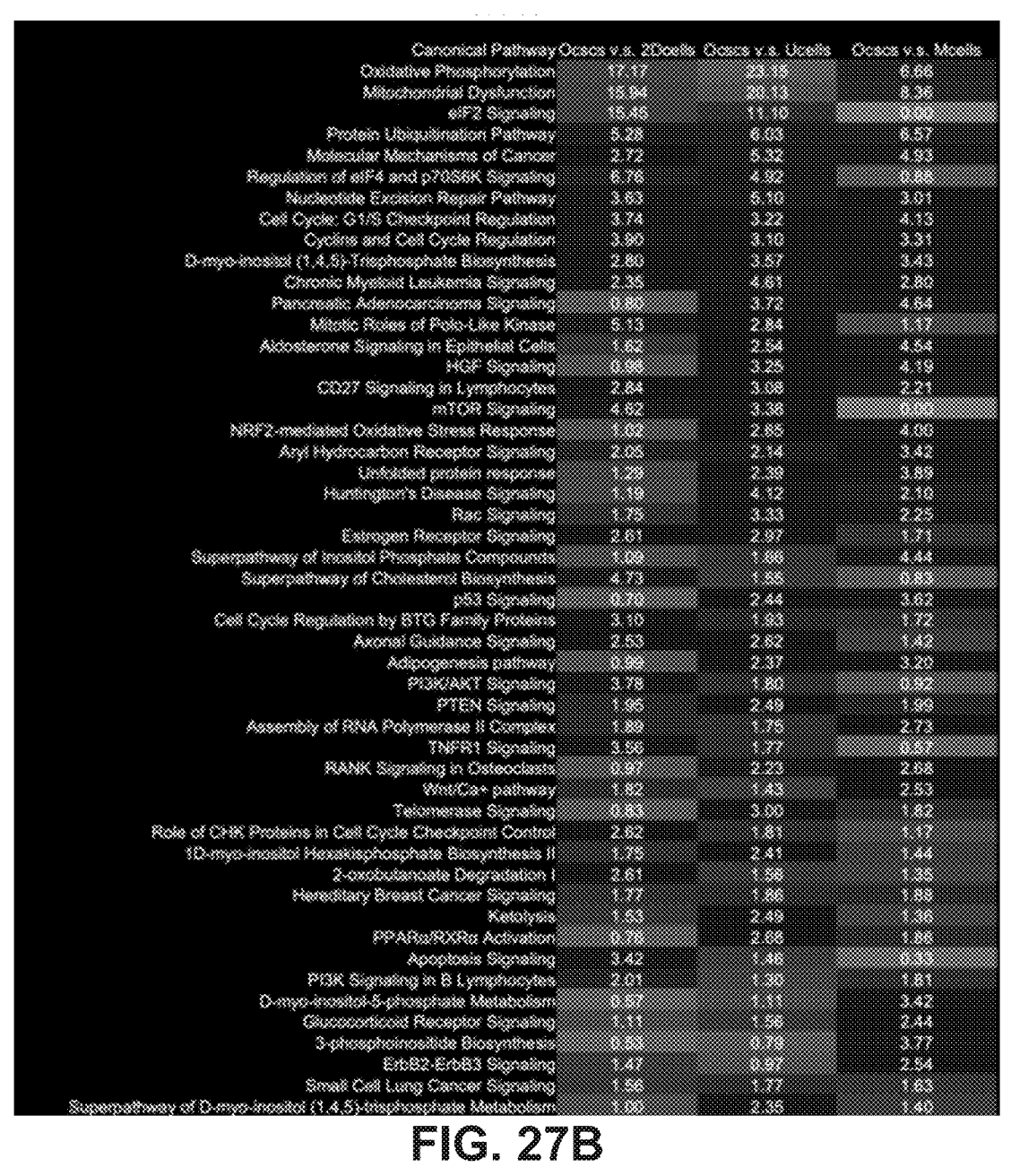

Having demonstrated the stemness of the 1csc colony cells through the serial passaging assay in vitro, gene and protein expression analyses of in vitro and in vivo cells, and studies on multilineage differentiation, three generations of in vivo tumorigenesis, and metastatic capacity, we next treated these cells with two chemotherapeutic drugs, doxorubicin hydrochloride (DOX) and camptothecin-11 (CPT-11). It is found that the 1csc colony cells are significantly more resistant to both drugs than cells obtained with the other three culture methods (FIG. 6A-6B). This is not surprising, as the upregulation of many CSC-related genes (e.g., DNA repair, anti-apoptosis, and drug resistance) and downregulation of proliferation-related genes (FIG. 2D) should render the 1csc colony cells highly resistant to chemotherapeutic drugs. In order to find potential therapeutic targets of CSCs to overcome their drug resistance, differentially regulated canonical pathways as well as genes were analyzed. The results are shown in FIG. 27. In conjunction to alterations in stemness related pathways (FIG. 27A), pathways related to energy metabolism (e.g., oxidative phosphorylation and mitochondrial dysfunction, FIG. 27B) are significantly altered in the 1csc group compared with the other three groups. Additionally, similar pathways (oxidative phosphorylation and mitochondrial dysfunction) are altered between the in vitro 1csc colony cells and in vivo tumors grown from them (FIG. 28), suggesting these pathways may play an important role in supporting/maintaining the stemness of the 1csc colony cells. Differences in energy metabolism are also revealed by utilizing gene set enrichment analysis (GSEA) of the top 23enriched pathways with hallmarks (Table 3), and the top 10 are given in FIG. 6C. These enriched pathways in 1csc colony cells are involved in stemness, decreased cell growth, anti-apoptosis, drug resistance, enhanced DNA repair, and reduced metabolism, which are considered important properties of CSCs (FIG. 6C and Table 3). Most of the signaling pathways are also different between the in vitro 1csc colony cells and the in vivo 1csc tumor cells, and the top 39 are given in Table 4.

55

TABLE 3

A list of the 23 gene sets enriched in the 1csc colony cells obtained by gene set enrichment analysis (GSEA).

| NAME | NES | FDR q-val |
| --- | --- | --- |
| Oxidative Phosphorylation | 9.666 | 0 |
| MYC Targets V1 | 9.508 | 0 |
| E2F Targets | 6.45 | 0 |
| DNA Repair | 5.423 | 0 |
| Fatty Acid Metabolism | 5.246 | 0 |
| G2M Checkpoint | 4.897 | 0 |
| MTORC1 Signaling | 4.367 | 0 |
| Adipogenesis | 4.22 | 0 |
| Protein Secretion | 3.311 | 0 |
| MYC Targets V2 | 3.199 | 0 |
| Peroxisome | 2.992 | 0 |
| Glycolysis | 2.837 | 0 |
| Xenobiotic Metabolism | 2.756 | 0 |
| Interferon Alpha Response | 2.745 | 0 |
| Interferon Gamma Response | 2.71 | 0 |
| Reactive Oxygen Species Pathway | 2.482 | 0 |
| Unfolded Protein Response | 2.192 | 0.003 |
| KRAS Signaling Up | 2.163 | 0.003 |
| Complement | 2.149 | 0.003 |
| UV Response Up | 2.039 | 0.005 |
| Bile Acid Metabolism | 1.896 | 0.012 |
| Apoptosis | 1.764 | 0.026 |
| PI3K AKT MTOR Signaling | 1.626 | 0.049 |

TABLE 4

A list of the most enriched 39 gene sets in the 1csc colony cells when compared to the G1 in vivo tumors of the 1csc group.

| NAME | NES | FDR q-val |
| --- | --- | --- |
| Oxidative Phosphorylation | 11.649 | 0 |
| Myc Targets v1 | 10.920 | 0 |
| E2f Targets | 9.330 | 0 |
| Mtorcl Signaling | 9.285 | 0 |
| G2M Checkpoint | 7.896 | 0 |
| DNA Repair | 7.135 | 0 |
| Protein Secretion | 6.995 | 0 |
| Unfolded Protein Response | 6.723 | 0 |
| Adipogenesis | 6.598 | 0 |
| Glycolysis | 6.365 | 0 |
| TNFa Signaling via NFKb | 6.172 | 0 |
| Fatty Acid Metabolism | 6.167 | 0 |
| P53 Pathway | 6.068 | 0 |
| Mitotic Spindle | 5.163 | 0 |
| Heme Metabolism | 5.129 | 0 |
| Apoptosis | 5.113 | 0 |
| Hypoxia | 4.797 | 0 |
| Uv Response Up | 4.648 | 0 |
| Cholesterol Homeostasis | 4.477 | 0 |
| Androgen Response | 4.395 | 0 |
| Peroxisome | 4.360 | 0 |
| Xenobiotic Metabolism | 4.136 | 0 |
| PI3k Akt Mtor Signaling | 4.116 | 0 |
| Interferon Gamma Response | 4.066 | 0 |
| Myc Targets v2 | 3.930 | 0 |
| Complement | 3.925 | 0 |
| Interferon Alpha Response | 3.871 | 0 |
| Estrogen Response Late | 3.726 | 0 |
| Reactive Oxigen Species Pathway | 3.498 | 0 |
| IL2 Stat5 Signaling | 3.250 | 0 |
| Estrogen Response Early | 3.130 | 0 |
| Uv Response Dn | 2.850 | 0 |
| TGF Beta Signaling | 2.824 | 0 |
| Inflammatory Response | 2.672 | 0 |
| KRAS Signaling Up | 2.651 | 0 |
| Bile Acid Metabolism | 2.544 | 1.35E−04 |
| IL6 JAK Stat3 Signaling | 2.405 | 4.26E−04 |
| Allograft Rejection | 1.878 | 0.011236 |
| Epithelial Mesenchymal Transition | 1.828 | 0.014931 |

Lastly, we examined the clinical significance of targeting the CSCs isolated with the 1csc culture by investigating the

Figure 6D:
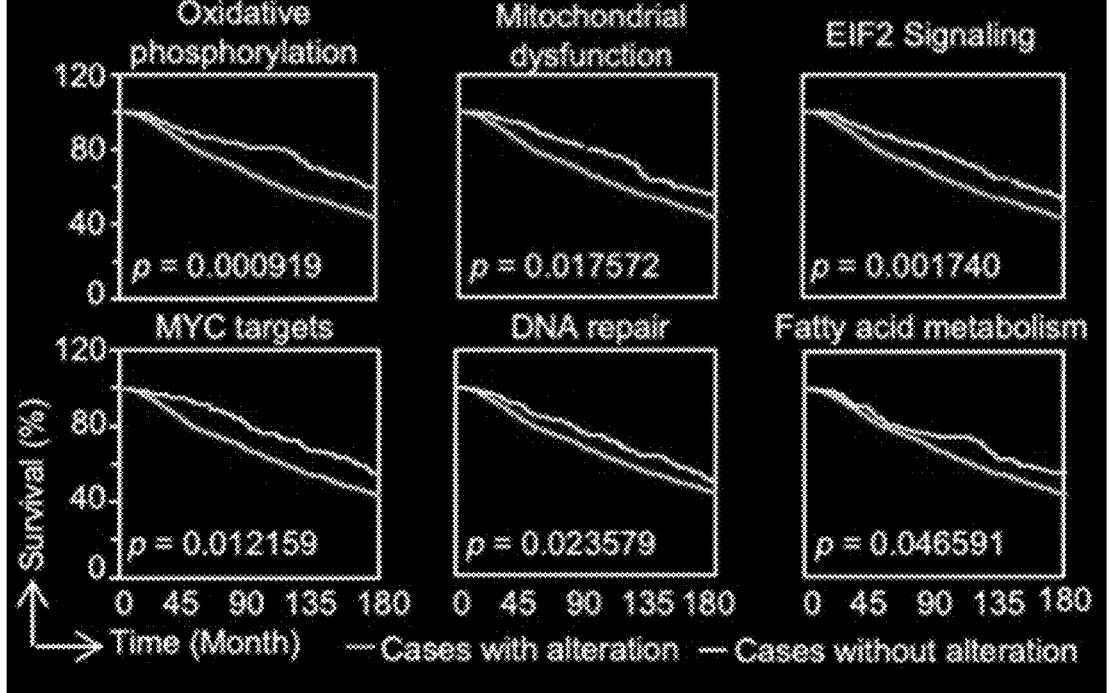

56 survival of breast cancer patients with alterations in the top enriched gene sets found from our GSEA analyses of the 1csc colony cells as compared to cells in the 2Dcells, Ucells, and Mcells groups. These include oxidative phosphorylation, mitochondrial dysfunction, EIF2 targets, MYC targets, DNA repair, and fatty acid metabolisms (FIG. 6C and S30-32). As shown by the Kaplan Meier estimates of survival (FIG. 6D), alterations of these gene sets decrease the prognostic outcomes in breast cancer patients, suggesting that they can be potential therapeutic targets for eliminating CSCs to improve breast patient survival. Perhaps, the combination of inhibitors of these pathways and/or their further combination with factors for guided differentiation (e.g., VEGF for endothelial differentiation so that the cells lose cancerous property and do not proliferate, FIG. 14) may be used to target CSCs and achieve improved outcomes of breast cancer therapy.

3. Conclusion

In conclusion, inspired by the prehatching embryos which start proliferation from one cell to form a colony, we developed a one-single-cell-microencapsulation (1csc) method to isolate and culture CSCs without any surface marker. Hyaluronic acid was found to be crucial for the CSCs to survive and form colonies under the 1csc culture and the CSCs take up ~3-5% the whole cancer cell population. Genome profiling indicates the stemness, DNA repair, anti-apoptosis, and drug resistance of the 1csc colony cells are enhanced while their tendency of proliferation is decreased compared with 2D cultured cells and cells obtained with the conventional approaches for isolating CSCs. Furthermore, the CSCs obtained with the 1csc culture are capable of multilineage (e.g., endothelial, cardiac, osteogenic, and neural) differentiation. Moreover, three generations of in vivo tumorigenesis studies together with investigations on metastasis indicate the CSCs are highly tumorigenic and metastatic. The CSCs are also shown to be highly resistant to chemotherapeutic drugs DOX and CPT-11. Our one-single-cell-microencapsulation approach for CSC isolation and culture may be valuable for understanding cancer biology and etiology and for facilitating the development of CSC-targeted therapies to fight against cancer.

REFERENCES

1. T. Rcya, S. J. Morrison, M. F. Clarke, I. L. Weissman, *Nature* 2001, 414, 105; C. T. Jordan, M. L. Guzman, M. Noble, *N. Engl. J. Med.* 2006, 355, 1253; J. E. Visvader, G. J. Lindeman, Nat. Rev. *Cancer* 2008, 8, 755.
2. C. E. Eyler, J. N. Rich, *J. Clin. Oncol.* 2008, 26, 2839; M. Cojoc, K. Mabert, M. H. Muders, A. Dubrovska, *Semin. Cancer Biol.* 2015, 31, 16; J. Zhou, Y. Zhang, *Expert Opin. Drug Discov.* 2009, 4, 741; A. E. Karnoub, A. B. Dash, A. P. Vo, A. Sullivan, M. W. Brooks, G. W. Bell, A. L. Richardson, K. Polyak, R. Tubo, R. A. Weinberg, *Nature* 2007, 449, 557; B. B. Zhou, H. Zhang, M. Damelin, K. G. Geles, J. C. Grindley, P. B. Dirks, *Nat. Rev. Drug Discov.* 2009, 8, 806.
3. Y. Yan, X. Zuo, D. Wei, *Stem Cells Transl. Med.* 2015, 4, 1033; J.-W. Jang, Y. Song, S.-H. Kim, J. Kim, H. R. Seo, *Life Sci.* 2017, 184, 25; M. Munz, P. A. Baeuerle, O. Gires, *Cancer Res.* 2009, 69, 5627; C. Ginestier, M. H. Hur, E. Charafe-Jauffret, F. Monville, J. Dutcher, M. Brown, J. Jacquemier, P. Viens, C. G. Kleer, S. Liu, *Cell Stem Cell* 2007, 1, 555; M. Grimm, M. Krimmel, J. Polligkeit, D. Alexander, A. Munz, S. Kluba, C. Keutel, J. Hoffmann, S. Reinert, S. Hoefert, *Eur. J. Cancer*

2012, 48, 3186; J. Li, S. Condello, J. Thomes-Pepin, X. Ma, Y. Xia, T. D. Hurley, D. Matei, J. X. Cheng, *Cell Stem Cell* 2017, 20, 303.

4. L. Vermeulen, M. Todaro, F. de Sousa Mello, M. R. Sprick, K. Kemper, M. P. Alea, D. J. Richel, G. Stassi, J. P. Medema, *Proc. Natl. Acad. Sci. U.S.A.* 2008, 105, 13427.

5. M. Al-Hajj, M. S. Wicha, A. Benito-Hernandez, S. J. Morrison, M. F. Clarke, *Proc. Natl. Acad. Sci. U.S.A.* 2003, 100, 3983; W. Chen, S. G. Allen, W. Qian, Z. Peng, S. Han, X. Li, Y. Sun, C. Fournier, L. Bao, R. H. W. Lam, S. D. Merajver, J. Fu, *Small* 2019, 15, e1802891.

6. P. C. Hermann, S. L. Huber, T. Herrler, A. Aicher, J. W. Ellwart, M. Guba, C. J. Bruns, C. Heeschen, *Cell Stem Cell* 2007, 1, 313.

7. P. Dalerba, S. J. Dylla, I.-K. Park, R. Liu, X. Wang, R. W. Cho, T. Hoey, A. Gurney, E. H. Huang, D. M. Simeone, *Proc. Natl. Acad. Sci. U.S.A.* 2007, 104, 10158.

8. E. Pastrana, V. Silva-Vargas, F. Doetsch, *Cell Stem Cell* 2011, 8, 486.

9. D. A. Fluri, P. D. Tonge, H. Song, R. P. Baptista, N. Shakiba, S. Shukla, G. Clarke, A. Nagy, P. W. Zandstra, *Nat. Methods* 2012, 9, 509.

10. H. Page, P. Flood, E. G. Reynaud, *Cell Tissue Res.* 2013, 352, 123.

11. S. Li, Z. Ma, Z. Niu, H. Qian, D. Xuan, R. Hou, L. Ni, *Stem Cells Dev.* 2009, 18, 1273.

12. G. Dontu, W. M. Abdallah, J. M. Foley, K. W. Jackson, M. F. Clarke, M. J. Kawamura, M. S. Wicha, *Genes Dev.* 2003, 17, 1253; H. Wang, P. Agarwal, S. Zhao, R. X. Xu, J. Yu, X. Lu, X. He, *Biomaterials* 2015, 72, 74.

13. S. Zhao, Z. Xu, H. Wang, B. E. Reese, L. V. Gushchina, M. Jiang, P. Agarwal, J. Xu, M. Zhang, R. Shen, Z. Liu, N. Weisleder, X. He, *Nat. Commun.* 2016, 7, 13306.

14. X. Yang, S. K. Sarvestani, S. Moeinzadeh, X. He, E. Jabbari, *Tissue Eng. Part A* 2012, 19, 669; J. Liu, Y. Tan, H. Zhang, Y. Zhang, P. Xu, J. Chen, Y. C. Poh, K. Tang, N. Wang, B. Huang, *Nat. Mater.* 2012, 11, 734; G. Rijal, W. Li, *Biomaterials* 2016, 81, 135.

15. O. Chaudhuri, S. T. Koshy, C. Branco da Cunha, J. W. Shin, C. S. Verbeke, K. H. Allison, D. J. Mooney, *Nat. Mater.* 2014, 13, 970.

16. T. Hiraga, S. Ito, H. Nakamura, *Cancer Res.* 2013, 73, 4112; M. Götte, G. W. Yip, *Cancer Res.* 2006, 66, 10233.

17. C. Vogel, E. M. Marcotte, *Nat. Rev. Genet.* 2012, 13, 227.

18. S. Bao, Q. Wu, R. E. Mclendon, Y. Hao, Q. Shi, A. B. Hjelmeland, M. W. Dewhirst, D. D. Bigner, J. N. Rich, *Nature* 2006, 444, 756.

19. L. Li, R. Bhatia, *Clin. Cancer Res.* 2011, 17, 4936.

20. B. E. Reubinoff, M. F. Pera, C.-Y. Fong, A. Trounson, A. Bongso, *Nat. Biotechnol.* 2000, 18, 399.

21. G. Bergers, D. Hanahan, Nature reviews. Cancer 2008, 8, 592; L. M. Ellis, D. J. Hicklin, *Nat. Rev. Cancer* 2008, 8, 579.

22. C. A. Gregory, W. G. Gunn, A. Peister, D. J. Prockop, *Anal. Biochem.* 2004, 329, 77.

23. P. Niemeyer, J. Vohrer, H. Schmal, P. Kasten, J. Fellenberg, N. P. Suedkamp, A. T. Mehlhorn, *Cytotherapy* 2008, 10, 784; J. Tang, X. Cui, T. G. Caranasos, M. T. Hensley, A. C. Vandergriff, Y. Hartanto, D. Shen, H. Zhang, J. Zhang, K. Cheng, *ACS Nano* 2017, 11, 9738; H. Wang, P. Agarwal, Y. Xiao, H. Peng, S. Zhao, X. Liu, S. Zhou, J. Li, Z. Liu, X. He, *ACS Cent. Sci.* 2017, 3, 875; P. Niemeyer, K. Szalay, R. Luginbuhl, N. P. Sudkamp, P. Kasten, *Acta Biomater.* 2010, 6, 900; J. A. Ankrum, J. F. Ong, J. M. Karp, *Nat. Biotechnol.* 2014, 32, 252; T. Celia-Terrassa, D. D. Liu, A. Choudhury, X. Hang, Y. Wei, J. Zamalloa, R. Alfaro-Aco, R. Chakrabarti, Y. Z. Jiang, B. I. Koh, H. A. Smith, C. DeCoste, J. J. Li, Z. M. Shao, Y. Kang, *Nat. Cell Biol.* 2017, 19, 711.

24. M. A. Huber, N. Azoitei, B. Baumann, S. Grünert, A. Sommer, H. Pehamberger, N. Kraut, H. Beug, T. Wirth, *J. Clin. Invest.* 2004, 114, 569; M. Yu, A. Bardia, B. S. Wittner, S. L. Stott, M. E. Smas, D. T. Ting, S. J. Isakoff, J. C. Ciciliano, M. N. Wells, A. M. Shah, *Science* 2013, 339, 580.

25. R. A. Whipple, E. M. Balzer, E. H. Cho, M. A. Matrone, J. R. Yoon, S. S. Martin, *Cancer Res.* 2008, 68, 5678; K. Vuoriluoto, H. Haugen, S. Kiviluoto, J. Mpindi, J. Nevo, C. Gjerdrum, C. Tiron, J. Lorens, J. Ivaska, *Oncogene* 2011, 30, 1436.

26. J. Cai, H. Guan, L. Fang, Y. Yang, X. Zhu, J. Yuan, J. Wu, M. Li, *J. Clin. Invest.* 2013, 123, 566; N. Desai, A. Alex, F. AbdelHafez, A. Calabro, J. Goldfarb, A. Fleischman, T. Falcone, *Reprod. Biol. Endocrinol.* 2010, 8, 119.

S1. P. Agarwal, J. K. Choi, H. Huang, S. Zhao, J. Dumbleton, J. Li, X. He, *Part. Part. Syst. Charact.* 2015, 32, 809; P. Agarwal, S. Zhao, P. Bielecki, W. Rao, J. K. Choi, Y. Zhao, J. Yu, W. Zhang, X. He, *Lab Chip* 2013, 13, 4525.

S2. W. Zhang, S. Zhao, W. Rao, J. Snyder, J. K. Choi, J. Wang, I. A. Khan, N. B. Saleh, P. J. Mohler, J. Yu, T. J. Hund, C. Tang, X. He, *J. Mater. Chem B* 2013, 1, 1002; S. Zhao, L. Zhang, J. Han, J. Chu, H. Wang, X. Chen, Y. Wang, N. Tun, L. Lu, X. F. Bai, M. Yearsley, S. Devine, X. He, J. Yu, *ACS Nano* 2016, 10, 6189.

S3. L. Vitiani, R. Pallini, M. Biffoni, M. Todaro, G. Invernici, T. Cenci, G. Maira, E. Parati, G. Stassi, L. Larocca, R. Maria. Tumour vascularization via endothelial differentiation of glioblastoma stem-like cells. *Nature* 2010, 468, 824.

S4. A. Morizane, D. Doi, T. Kikuchi, K. Nishimura, J. Takahashi, *J. Neurosci. Res.* 2011, 89, 117; S. M. Chambers, C. A. Fasano, E. P. Papapetrou, M. Tomishima, M. Sadelain, L. Studer, *Nat. Biotechnol.* 2009, 27, 275.

S5. B. Pereira, S. F. Chin, O. M. Rueda, H. K. Vollan, E. Provenzano, H. A. Bardwell, M. Pugh, L. Jones, R. Russell, S. J. Sammut, D. W. Tsui, B. Liu, S. J. Dawson, J. Abraham, H. Northen, J. F. Peden, A. Mukherjee, G. Turashvili, A. R. Green, S. Mckinney, A. Oloumi, S. Shah, N. Rosenfeld, L. Murphy, D. R. Bentley, I. O. Ellis, A. Purushotham, S. E. Pinder, A. L. Borresen-Dale, H. M. Earl, P. D. Pharoah, M. T. Ross, S. Aparicio, C. Caldas, *Nat. Commun.* 2016, 7, 11479.

The invention claimed is:

1. A composition comprising a one single cell encapsulated within a microparticle, wherein the microparticle comprises a core material enveloped by an outer shell, the core material comprising from about 0.1% to about 10% hyaluronic acid and a hydrogel, the outer shell comprising a spherical or substantially spherical polyanioic matrix, and the outer shell is from about 5 to about 500 nanometers in thickness.

2. The composition of claim 1, wherein the hydrogel comprises from about 0.1% alginate to about 5.5% alginate.

3. The composition of claim 1, wherein the outer shell comprises at least two layers of polyanionic matrix, each layer of polyanionic matrix comprising from about 1% to about 5% of polyanionic material.

4. The composition of claim 1, wherein the outer shell comprises at least two layers of polyanionic matrix, each layer of polyanionic matrix comprising from about 1% to about 5.5% of polyanionic material positioned around a first layer of polycationic material.

5. The composition of claim 1, wherein the outer shell comprises at least three layers of hydrogel, a first layer of hydrogel comprising a polyanionic material, a second layer comprising a polycationic material, and a third layer comprising a polyanionic material.

6. The composition of claim 5, wherein the first layer of hydrogel comprises from about 0.1% to about 5.5% alginate, the second layer of hydrogel comprises from about 0.5% to about 5.5% chondroitin or poly-lysine, and the third layer of hydrogel comprises from about 0.1% to 5.5% alginate.

7. The composition of claim 1, wherein the core material is spherical or substantially spherical in shape and comprises a diameter from about 5 microns to about 1 millimeter.

8. The composition of claim 1, wherein the core material comprises a diameter from about 5 nanometers to about 500 nanometers.

9. The composition of claim 1, wherein the core material comprises a diameter from about 10 nanometers to about 200 nanometers in diameter.

10. The composition of claim 1, wherein the outer shell comprises a thickness from about 5 nanometers to about 1 millimeter.

11. The composition of claim 10, wherein the outer shell comprises a thickness from about 10 nanometers to about 500 nanometers.

12. The composition of claim 11, wherein the outer shell comprises a thickness from about 10 nanometers to about 200 nanometers.

13. The composition of claim 1, wherein the cell is CD44+.

14. The composition of claim 13, wherein the cell is CD44+ and CD133+.

15. The composition of claim 14, wherein the cell is CD44+/CD133+/CD24− or expresses CD24 to a limited degree.

16. The composition of claim 1, wherein the cell is a cancer stem cell.

17. The composition of claim 1, wherein the cell expresses one or a combination of: NANOG, OCT4, SOX2, KLF4.

18. The composition of claim 1, wherein the cell expresses CD44, NANOG, OCT4, SOX2 and KLF4.

19. The composition of claim 18, wherein the cell expresses CD133.

20. The composition of claim 1, wherein the cell exhibits mRNA expression for one or a combination of CD44, BMI1, ALDH1A1, ALDH7A1, CXCR4, CXCL3, HGF, DPPA2, HDAC1, HDAC2 and BMPER as measured by RNA sequencing (RNA-seq).

21. The composition of claim 1, wherein the cell is from a primary tumor.

22. The composition of claim 1, wherein the cell is from a biopsy sample from a primary tumor of breast, colon or brain tissue.

23. The composition of claim 1, wherein the outer shell is free of a polycationic material.

24. The composition of claim 1, wherein the cell is in culture from about 7 to about 28 days.

25. The composition of claim 24, wherein the cell is in culture from about 7 to about 10 days.

26. The composition of claim 24, wherein the cell is in culture from about 21 to about 28 days.

27. A system comprising a solid support comprising at least one composition of claim 1 positioned within a cell culture vessel.

28. The system of claim 27, wherein the solid support is a plastic material and comprises from about 1 to about 96 wells, wherein each well comprises contiguous sidewalls that define a volume from about 1 to about 50 ml.

29. The system of claim 27, wherein at least one well comprises a cell culture medium.

30. The system of claim 29, wherein the cell culture medium is a Dulbecco's Modified Eagle's Medium and Ham's F-12 Nutrient Mixture (DMEM/F12) or Dulbecco's Modified Eagle's Medium and Ham's F-12K (Kaighn's) 12 Nutrient Mixture (DMEM-F12-K).

31. The system of claim 29, wherein the cell culture medium comprises the components listed in Table 1.

* * * * *